(12) United States Patent
Berlin

(10) Patent No.: US 12,102,562 B2
(45) Date of Patent: *Oct. 1, 2024

(54) METHODS AND SYSTEMS FOR OCT GUIDED GLAUCOMA SURGERY

(71) Applicant: Michael S. Berlin, West Hollywood, CA (US)

(72) Inventor: Michael S. Berlin, West Hollywood, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/911,988

(22) Filed: Jun. 25, 2020

(65) Prior Publication Data

US 2020/0323687 A1 Oct. 15, 2020

Related U.S. Application Data

(63) Continuation of application No. 16/708,974, filed on Dec. 10, 2019, now Pat. No. 10,993,840, which is a
(Continued)

(51) Int. Cl.
*A61F 9/00* (2006.01)
*A61B 3/10* (2006.01)
(Continued)

(52) U.S. Cl.
CPC .......... *A61F 9/00781* (2013.01); *A61B 3/102* (2013.01); *A61B 3/13* (2013.01);
(Continued)

(58) Field of Classification Search
CPC .............. A61B 3/102; A61B 3/14; A61B 3/13
See application file for complete search history.

(56) References Cited

U.S. PATENT DOCUMENTS

| 4,846,172 A | 7/1989 | Berlin |
| 5,493,109 A | 2/1996 | Wei et al. |

(Continued)

FOREIGN PATENT DOCUMENTS

| CN | 110996760 A | 4/2020 |
| IN | 202017001845 A | 2/2020 |

(Continued)

OTHER PUBLICATIONS

The Optical Coherence Tomography Microsurgical Augmented Reality System (OCT-MARS): A Novel Device for Microsurgeries (Year: 2016).*

(Continued)

*Primary Examiner* — Sana Sahand
(74) *Attorney, Agent, or Firm* — Kenneth D. Springer

(57) ABSTRACT

Disclosed herein are systems and methods for aiding a surgeon to perform a surgical procedure on an eye. The surgical procedure includes inserting an elongate probe from an opening into the eye across an anterior chamber to a target tissue region comprising a trabecular meshwork and a Schlemm's canal. Exemplary systems include an optical microscope for the surgeon to view the eye with a microscope image during the procedure; an optical coherence tomography (OCT) apparatus configured to perform an OCT scan of a target location in the target tissue region during the procedure; and an image processing apparatus configured to generate an augmented image by overlaying an OCT image of target location and a graphical visual element identifying the locations, wherein the graphical visual element is registered with the microscope image to aid the surgeon in advancing a distal end of the elongate probe to the target location.

24 Claims, 33 Drawing Sheets

Related U.S. Application Data continuation of application No. 16/226,127, filed on Dec. 19, 2018, now abandoned, which is a continuation-in-part of application No. 16/011,011, filed on Jun. 18, 2018, now Pat. No. 10,517,760.

(60) Provisional application No. 62/521,310, filed on Jun. 16, 2017.

(51) Int. Cl.
    *A61B 3/13*     (2006.01)
    *A61B 34/20*     (2016.01)
    *A61B 90/00*     (2016.01)
    *A61B 90/20*     (2016.01)
    *A61F 9/007*     (2006.01)
    *A61F 9/008*     (2006.01)
    *A61B 3/00*     (2006.01)
    *A61B 3/14*     (2006.01)
    *A61B 3/15*     (2006.01)
    *A61B 34/00*     (2016.01)
    *A61B 90/50*     (2016.01)

(52) U.S. Cl.
CPC ............. *A61B 34/20* (2016.02); *A61B 90/20* (2016.02); *A61B 90/37* (2016.02); *A61B 90/39* (2016.02); *A61F 9/00802* (2013.01); *A61B 3/0025* (2013.01); *A61B 3/145* (2013.01); *A61B 3/15* (2013.01); *A61B 2034/2057* (2016.02); *A61B 2034/2065* (2016.02); *A61B 34/25* (2016.02); *A61B 2090/364* (2016.02); *A61B 2090/365* (2016.02); *A61B 2090/372* (2016.02); *A61B 2090/3735* (2016.02); *A61B 2090/3983* (2016.02); *A61B 2090/502* (2016.02); *A61F 2009/00851* (2013.01); *A61F 2009/00891* (2013.01)

(56) References Cited

U.S. PATENT DOCUMENTS

| | | |
|---|---|---|
| 6,251,103 B1 | 6/2001 | Berlin |
| 7,192,412 B1 | 3/2007 | Zhou et al. |
| 7,699,882 B2 | 4/2010 | Stamper et al. |
| 8,046,052 B2 | 10/2011 | Verard et al. |
| 8,223,143 B2 | 7/2012 | Dastmalchi et al. |
| 8,308,298 B2 | 11/2012 | Schuhrke et al. |
| 8,540,659 B2 | 9/2013 | Berlin |
| 8,679,089 B2 | 3/2014 | Berlin |
| 8,687,866 B2 | 4/2014 | Marziliano et al. |
| 8,708,488 B2 | 4/2014 | Kraus et al. |
| 8,801,601 B2 | 8/2014 | Prisco et al. |
| 8,882,271 B2 | 11/2014 | Sander |
| 8,983,580 B2 | 3/2015 | Boppart et al. |
| 9,066,784 B2 | 6/2015 | Goldshleger et al. |
| 9,402,539 B2 | 8/2016 | Buckland |
| 9,420,945 B2 | 8/2016 | Coelho et al. |
| 9,456,927 B2 | 10/2016 | Goldshleger et al. |
| 9,495,743 B2 | 11/2016 | Angeley et al. |
| 9,560,963 B2 | 2/2017 | Buckland et al. |
| 9,603,741 B2 | 3/2017 | Berlin |
| 9,629,537 B2 | 4/2017 | Matz et al. |
| 9,642,746 B2 | 5/2017 | Berlin |
| 9,675,244 B1 | 6/2017 | Ren et al. |
| 9,693,829 B2 | 7/2017 | Shi et al. |
| 9,792,721 B2 | 10/2017 | Kosmecki et al. |
| 9,795,446 B2 | 10/2017 | Dimaio et al. |
| 9,820,883 B2 | 11/2017 | Berlin |
| 9,833,357 B2 | 12/2017 | Berlin |
| 10,517,760 B2 | 12/2019 | Berlin |
| 2002/0013572 A1 | 1/2002 | Berlin |
| 2004/0082939 A1 | 4/2004 | Berlin |
| 2004/0102729 A1* | 5/2004 | Haffner ............... A61F 9/00781 |
| | | 623/1.11 |
| 2004/0127843 A1* | 7/2004 | Tu .......................... A61F 9/0017 |
| | | 604/27 |
| 2007/0282313 A1 | 12/2007 | Huang et al. |
| 2008/0082078 A1 | 4/2008 | Berlin |
| 2008/0218743 A1 | 9/2008 | Stetten et al. |
| 2009/0157062 A1 | 6/2009 | Hauger et al. |
| 2010/0324543 A1 | 12/2010 | Kurtz et al. |
| 2011/0118609 A1 | 5/2011 | Goldshleger et al. |
| 2011/0202044 A1 | 8/2011 | Goldshleger et al. |
| 2011/0282190 A1* | 11/2011 | Caffey ................. A61B 5/0066 |
| | | 600/427 |
| 2012/0184846 A1 | 7/2012 | Izatt et al. |
| 2012/0226150 A1 | 9/2012 | Balicki et al. |
| 2012/0259321 A1 | 10/2012 | Vera et al. |
| 2012/0283557 A1 | 11/2012 | Berlin |
| 2013/0085484 A1* | 4/2013 | Van Valen ............. A61B 18/22 |
| | | 606/6 |
| 2013/0103011 A1 | 4/2013 | Grant et al. |
| 2013/0265545 A1 | 10/2013 | Buckland et al. |
| 2014/0114297 A1 | 4/2014 | Woodley et al. |
| 2014/0142422 A1 | 5/2014 | Manzke et al. |
| 2014/0160264 A1 | 6/2014 | Taylor et al. |
| 2014/0221822 A1 | 8/2014 | Ehlers et al. |
| 2015/0055093 A1 | 2/2015 | Ehlers et al. |
| 2015/0077528 A1* | 3/2015 | Awdeh .................... G06T 11/00 |
| | | 348/78 |
| 2015/0124216 A1 | 5/2015 | Abramoff et al. |
| 2015/0342460 A1 | 12/2015 | Izatt et al. |
| 2016/0089015 A1 | 3/2016 | Eslami et al. |
| 2016/0095751 A1 | 4/2016 | Berlin |
| 2016/0157954 A1 | 6/2016 | Sagon et al. |
| 2016/0192835 A1 | 7/2016 | Matz et al. |
| 2016/0262606 A1 | 9/2016 | Mosaed et al. |
| 2016/0324593 A1 | 11/2016 | El-haddad et al. |
| 2017/0020732 A1 | 1/2017 | Berlin |
| 2017/0049322 A1 | 2/2017 | Heeren et al. |
| 2017/0119579 A9 | 5/2017 | Berlin |
| 2017/0156588 A1* | 6/2017 | Ren ......................... A61B 3/102 |
| 2017/0202708 A1 | 7/2017 | Berlin |
| 2017/0231714 A1 | 8/2017 | Kosmecki et al. |
| 2017/0251951 A1 | 9/2017 | Hunter et al. |
| 2017/0280989 A1 | 10/2017 | Heeren |
| 2017/0340483 A1 | 11/2017 | Rill et al. |
| 2018/0207029 A1 | 7/2018 | Herekar et al. |
| 2018/0235462 A1 | 8/2018 | Gooi et al. |
| 2018/0353066 A1 | 12/2018 | Uji et al. |
| 2018/0360310 A1 | 12/2018 | Berlin |
| 2018/0360655 A1 | 12/2018 | Berlin |
| 2019/0117459 A1 | 4/2019 | Berlin |
| 2020/0188173 A1 | 6/2020 | Berlin |
| 2020/0229971 A1 | 7/2020 | Berlin |
| 2020/0281766 A1 | 9/2020 | Berlin |

FOREIGN PATENT DOCUMENTS

| | | |
|---|---|---|
| KR | 1020200023385 A | 3/2020 |
| WO | WO-2014168767 A1 | 10/2014 |
| WO | WO-2018049246 A1 | 3/2018 |
| WO | WO-2018232397 A1 | 12/2018 |

OTHER PUBLICATIONS

Assessment of trabecular meshwork width using swept source optical coherence tomography, Tun et al., 2013, Graefes Arch Clin Exp Ophthalmol Jun. 2013;251(6):1587-92. (Year: 2013).*
"U.S. Appl. No. 15/868,904, Final Office Action mailed Oct. 24, 2018", 12 pgs.
"U.S. Appl. No. 15/868,904, Non Final Office Action mailed Jun. 29, 2018", 20 pgs.
"U.S. Appl. No. 15/868,904, Preliminary Amendment filed Feb. 15, 2018", 7 pgs.
"U.S. Appl. No. 15/868,904, Response filed Sep. 12, 2018 to Non Final Office Action mailed Jun. 29, 2018", 14 pgs.
"U.S. Appl. No. 16/011,011 Supplemental Amendment and Response filed Jun. 5, 2019", 12 pgs.
"U.S. Appl. No. 16/011,011, Non Final Office Action mailed Dec. 5, 2018", 43 pgs.

(56) References Cited

OTHER PUBLICATIONS

"U.S. Appl. No. 16/011,011, Notice of Allowance mailed Aug. 23, 2019", 9 pgs.
"U.S. Appl. No. 16/011,011, Notice of Non-Compliant Amendment mailed Jun. 14, 2019", 7 pgs.
"U.S. Appl. No. 16/011,011, Preliminary Amendment filed Jun. 18, 2018", 15 pgs.
"U.S. Appl. No. 16/011,011, Preliminary Amendment filed Jul. 16, 2018", 4 pgs.
"U.S. Appl. No. 16/011,011, Response filed May 2, 2019 to Non Final Office Action mailed Dec. 5, 2018", 13 pgs.
"U.S. Appl. No. 16/011,011, Response filed Jun. 25, 2019 to Non-Compliant Amendment mailed Jun. 14, 2019", 12 pgs.
"U.S. Appl. No. 16/226,127, Non Final Office Action mailed Aug. 22, 2019", 23 pgs.
"U.S. Appl. No. 16/226,127, Notice of Non-Compliant Amendment mailed Nov. 12, 2019", 7 pgs.
"U.S. Appl. No. 16/226,127, Response filed Sep. 9, 2019 to Non-Final Office Action mailed Aug. 22, 2019", 18 pgs.
"U.S. Appl. No. 16/692,839 Supplemental Preliminary Amendment filed May 19, 2020", 17 pgs.
"U.S. Appl. No. 16/708,974, Examiner Interview Summary mailed Jun. 16, 2020", 3 pgs.
"U.S. Appl. No. 16/708,974, Non Final Office Action mailed Apr. 28, 2020", 33 pgs.
"U.S. Appl. No. 16/708,974, Response filed Jun. 15, 2020 to Non Final Office Action mailed Apr. 28, 2020", 17 pgs.
"Co-pending U.S. Appl. No. 15/808,809, filed Nov. 9, 2017".
"Integration of a Spectral Domain Optical Coherence Tomography System into a Surgical Microscope for Intraoperative Imaging", (2011).
"International Application Serial No. PCT/US2018/038072, International Preliminary Report on Patentability mailed Dec. 26, 2019", 8 pgs.
"International Application Serial No. PCT/US2018/038072, International Search Report mailed Oct. 15, 2018", 4 pgs.
"International Application Serial No. PCT/US2018/038072, Written Opinion mailed Oct. 15, 2018", 6 pgs.
"IOCT® Discover a new dimension with intraoperative OCT", Haag Streit Surgical, (2010), 12 pgs.
"Korean Application Serial No. 10-2020-7001592, Notice of Preliminary Rejection mailed May 25, 2020", 3 pgs.
Bartlett, "The Use of Augmented Reality in the Operating Room: a Review", Department of Electrical and Computer Engineering, University of British Columbia, [Online], Retrieved from the Internet on Jul. 12, 2018, <URL https://www.cs.ubc.ca/~tmm/courses/533-09/projects/john/report.pdf>, (2009), 1-18.
Bende, et al., "Fiberoptic Partial Coherence Interferometry (PCI): A Novel Approach to Locate Schlemm's Canal for MIGS Surgery", Investigative Ophthalmology & Visual Science 57. 12, (2016), 6505-6505.
Bentley, et al., "Anatomical Variation of Human Collector Channel Orifices", Invest Ophthalmol Vis Sci.; 57, (2016), 1153-1159.
Berlin, et al., "Excimer Laser Trabeculostomy (ELT): An Effective MIGS Procedure for Open-Angle Glaucoma", in Samples & Ahmed, Surgical Innovations in Glaucoma, (New York: Springer Science + Business Media New York) Ch. 8, (2014), 85-95.
Carrasco-Zevallos, et al., "Review of intraoperative optical coherence tomography: technology and applications", Biomedical Optics Express, vol. 8, No. 3, (Mar. 2017), 1607-1637.
Carreon, et al., "Aqueous Outflow—A continuum from trabecular meshwork to episcleral veins", Progress in Retinal and Eye Research, 57, (2017), 108-133.
Chockalingham, et al., "Excimer Laser Trabeculotomy- A Novel, Minimally Invasive Procedure for Patients with Glaucoma", Kerala Journal of Ophthalmology, (Mar. 2007), 72-75.
Dang, et al., "Rapid learning curve assessment in an ex vivo training system for microincisional glaucoma surgery", Scientific Reports 7, 1605, (May 9, 2017), 1-9.

Donovan, et al., "Microscope-Integrated Optical Coherence Tomography", Retina Today, (Jan./Feb. 2016), 52-56.
Ehlers, et al., "Determination of Feasibility and Utility of Microscope-integrated OCT During Ophthalmic Surgery: the Discover Study Rescan Results", JAMA Ophthalmol, vol. 133(10), (Oct. 2015), 1124-1132.
Ehlers, et al., "Integrative Advances for OCT-Guided Ophthalmic Surgery and Intraoperative OCT: Microscope Integration, Surgical Instrumentation, and Heads-Up Display Surgeon Feedback", PLoS One 9(8), e105224, 1-10.
Galeotti, et al., "The OCT Penlight: In-situ image guidance for microsurgery", SPIE Medical Imaging, Paper #7625-1, [Online], Retrieved from the Internet on Jul. 12, 2018, <URL https://www.researchgate.net/publication/241395732_The_OCT_penlight_In-situ_image_guidance_for_microsurgery>, (Feb. 2010), 1-6.
Garg, et al., "Advances in Glaucoma Surgery", Del J Ophthalmol—Vo 27 No. 1, (Jul.-Sep. 2016), 44-49.
Hahn, et al., "Preclinical evaluation and intraoperative human retinal imaging with a high-resolution microscope-integrated spectral domain optical coherence tomography device", Retina, 33(7), (2013), 1328-1337.
Hahn, et al., "The Use of Optical Coherence Tomography in Intraoperative Ophthalmic Imaging", Ophthalmic Surg. Lasers Imaging, 42(0), (Jul. 2011), S85-S94.
Hann, et al., "Anatomic Changes in Schlemm's Canal and Collector Channels in Normal and Primary Open-Angle Glaucoma Eyes Using Low and High Perfusion Pressures", Invest. Ophthalmol. Vis. Sci., vol. 55(9), (Sep. 2014), 5834-5841.
Horvath, "The Optical Coherence Tomography Microsurgical Augmented Reality System (OCT-MARS): A Novel Device for Microsurgeries", PhD Thesis, The Robotics Institute, Carnegie Mellon University, Pittsburgh, Pennsylvania, (Sep. 2016), 1-72.
Huang, et al., "Automated circumferential construction of first-order aqueous humor outflow pathways using spectral-domain optical coherence tomography", Journal of Biomedical Optics 22(6), 066010, <https://doi.org/10.1117/1.JBO.22.6.066010>, (Jun. 15, 2017), 1-7.
Huang, et al., "Structural and functional imaging of aqueous humour outflow: a review", Clinical and Experimental Ophthalmology, 46, Mar. 2018, (Sep. 12, 2017), 158-168.
Johnstone, M, "Intraocular pressure control through linked trabecular meshwork and collector channel motion", in Knepper & Samples, New Concepts in Glaucoma, Glaucoma Research and Clinical Advances: 2016 to 2018. Kugler Publications, (Feb. 2016), 41-86.
Kagemann, et al., "Identification and Assessment of Schlemm's Canal by Spectral-Domain Optical Coherence Tomography", Investigative Ophthalmology & Visual Science, vol. 51, No. 8, (Aug. 2010), 4054-4059.
Lee, et al., "Stimulated penetrating keratoplasty using real-time virtual intraoperative surgical optical coherence tomography", Journal of Biomedical Optics, vol. 19(3), 030502, (Mar. 6, 2014), 1-3.
Nicolau, et al., "An augmented reality system to guide radio-frequency tumour ablation", Comp. Anim. Virtual Worlds, 16, (2005), 1-10.
Nuzzi, et al., "Glaucoma: Biological Trabecular and Neuroretinal Pathology with Perspectives of Therapy Innovation and Preventive Diagnosis", Frontiers in Neuroscience, vol. 11, Article 494, (Sep. 5, 2017), 1-22.
Palanker, et al., "Femtosecond Laser-Assisted Cataract Surgery with Integrated Optical Coherence Tomography", vol. 2 Issue 58 58ra85, (Nov. 17, 2010), 1-9.
Sharma, et al., "Continuous intraoperative OCT guided management of post-deep anterior lamellar keratoplasty descemet's membrane detachment", Saudi Journal of Ophthalmology, 30, (2016), 133-136.
Sharma, et al., "Technique: Microscope-integrated intraoperative optical coherence tomography-guided small-incision lenticule extraction: New surgical technique", vol. 43, Issue 10, (Oct. 10, 2017), 1245-1250.
Tao, et al., "Microscope-integrated intraoperative OCT with electrically tunable focus and heads-up display for imaging of ophthalmic surgical maneuvers", Biomedical Optics Express, 5(6), (2014), 1877-1885.

(56) References Cited

OTHER PUBLICATIONS

Uji, et al., "In Vivo Identification of the Posttrabecular Aqueous Outflow Pathway Using Swept-Source Optical Coherence Tomography", Invest Ophthalmol Vis Sci. 57, (2016), 4162-4169.
Vokes, et al., "Optical Coherence Tomography-Enhanced Microlaryngoscopy: Preliminary Report of a Noncontact Optical Coherence Tomography System Integrated With a Surgical Microscope", Ann Otol Rhinol Laryngol. 117(7), (2008), 538-547.
Xin, et al., "Aqueous outflow regulation: Optical coherence tomography implicates pressure-dependent tissue motion", Experimental eye research 158, (May 2017), 171-186.
Xin, et al., "OCT Study of Mechanical Properties Associated with Trabecular Meshwork and Collector Channel Motion in Human Eyes", PLOS One, (Sep. 6, 2016), 20 pgs.
Xin, C., et al., "Aqueous outflow regulation: Optical coherence tomography implicates pressure-dependent tissue motion", Experimental Eye Research, [Online] Retrieved from the internet: <http://dx.doi.org/10.1016/j.exer.2016.06.007>, (2016).
Yan, et al., "Schlemm's Canal and Trabecular Meshwork in Eyes with Primary Open Angle Glaucoma: A Comparative Study Using High-Frequency Ultrasound Biomicroscopy", PLOS One, (Jan. 2016), 1-15.
Yu, et al., "Evaluation of microsurgical tasks with OCT-guided and/or robot-assisted ophthalmic forceps", Biomedical Optics Express, (Jan. 2015), 457-472.
"U.S. Appl. No. 16/692,839, Restriction Requirement mailed Jun. 16, 2020", 15 pgs.
"European Application Serial No. 18818673.8, Extended European Search Report mailed Jun. 24, 2020", 4 pgs.
"U.S. Appl. No. 16/692,839, Response filed Jun. 23, 2020 to Restriction Requirement mailed Jun. 16, 2020", 21 pgs.
"European Application Serial No. 18818673.8, Communication Pursuant to Article 94(3) EPC mailed Jul. 9, 2020", 7 pgs.
"Korean Application Serial No. 10-2020-7001592, Response filed Jul. 24, 2020—to Notice of Preliminary Rejection mailed May 25, 2020", w English Claims, 25 pgs.
"U.S. Appl. No. 16/692,839, Non Final Office Action mailed Aug. 5, 2020", 32 pgs.
"U.S. Appl. No. 16/708,974, Final Office Action mailed Aug. 5, 2020", 36 pgs.
"U.S. Appl. No. 16/692,839, Response filed Sep. 17, 2020 to Non Final Office Action mailed Aug. 5, 2020", 23 pgs.
"U.S. Appl. No. 16/708,974, Response filed Sep. 17, 2020 to Final Office Action mailed Aug. 5, 2020", 18 pgs.

\* cited by examiner

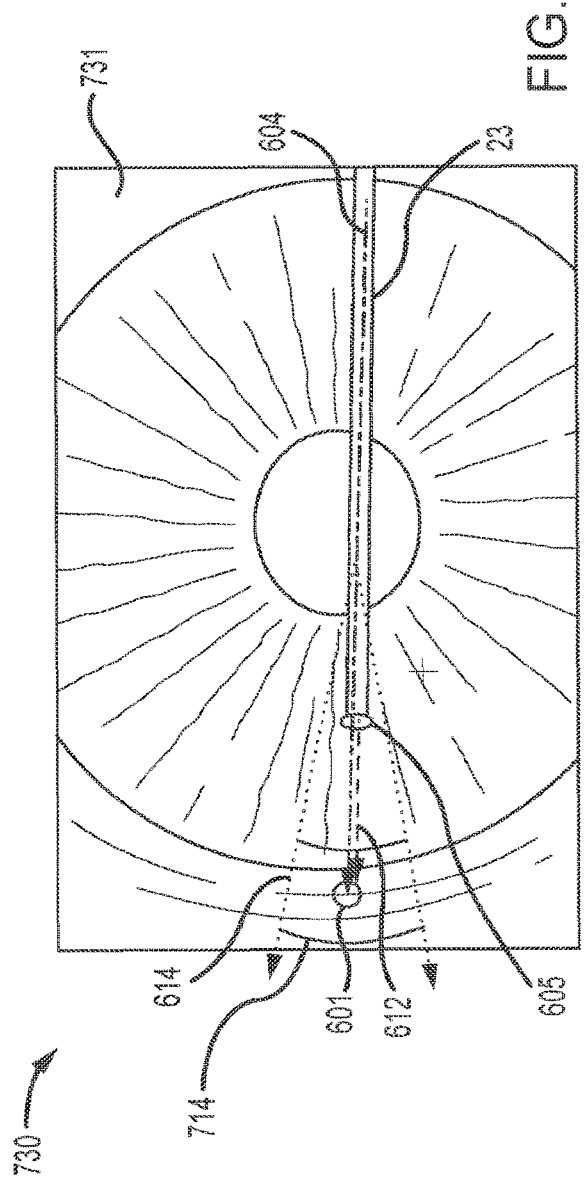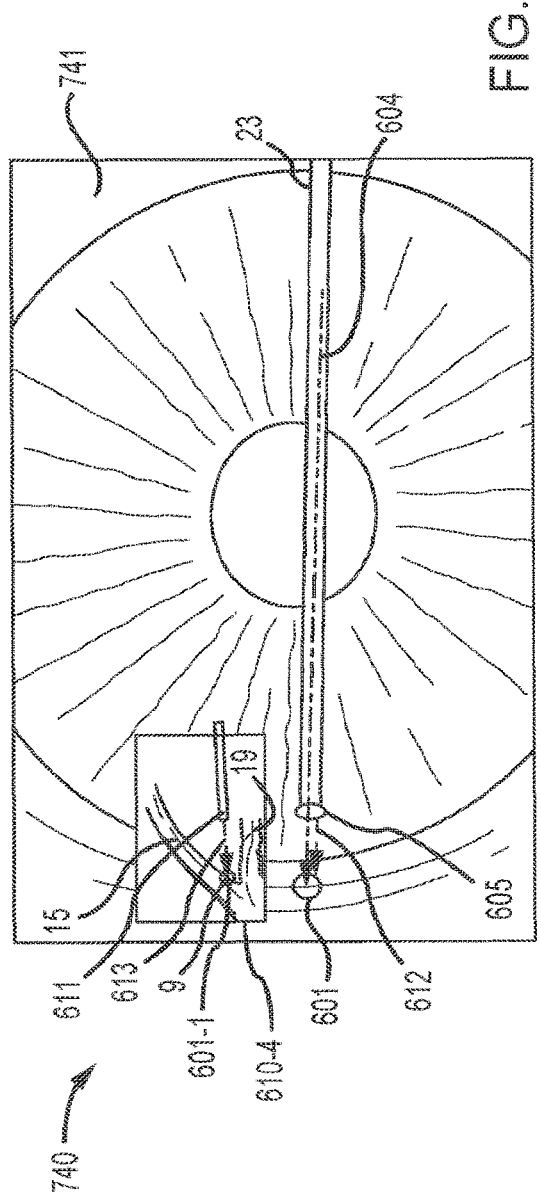

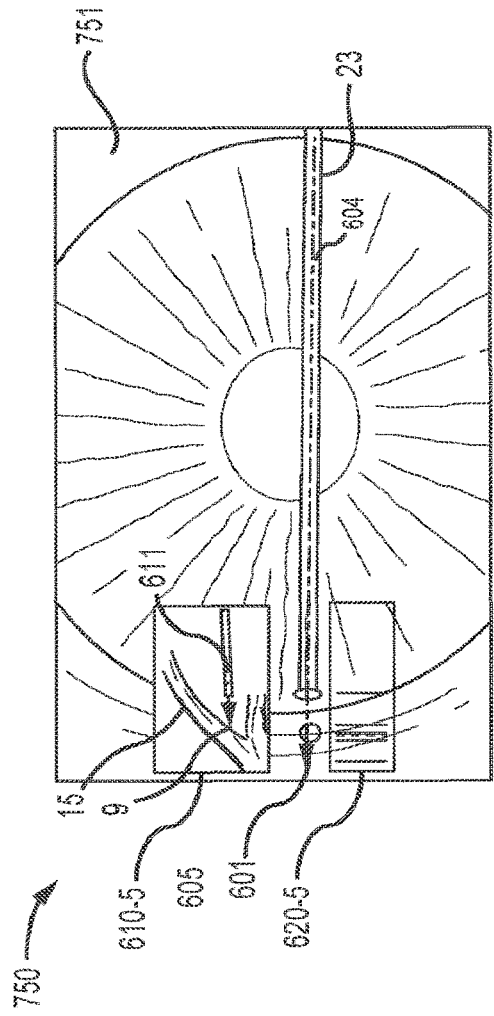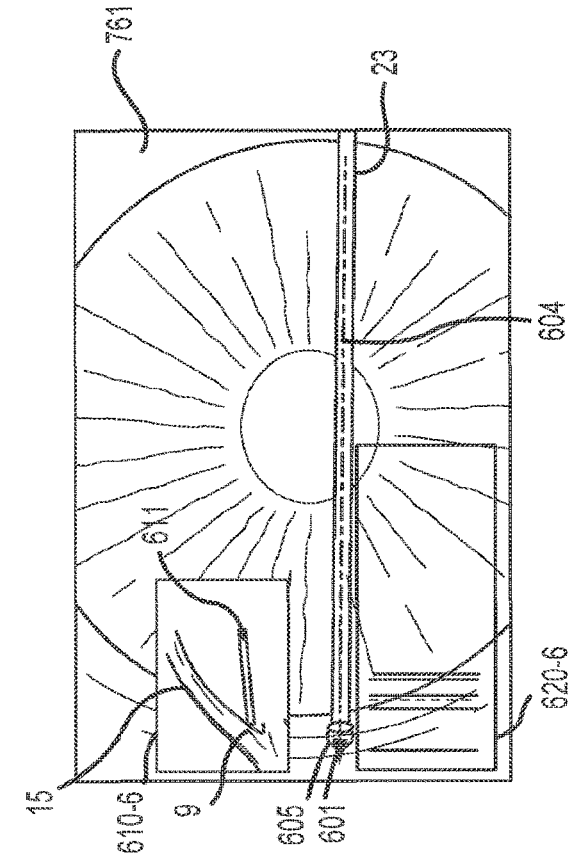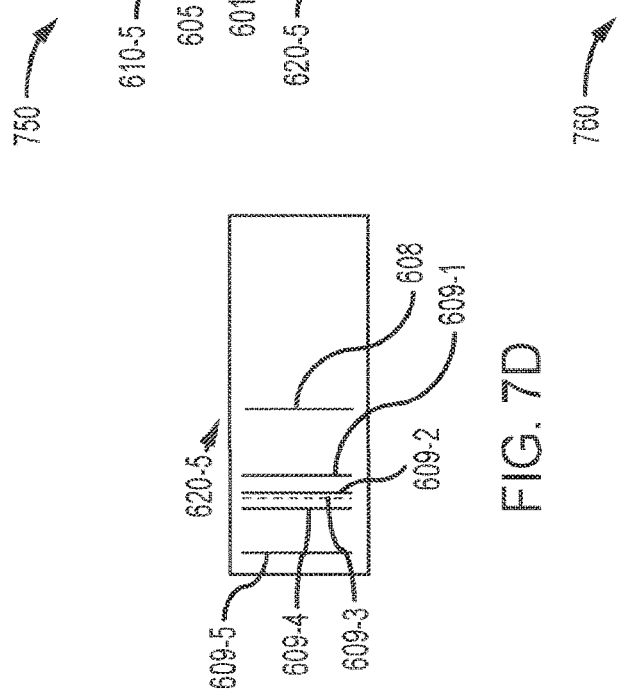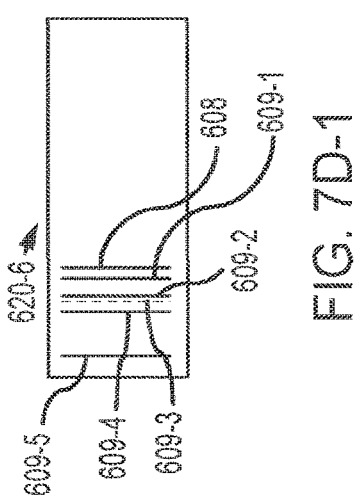

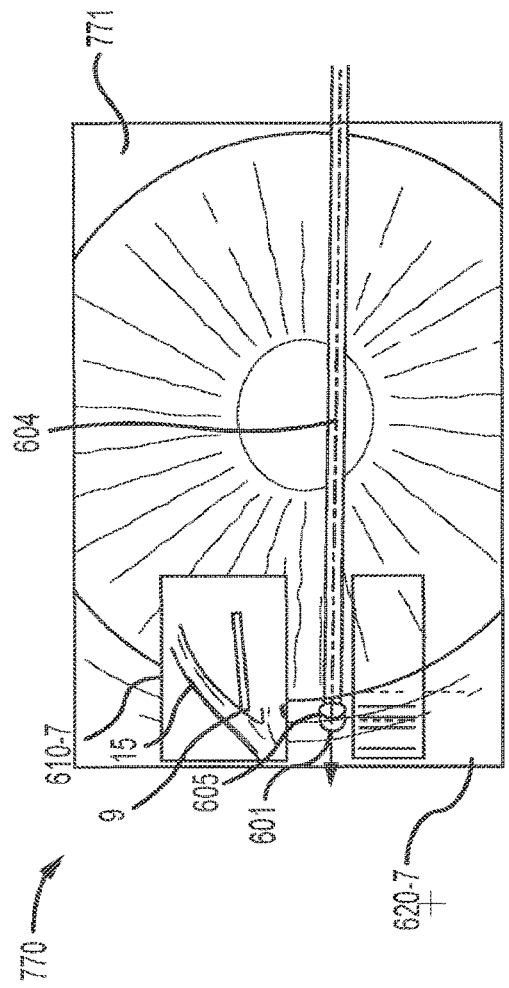
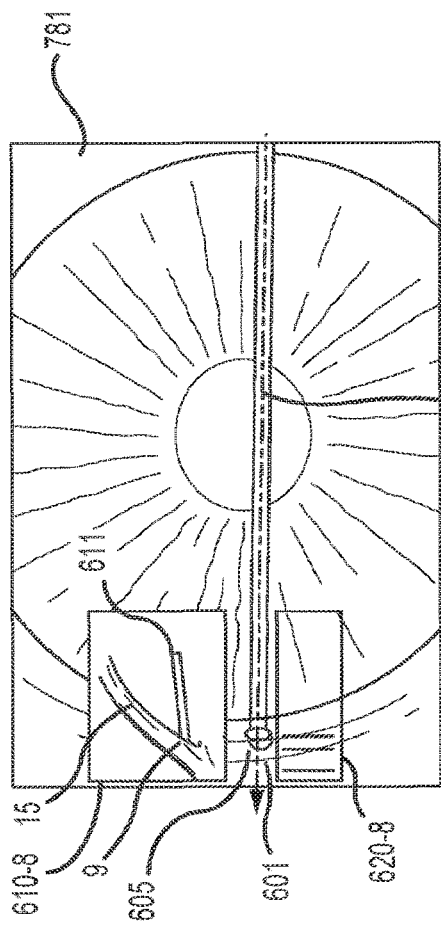
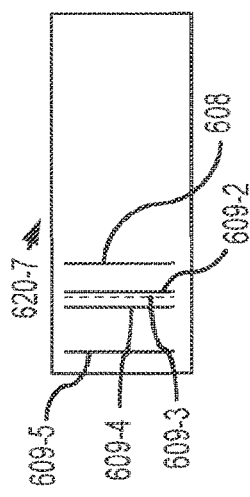
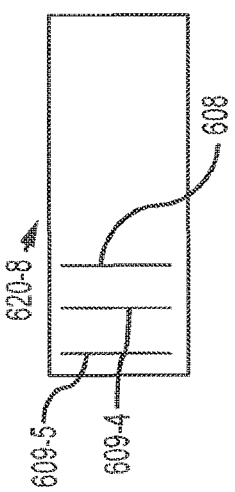

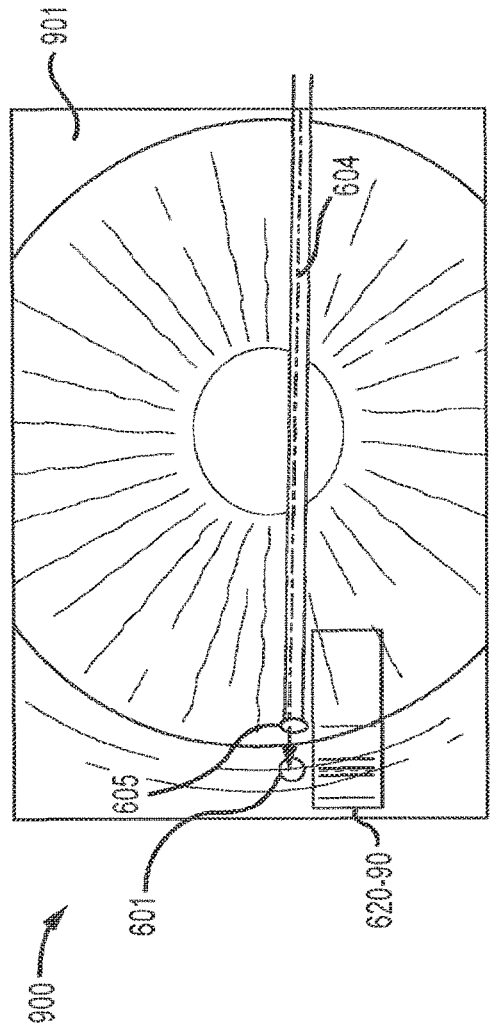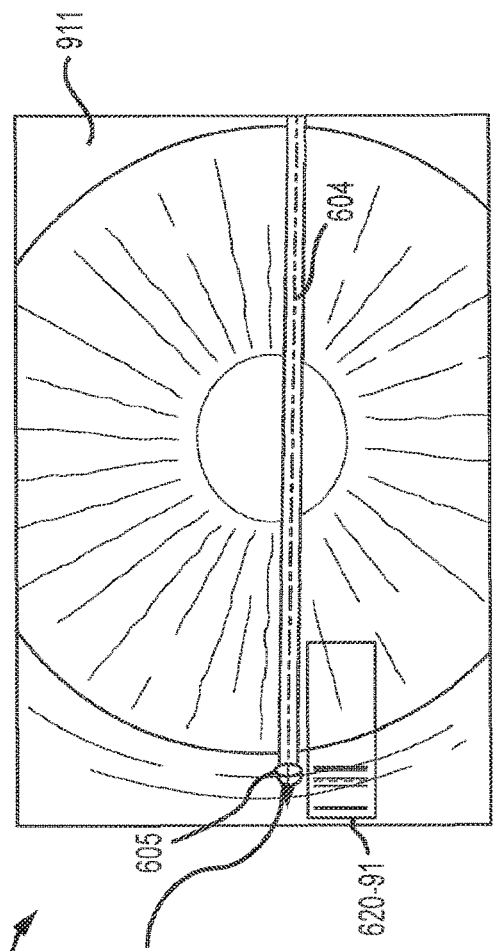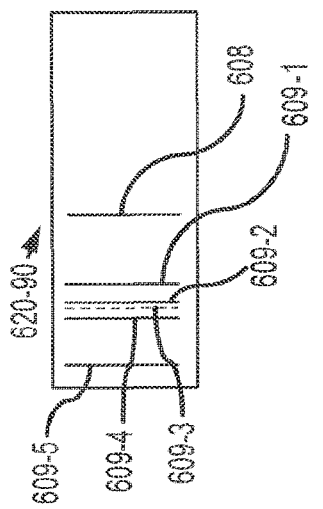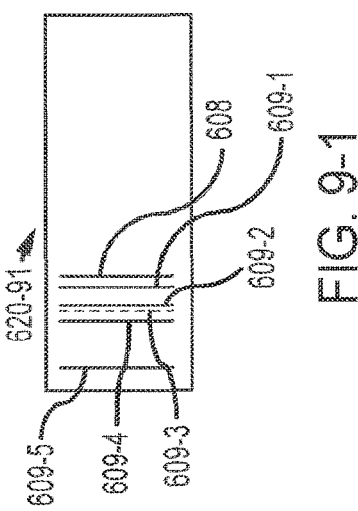

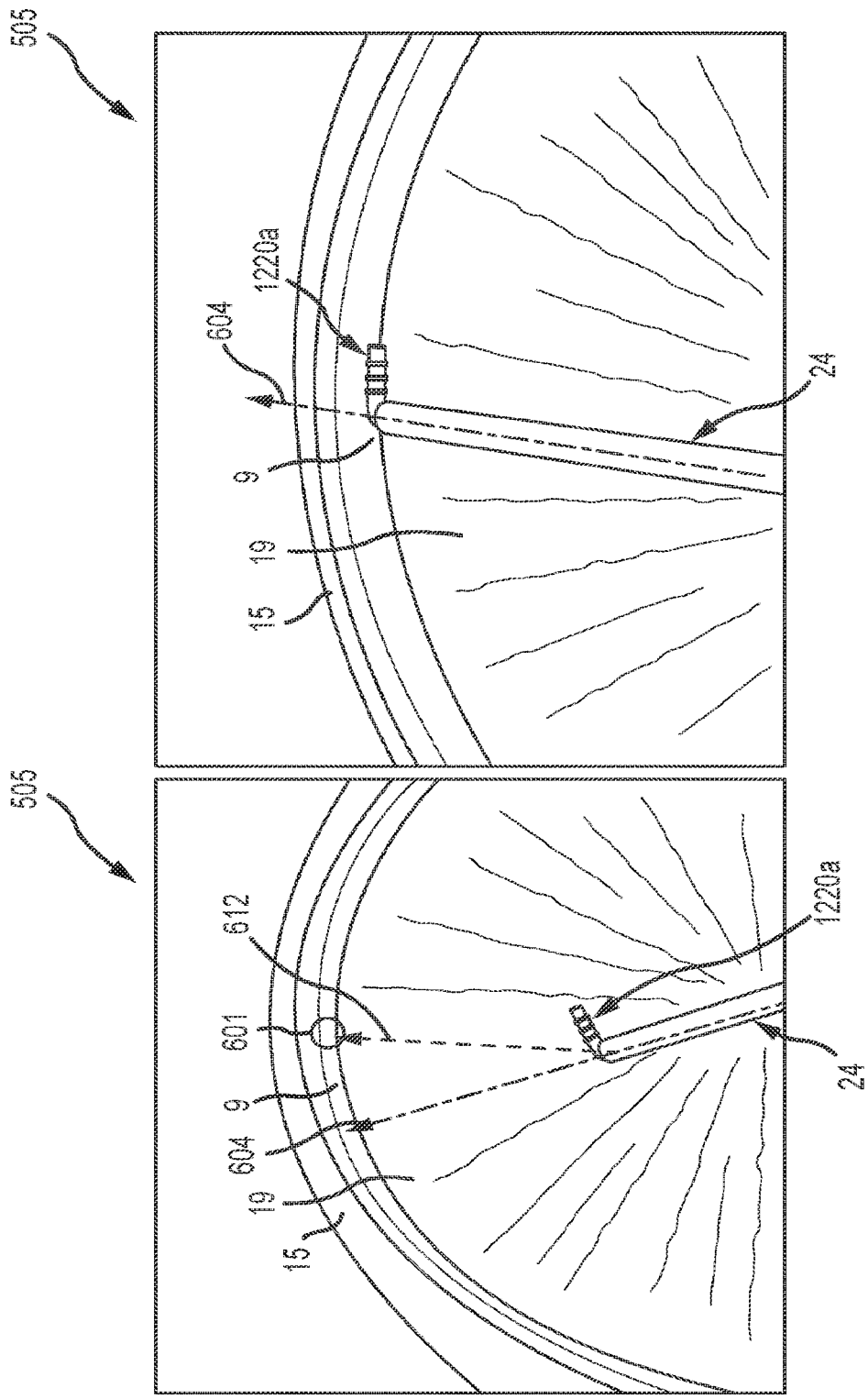

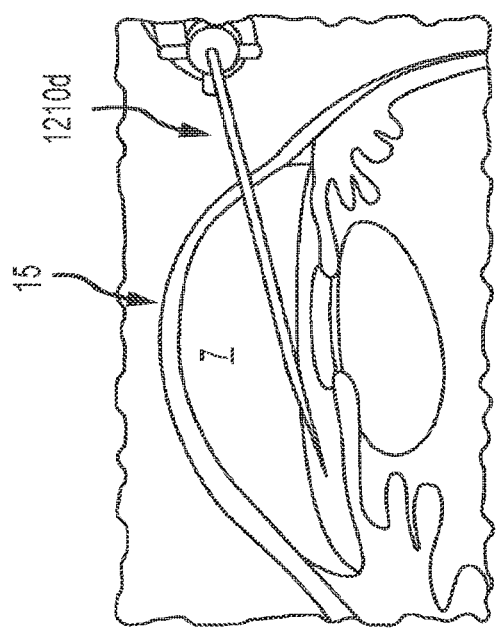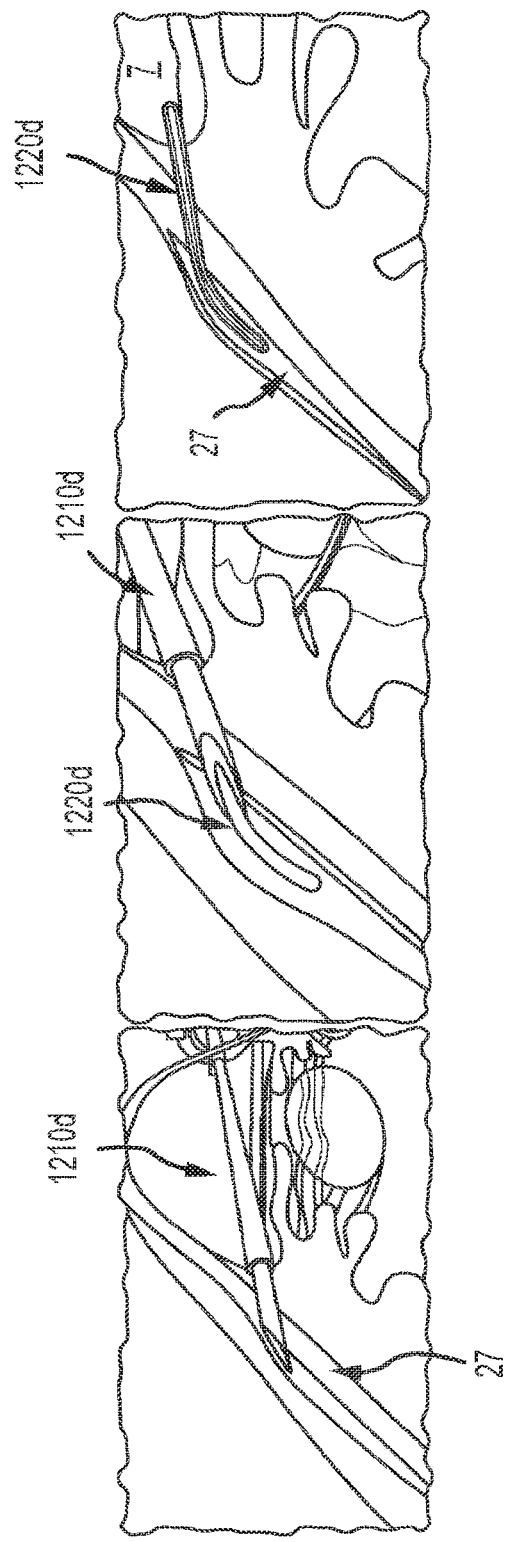

METHODS AND SYSTEMS FOR OCT GUIDED GLAUCOMA SURGERY

CROSS-REFERENCE

This application is a continuation of U.S. application Ser. No. 16/708,974, filed Dec. 10, 2019, which is a continuation of U.S. application Ser. No. 16/226,127, filed Dec. 19, 2018, which is a continuation-in-part of U.S. application Ser. No. 16/011,011 filed Jun. 18, 2018, entitled "Methods and systems for OCT Guided Glaucoma Surgery" which claims the benefit of provisional patent application U.S. Prov. Ser. App. No. 62/521,310 filed Jun. 16, 2017, entitled "Methods and Systems for OCT Guided Glaucoma Surgery". This application is also related to U.S. application Ser. No. 15/868,904 filed Jan. 11, 2018 entitled "Methods and Systems for OCT Guided Glaucoma Surgery". Each of these applications are incorporated herein by reference in their entirety.

BACKGROUND

Glaucoma is a disease of the eye in which intraocular structures critical to vision is irreversibly damaged. These structures include portions of the retina and especially portions of the optic nerve. Glaucoma, a treatable condition, is cited as the second leading cause of blindness in the United States. Several million people are affected. There are two major types of glaucoma, open angle glaucoma, and closed angle glaucoma. Open angle glaucoma, the most common type of glaucoma, occurs when the normal appearing outflow pathways malfunction such that the eye does not adequately drain fluid which results in an intraocular elevation of pressure. Elevated intraocular pressure (IOP) in most open-angle glaucoma is due to an obstruction of aqueous outflow localized predominantly at the juxtacanalicular trabecular meshwork (TM) and the inner wall of Schlemm's canal (SC).

Treatments for elevated IOP due to outflow obstruction include topical and systemic medications, office-based laser procedures, and risk inherent invasive surgical procedures (trabeculectomy/tube shunt). Examples of laser procedures include argon laser trabeculoplasty (ALT) and selective laser trabeculoplasty (SLT). More recently less invasive surgical procedures have been introduced into the treatment paradigms, commonly termed minimally invasive glaucoma surgery (MIGS), or micro-invasive glaucoma surgical procedures. Current approaches of IOP reduction by MIGS include increasing trabecular outflow by bypassing the juxtacanalicular trabecular meshwork (TM) and inner wall of SC, increasing uveoscleral outflow via suprachoroidal pathways, reducing aqueous production from the ciliary body, or creating an external, subconjunctival/suprascleral drainage pathway.

The general concept of MIGS is typically to bypass outflow obstruction and enable resumption of flow via the eye's intrinsic outflow system which is often intact and functional beyond the region of outflow obstruction, rather than creating alternative pathways which may have significantly greater short and/or long term risks.

MIGS procedures often involve visualization and access to the intraocular outflow system. Due to the shape of the cornea and the location of intraocular structures related to MIGS procedures in the region where the iris appears to meet the peripheral cornea, total internal reflection occurs and can prevent a surgeon from viewing those outflow structures that reside beyond the "critical angle" of the optical pathway, which in the context of the anterior chamber surgical procedures disclosed herein, can also be referred to as the "critical angle" of the anterior chamber optical viewing pathway. According to some embodiments, the optical pathway as disclosed herein can refer to the viewing of the anterior chamber angle structures and not the optical pathway of the eye's visual system, e.g. near the center of the cornea to the macula. As such, devices to allow visualization of those outflow structures are often necessary for a surgeon to perform MIGS procedures. Goniolenses, both direct (allowing a straight optical pathway for viewing those structures) and indirect (using mirrors to view those structures) function by overcoming total internal reflection. However, intraoperative use of goniolenses can require significant dexterity and a steep learning curve, which may limit successful MIGS procedures to certain skilled surgeons in at least some instances.

In at least some of these surgical procedures, a surgical opening is created through the trabecular meshwork and the inner wall of Schlemm's canal to enable improved fluidic access into Schlemm's canal in order to reduce intra ocular pressure. Prior approaches to accurately target Schlemm's canal are often less than ideal. Thus, it would be beneficial to provide methods and apparatuses that provide improved consistency and accuracy in targeting Schlemm's canal and other structures of the eye. Also, work in relation to the present disclosure suggests that at least some of the prior approaches may result in openings into Schlemm's canal at less than ideal locations, for example at locations which are far away from collector channels. Alternative MIGS devices which bypass Schlemm's canal and drain aqueous fluid into the suprachoroidal space can also benefit from targeted location placement by improving visualization of adjacent ocular structures. Examples of such implant devices include the intracanalicular iStent®, and iStent inject and the suprachoroidal CyPass® microstent. Excimer laser trabeculostomy (ELT) which creates patent channel openings into Schlemm's canal can also benefit from improved targeting and visualization of structures in the eye.

Current methods and apparatus for viewing structures of the eye near the irido-corneal angle, such as the trabecular meshwork and scleral spur, can be less than ideal in at least some instances. For example, a goniolens can be somewhat more difficult to use than would be ideal, and it would be beneficial to provide improved methods an apparatus for viewing the structures of the eye near the irido-corneal angle during surgery in this region.

In light of the above, it would be helpful to have improved methods and apparatus for imaging the eye during surgical procedures, targeting outflow structures of the eye such as Schlemm's canal, and determining target locations for openings through the trabecular meshwork and into Schlemm's canal to improve flow.

SUMMARY

The methods and apparatus disclosed herein allow glaucoma surgery of the outflow structures, including MIGS and many varieties thereof, to be performed without a goniolens. According to an aspect of the invention, an ophthalmic surgeon can identify these outflow structures and operate on these structures through virtual images and representations of the structures and the surgical tools generated using optical coherence tomography (OCT) scanning.

In one aspect, a system for aiding a physician to perform a surgical procedure on an eye is provided. The operation procedure comprises inserting an elongate probe from an opening into the eye across an anterior chamber to a target tissue region comprising a trabecular meshwork and a Schlemm's canal. The system comprises: an optical microscope for the surgeon to view the eye with a microscope image during the procedure; one or more optical coherence tomography (OCT) apparatus configured to perform OCT scans of one or more target locations in the target tissue region in real time during the procedure; and an image processing apparatus configured to generate a plurality of augmented images (real and virtual) by enabling viewing of and in some cases overlaying (1) one or more OCT images of the one or more target locations and/or (2) a plurality of graphical visual elements identifying the one or more target locations, wherein the plurality of graphical visual elements is registered with the real microscope image to aid the physician in advancing a distal end of the elongate probe to the one or more target locations.

In another aspect, embodiments of the present invention encompass methods of performing a surgical procedure on an eye of a patient. Exemplary methods may include viewing a real-time view on a viewing device, where the real-time view includes (i) a microscope view of the eye and (ii) an augmented image having the microscope view or a microscope image of the eye. The augmented image may also have an optical coherence tomography (OCT) image of a target tissue region. The OCT image can be registered with the microscope view or the microscope image. The OCT image can enable identification of a target location positioned in the target tissue, and wherein an actual target location is not visible in the microscope view or the microscope image. Exemplary methods may further include advancing a distal end of an elongate probe within an anterior chamber of the eye toward the target tissue region while viewing the microscope view or the augmented image on the viewing device, where the distal end of the elongate probe is initially visible in the microscope view or the microscope image and thereafter becomes not visible in the microscope view or the microscope image due to total internal reflection in the region of the eye wherein lies the target tissue. Exemplary methods may also include performing the surgical procedure at the actual target location using the elongate probe while the distal end of the elongate probe is not visible in the microscope view or the microscope image, and while perceiving information from the augmented image regarding a relative position of the distal end of the elongate probe with respect to the target location.

According to some embodiments, a graphical visual element identifying the target location can be overlaid the microscope view or the microscope image. In some embodiments, the real-time view includes the augmented image having the microscope view of the eye, the OCT image is registered with the microscope view, and the actual target location is not visible in the microscope view. A graphical visual element may be overlaid the microscope view. In some embodiments, the advancing step includes advancing the distal end of the elongate probe within the anterior chamber of the eye toward the target tissue region while viewing the augmented image on the viewing device, where the distal end of the elongate probe is initially visible in the microscope view and thereafter becomes not visible in the microscope view due to total internal reflection in the region of the eye wherein lies the target tissue region. In some embodiments, the performing step includes performing the surgical procedure at the target location using the elongate probe while the distal end of the elongate probe is not visible in the microscope view, and while perceiving information from the microscope view regarding a relative position of the distal end of the elongate probe with respect to the target location. In some embodiments, the real-time view includes the augmented image, and the OCT image registered with the microscope view or the microscope image includes information regarding Schlemm's canal and the collector channel system. In some embodiments, the real-time view includes the augmented image, and the OCT image registered with the microscope view or the microscope image includes information regarding a relative position of the distal end of the elongate probe with respect to the target location.

In some instances, a graphical visual element corresponding to the distal end of the elongate probe is overlaid the microscope view or the microscope image, and the advancing step includes advancing the distal end of the elongate probe toward the target tissue region, while viewing the graphical visual element corresponding to the distal end of the elongate probe and the graphical visual element corresponding to the target location on the augmented image, as the distal end of the elongate probe approaches and contacts the target tissue region. In some embodiments, a graphical visual element corresponding to the distal end of the elongate probe and a graphical visual element corresponding to a surface of the trabecular meshwork of the eye are overlaid the microscope view or the microscope image, and the method includes determining there is contact between the distal end of the elongate probe and the surface of the trabecular meshwork when the graphical visual element corresponding to the distal end of the elongate probe and the graphical visual element corresponding to a surface of the trabecular meshwork are sufficiently close. In some embodiments, a graphical visual element corresponding to a surface of a trabecular meshwork and a graphical visual element corresponding to a juxtacanalicular trabecular meshwork of the eye are overlaid the microscope view or the microscope image, and the method includes determining whether a trabecular meshwork of the eye is sufficiently compressed when the graphical visual element corresponding to surface of the trabecular meshwork and the graphical visual element corresponding to the juxtacanalicular trabecular meshwork are sufficiently close. In some embodiments, a graphical visual element corresponding to an inner wall of Schlemm's canal of the eye is overlaid the microscope view or the microscope image, and the method includes determining that the inner wall of Schlemm's canal has been penetrated when the graphical visual element corresponding to the inner wall of Schlemm's canal disappears from the microscope view or the microscope image.

In some instances, a guidance arrow is overlaid the microscope view or the microscope image, and the guidance arrow points to the graphical visual element identifying the target location. In some instances, a guidance arrow is overlaid the microscope view or the microscope image, and the guidance arrow points to the graphical visual element identifying the target location. In some methods, the advancing step includes advancing the distal end of the elongate probe toward the target location while using the guidance arrow as a guide. In some methods, the performing step includes ablating the target location with laser pulses emanating from the elongate probe, and following the creation of a channel which connects the anterior chamber to a lumen of Schlemm's canal at the target location, a second guidance arrow is overlaid the microscope view of the microscope image, where the second guidance arrow points to a second graphical visual element identifying a second target location of the eye, and methods may further include advancing the distal end of the elongate probe toward the second target location while using the second guidance arrow as a guide. Methods may also include ablating the second target location with the elongate probe.

In some embodiments, the viewing device can be a display device, a microscope device, a heads up display, a viewing monitor, a virtual reality viewing device, or an augmented reality viewing device. In some embodiments, a graphical visual element identifying the distal end of the elongate probe can be overlaid the microscope view or the microscope image, and the relative position of the distal end of the elongate probe with respect to the target location can be based on a relative position of the distal end of the elongate probe with respect to the graphical visual element identifying the target location. In some instances, the actual target location is not visible in the microscope view or the microscope image due to total internal reflection in the eye. In some instances, the target location is determined based on a preoperative optical coherence tomography (OCT) image, an intra-operative optical coherence tomography (OCT) image, a preoperative optical coherence tomography (OCT) image and an intra-operative optical coherence tomography (OCT) image, or a decision by a surgeon. In some instances, the preoperative OCT image shows Schlemm's canal and networks of collector channels of the eye, and the target location is determined based on the preoperative OCT image. In some instances, the target location is determined based on a microscope-based OCT image, a fiberoptic-based OCT image, or a microscope-based OCT image and a fiberoptic-based OCT image.

In still another aspect, embodiments of the present invention encompass methods of assisting a surgeon to perform a surgical procedure on an eye of a patient. In such procedures, the surgeon may use an elongate probe having a distal end. Exemplary methods include providing a real-time view to the surgeon. The real-time view can include (i) a microscope view of the eye and (ii) an augmented image having the microscope view or a microscope image of the eye. The augmented image may further include an optical coherence tomography (OCT) image of a target tissue region. The OCT image can be registered with the microscope view or the microscope image. The OCT image can enable identification of a target location positioned in the target tissue region. An actual target location may not be visible in the microscope view or the microscope image. The augmented image can enable the surgeon to perceive information regarding a relative position of the distal end of the elongate probe with respect to the target location when the distal end of the elongate probe is not visible in the microscope view or the microscope image.

In some instances, a graphical visual element identifying the target location can be overlaid the microscope view or the microscope image. In some instances, the real-time view includes the augmented image having the microscope view of the eye, the OCT image is registered with the microscope view, the actual target location is not visible in the microscope view, and the augmented image enables the surgeon to perceive information regarding a relative position of the distal end of the elongate probe with respect to the target location when the distal end of the elongate probe is not visible in the microscope view. A graphical visual element can be overlaid the microscope view. According to some embodiments, the real-time view includes the augmented image having the microscope image of the eye, the OCT image is registered with the microscope image, the actual target location is not visible in the microscope image, and the augmented image enables the surgeon to perceive information regarding a relative position of the distal end of the elongate probe with respect to the target location when the distal end of the elongate probe is not visible in the microscope image. A graphical visual element can be overlaid the microscope image.

According to some embodiments, the real-time view includes the augmented image, and the OCT image registered with the microscope view or the microscope image includes information regarding Schlemm's canal and the collector channel system. According to some embodiments, the real-time view includes the augmented image, and the OCT image registered with the microscope view or the microscope image includes information regarding a relative position of the distal end of the elongate probe with respect to the target location. In some instances, a graphical visual element corresponding to the distal end of the elongate probe is overlaid the microscope view or the microscope image, and the information regarding a relative position of the distal end of the elongate probe with respect to the target location is provided by the graphical visual element corresponding to the distal end of the elongate probe and the graphical visual element corresponding to the target location. In some instances, a graphical visual element corresponding to the distal end of the elongate probe and a graphical visual element corresponding to a surface of the trabecular meshwork of the eye are overlaid the microscope view or the microscope image, and the augmented image enables the surgeon to determine whether there is contact between the distal end of the elongate probe and the surface of the trabecular meshwork based on relative positions of the graphical visual element corresponding to the distal end of the elongate probe and the graphical visual element corresponding to a surface of the trabecular meshwork. In some instances, a graphical visual element corresponding to a surface of the trabecular meshwork and a graphical visual element corresponding to a juxtacanalicular trabecular meshwork of the eye are overlaid the microscope view or the microscope image, and the augmented image enables the surgeon to determine whether a trabecular meshwork of the eye is sufficiently compressed based on relative positions of the graphical visual element corresponding to the surface of the trabecular meshwork and the graphical visual element corresponding to the juxtacanalicular trabecular meshwork. In some instances, a graphical visual element corresponding to an inner wall of Schlemm's canal of the eye is overlaid the microscope view or the microscope image, and the augmented image enables the surgeon to determine whether the inner wall of Schlemm's canal has been penetrated based on whether when the graphical visual element corresponding to an inner wall of Schlemm's canal is present in or absent from the microscope view or the microscope image.

According to some embodiments, a guidance arrow is overlaid the microscope view or the microscope image, and the guidance arrow points to the graphical visual element identifying the target location. According to some embodiments, a guidance arrow is overlaid the microscope view or the microscope image, the guidance arrow points to the graphical visual element identifying the target location, and following ablation of the target location, a second guidance arrow is overlaid the microscope view of the microscope image, and the second guidance arrow points to a second graphical visual element identifying a second target location of the eye. In some instances, the real-time view is provided to the surgeon by a display device, a microscope device, a heads up display, a viewing monitor, a virtual reality viewing device, or an augmented reality viewing device. In some instances, a graphical visual element identifying the distal end of the elongate probe is overlaid the microscope view or the microscope image, and the relative position of the distal end of the elongate probe with respect to the target location is based on a relative position of the identifying the distal end of the elongate probe with respect to the graphical visual element identifying the target location. In some instances, the actual target location is not visible in the microscope view or the microscope image due to total internal reflection in the eye. In some instances, the target location is determined based on a preoperative optical coherence tomography (OCT) image, an intra-operative optical coherence tomography (OCT) image, a preoperative optical coherence tomography (OCT) image and an intra-operative optical coherence tomography (OCT) image, or a decision by the surgeon. In some instances, the preoperative OCT image shows Schlemm's canal and networks of collector channels of the eye, and the target location is determined based on the preoperative OCT image.

According to some embodiments, a target location can be determined based on a microscope-based OCT image, a fiberoptic-based OCT image, or a microscope-based OCT image and a fiberoptic-based OCT image. In some instances, methods may further include providing the surgeon with a notification upon detection of sufficient compression of a trabecular meshwork of the eye, where sufficient compression is detected based on relative positions of a graphical visual element corresponding to a surface of the trabecular meshwork and a graphical visual element corresponding to the juxtacanalicular trabecular meshwork. In some instances, methods may also include automatically initiating delivery of laser ablation energy to the actual target location upon detection of sufficient compression of the trabecular meshwork of the eye. In some cases, methods can include providing the surgeon with a notification upon detection of penetration of an inner wall of Schlemm's canal, where penetration of the inner wall of Schlemm's canal is detected by the elongate probe and demonstrated in the real-time view based on whether a graphical visual element corresponding the inner wall of Schlemm's canal is present in or absent from the augmented image. In some cases, methods may include automatically terminating delivery of laser ablation energy to the actual target location upon detection of penetration of an inner wall of Schlemm's canal.

In another aspect, embodiments of the present invention encompass computer program products for aiding a surgeon to perform a surgical procedure on an eye of a patient, for example where the surgeon uses an elongate probe having a distal end. The computer program product can be embodied on a non-transitory tangible computer readable medium. Exemplary computer program products include computer-executable code for generating a real-time view for viewing by the surgeon, where the real-time view includes (i) a microscope view of the eye and (ii) an augmented image having the microscope view or a microscope image of the eye. The augmented image can further include an optical coherence tomography (OCT) image of a target tissue region. The OCT image can be registered with the microscope view or the microscope image. The OCT image can enable identification of a target location positioned in the target tissue region. An actual target location may not be visible in the microscope view or the microscope image. The augmented image can enable the surgeon to perceive information regarding a relative position of the distal end of the elongate probe with respect to the target location when the distal end of the elongate probe is not visible in the microscope view or the microscope image. In some cases, a graphical visual element identifying a target location positioned in the target tissue region is overlaid the microscope view or the microscope image. According to some embodiments, the real-time view includes the augmented image having the microscope view of the eye, the OCT image is registered with the microscope view, the actual target location is not visible in the microscope view, and the augmented image enables the surgeon to perceive information regarding a relative position of the distal end of the elongate probe with respect to the target location when the distal end of the elongate probe is not visible in the microscope view. A graphical visual element can be overlaid the microscope view. According to some embodiments, the real-time view includes the augmented image having the microscope image of the eye, the OCT image is registered with the microscope image, the actual target location is not visible in the microscope image, and the augmented image enables the surgeon to perceive information regarding a relative position of the distal end of the elongate probe with respect to the target location when the distal end of the elongate probe is not visible in the microscope image. The graphical visual element can be overlaid the microscope image.

In some instances, the real-time view includes the augmented image, and the OCT image registered with the microscope view or the microscope image includes information regarding Schlemm's canal and the collector channel system. In some instances, the real-time view includes the augmented image, and the OCT image registered with the microscope view or the microscope image includes information regarding a relative position of the distal end of the elongate probe with respect to the target location. In some instances, a graphical visual element corresponding to the distal end of the elongate probe is overlaid the microscope view or the microscope image, and the information regarding a relative position of the distal end of the elongate probe with respect to the target location is provided by the graphical visual element corresponding to the distal end of the elongate probe and the graphical visual element corresponding to the target location. In some instances, a graphical visual element corresponding to the distal end of the elongate probe and a graphical visual element corresponding to a surface of the trabecular meshwork of the eye are overlaid the microscope view or the microscope image, and the augmented image enables the surgeon to determine whether there is contact between the distal end of the elongate probe and the surface of the trabecular meshwork based on relative positions of the graphical visual element corresponding to the distal end of the elongate probe and the graphical visual element corresponding to a surface of the trabecular meshwork. In some instances, a graphical visual element corresponding to a surface of a trabecular meshwork and a graphical visual element corresponding to a juxtacanalicular trabecular meshwork of the eye are overlaid the microscope view or the microscope image, and the augmented image enables the surgeon to determine whether a trabecular meshwork of the eye is sufficiently compressed based on relative positions of the graphical visual element corresponding to the surface of the trabecular meshwork and the graphical visual element corresponding to the juxtacanalicular trabecular meshwork. In some instances, a graphical visual element corresponding to an inner wall of Schlemm's canal of the eye is overlaid the microscope view or the microscope image, and the augmented image enables the surgeon to determine whether the inner wall Schlemm's canal has been penetrated based on whether when the graphical visual element corresponding to the inner wall of Schlemm's canal is present in or absent from the microscope view or the microscope image.

According to some embodiments, a guidance arrow can be overlaid the microscope view or the microscope image, and the guidance arrow can point to the graphical visual element identifying the target location. In some embodiments, a guidance arrow can be overlaid the microscope view or the microscope image, the guidance arrow can point to the graphical visual element identifying the target location, and following ablation of the target location, a second guidance arrow can be overlaid the microscope view of the microscope image, and the second guidance arrow can point to a second graphical visual element identifying a second target location of the eye. In some instances, the real-time view can be provided to the surgeon by a display device, a microscope device, a heads up display, a viewing monitor, a virtual reality viewing device, or an augmented reality viewing device. In some instances, a graphical visual element identifying the distal end of the elongate probe can be overlaid the microscope view or the microscope image, and the relative position of the distal end of the elongate probe with respect to the target location is based on a relative position of the identifying the distal end of the elongate probe with respect to the graphical visual element identifying the target location. In some cases, the actual target location may not be visible in the microscope view or the microscope image due to total internal reflection in the eye.

According to some embodiments, a target location can be determined based on a preoperative optical coherence tomography (OCT) image, an intra-operative optical coherence tomography (OCT) image, or a preoperative optical coherence tomography (OCT) image and an intra-operative optical coherence tomography (OCT) image. In some cases, a preoperative OCT image can show Schlemm's canal and networks of collector channels of the eye, and the target location can be determined based on the preoperative OCT image. In some cases, a target location can be determined based on a microscope-based OCT image, a fiberoptic-based OCT image, a microscope-based OCT image and a fiberoptic-based OCT image, or a decision by the surgeon. A computer program product can further include computer-executable code for providing the surgeon with a notification upon detection of sufficient compression of a trabecular meshwork of the eye, wherein sufficient compression is detected based on relative positions of a graphical visual element corresponding to a surface of a trabecular meshwork and a graphical visual element corresponding to the juxtacanalicular trabecular meshwork. In some cases, a computer program product can further include computer-executable code for automatically initiating delivery of laser ablation energy to the actual target location upon detection of sufficient compression of the trabecular meshwork of the eye. In some cases, a computer program product can further include computer-executable code for providing the surgeon with a notification upon detection of penetration of an inner wall of Schlemm's canal, where penetration of the inner wall of Schlemm's canal is detected by an elongate probe and demonstrated in a real-time view based on whether a graphical visual element corresponding the inner wall of Schlemm's canal is present in or absent from the augmented image. In some cases, a computer program product can further include computer-executable code for automatically terminating delivery of laser ablation energy to the actual target location upon detection of penetration of an inner wall of Schlemm's canal.

In another aspect, embodiments of the present invention encompass methods of performing a surgical procedure on an eye of a patient, where exemplary methods include viewing a real-time view on a viewing device, where the real-time view includes an augmented image having the microscope view or a microscope image of the eye. The augmented image can further include an optical coherence tomography (OCT) image of a target tissue region. The OCT image can include information regarding Schlemm's canal and the collector channel system and can be registered with the microscope view or the microscope image. In some cases, a graphical visual element identifying a target location positioned in the target tissue region can be overlaid the microscope view or the microscope image. An actual target location may not be visible in the microscope view or the microscope image. Exemplary methods may also include advancing a distal end of an elongate probe within an anterior chamber of the eye toward the target tissue region while viewing the augmented image on the viewing device, where the distal end of the elongate probe is initially visible in the microscope view or the microscope image and thereafter becomes not visible in the microscope view or the microscope image due to total internal reflection in the region of the eye wherein lies the target tissue. Exemplary methods may also include performing the surgical procedure at the actual target location using the elongate probe while the distal end of the elongate probe is not visible in the microscope view or the microscope image, and while perceiving information from the augmented image regarding a relative position of the distal end of the elongate probe with respect to the target location.

In still another aspect, embodiments of the present invention encompass methods of performing a surgical procedure on an eye of a patient, where exemplary methods include viewing a real-time view on a viewing device, where the real-time view includes an augmented image having the microscope view or a microscope image of the eye. The augmented image can further include an optical coherence tomography (OCT) image of a target tissue region. The OCT image can be registered with the microscope view or the microscope image. A graphical visual element identifying a target location positioned in the target tissue region can be overlaid the microscope view or the microscope image. An actual target location may not be visible in the microscope view or the microscope image. Exemplary methods may also include advancing a distal end of an elongate probe within an anterior chamber of the eye toward the target tissue region while viewing the augmented image on the viewing device, the distal end of the elongate probe is initially visible in the microscope view or the microscope image and thereafter becomes not visible in the microscope view or the microscope image due to total internal reflection in the region of the eye wherein lies the target tissue. An OCT image registered with the microscope view or the microscope image can include regarding a relative position of the distal end of the elongate probe with respect to the target location. Exemplary methods may also include performing the surgical procedure at the actual target location using the elongate probe while the distal end of the elongate probe is not visible in the microscope view or the microscope image, and while perceiving the information regarding the relative position of the distal end of the elongate probe with respect to the target location.

In still another aspect, embodiments of the present invention encompass computer systems to assist a surgeon in performing a surgical procedure on an eye of a patient. During the surgical procedure, the surgeon can use an elongate probe having a distal end. Exemplary computer systems can include a processor, an electronic storage location operatively coupled with the processor, and processor executable code stored on the electronic storage location and embodied in a tangible non-transitory computer readable medium. The processor executable code, when executed by the processor, can cause the processor to generate a real-time view for viewing by the surgeon. The real-time view can include (i) a microscope view of the eye and (ii) an augmented image having the microscope view or a microscope image of the eye. The augmented image can further include an optical coherence tomography (OCT) image of a target tissue region. The OCT image can be registered with the microscope view or the microscope image. An actual target location may not be visible in the microscope view or the microscope image. The augmented image can enable the surgeon to perceive information regarding a relative position of the distal end of the elongate probe with respect to the target location when the distal end of the elongate probe is not visible in the microscope view or the microscope image. In some cases, a graphical visual element identifying a target location positioned in the target tissue region can be overlaid the microscope view or the microscope image.

In yet another aspect, embodiments of the present invention encompass a fiber-based apparatuses for performing a surgical procedure in a target tissue region disposed beyond a critical angle of an eye of a patient. Exemplary fiber-based apparatuses can include a sheath, and one or more optical fibers encapsulated by the sheath. The one or more optical fibers can be configured to (i) transmit light energy sufficient to photoablate the target tissue region, and (ii) enable optical coherence tomography (OCT) imaging of the eye. The fiber-based apparatus can be configured perform OCT imaging of the target tissue region along a longitudinal axis of the probe. In some cases, the target tissue region includes a trabecular meshwork, a juxtacanalicular trabecular meshwork, an inner wall of Schlemm's canal of the eye, and Schlemm's canal. In some cases, the fiber-based apparatus configured to transmit the light energy sufficient to photoablate the target tissue region when an OCT scan indicates that a trabecular meshwork of the target tissue region is sufficiently compressed. In some case, the fiber-based apparatus is able to be configured to automatically stop transmission of light energy when an OCT scan indicates that an inner wall of Schlemm's canal has been penetrated. In some cases, the fiber-based apparatus is configured to automatically stop transmission of light energy when an OCT scan indicates that an inner wall of Schlemm's canal has been penetrated. In some cases, the fiber-based apparatus is configured to notify the surgeon to stop transmission of light energy when an OCT scan indicates that an inner wall of Schlemm's canal has been penetrated. In some cases, the fiber-based apparatus is configured to be detected by a microscope-based OCT apparatus. In some cases, the fiber-based apparatus is configured to be detected by a microscope-based OCT apparatus and information processed by both the fiber-based apparatus and the microscope-based OCT apparatus can be displayed so as to enable a surgeon to operate within the target tissue region.

In still another aspect, embodiments of the present invention encompass microscope-based optical coherence tomography (OCT) apparatuses for use in facilitating a surgical procedure in a target tissue region disposed beyond a critical angle of an eye of a patient. Exemplary microscope-based OCT apparatuses may include an OCT unit configured to (i) detect a probe disposed in an anterior chamber of the eye, and (ii) enable OCT imaging of the eye. The microscope-based OCT is configured to perform OCT imaging of the target tissue region. In some cases, the target tissue region includes a trabecular meshwork, a juxtacanalicular trabecular meshwork, an inner wall of Schlemm's canal of the eye, and Schlemm's canal. In some cases, the microscope-based OCT apparatus is configured to detect a fiber-based apparatus. In some cases, the fiber-based apparatus is configured to transmit the light energy sufficient to photoablate the target tissue region when a microscope-based OCT scan indicates that a trabecular meshwork of the target tissue region is sufficiently compressed. In some cases, the fiber-based apparatus is able to be configured to automatically stop transmission of light energy when a microscope-based OCT scan indicates that an inner wall of Schlemm's canal has been penetrated. In some cases, the fiber-based apparatus is configured to automatically stop transmission of light energy when a microscope-based OCT scan indicates that an inner wall of Schlemm's canal has been penetrated. In some cases, the fiber-based apparatus is configured to notify the surgeon to stop transmission of light energy when a microscope-based OCT scan indicates that an inner wall of Schlemm's canal has been penetrated. In some cases, the fiber-based apparatus is configured to be detected by the microscope-based OCT apparatus and information processed by both the fiber-based apparatus and the microscope-based OCT apparatus can be displayed so as to enable a surgeon to operate within the target tissue region.

In still another aspect, embodiments of the present invention encompass computer program products for controlling a microscope-based optical coherence tomography (OCT) apparatus and a fiber-based apparatus during a surgical procedure. The surgical procedure can be performed by a surgeon in a target tissue region disposed beyond a critical angle of an eye of a patient. Exemplary computer program products may include computer-executable code for instructing the microscope-based OCT apparatus to performing OCT imaging of the target tissue region, and computer-executable code for instructing the fiber-based apparatus to performing OCT imaging of the target tissue region along a longitudinal axis of a probe controlled by the surgeon. In some cases, the target tissue region includes a trabecular meshwork, a juxtacanalicular trabecular meshwork, an inner wall of Schlemm's canal of the eye, and Schlemm's canal. In some cases, a computer program product can further include computer-executable code for instructing the fiber-based apparatus to transmit light energy sufficient to photoablate the target tissue region when an OCT scan performed by the fiber-based apparatus indicates that a trabecular meshwork of the target tissue region is sufficiently compressed. In some cases, a computer program product can further include computer-executable code for instructing the microscope-based OCT apparatus to enable the fiber-based apparatus to transmit light energy sufficient to photoablate the target tissue region when an OCT scan performed by the microscope-based OCT apparatus indicates that a trabecular meshwork of the target tissue region is sufficiently compressed. In some cases, a computer program product can further include computer-executable code for instructing the fiber-based apparatus combined with the microscope based OCT apparatus to enable the fiber-based apparatus to transmit light energy sufficient to photoablate the target tissue region when an OCT scan performed by the fiber-based apparatus combined with the microscope-based OCT apparatus indicates that a trabecular meshwork of the target tissue region is sufficiently compressed. In some cases, a computer program product can further include computer-executable code for automatically stopping transmission of light energy when an OCT scan performed by the fiber-based apparatus indicates that an inner wall of Schlemm's canal has been penetrated. In some cases, a computer program product can further include computer-executable code for automatically stopping transmission of light energy when an OCT scan performed by the microscope-based OCT apparatus indicates that an inner wall of Schlemm's canal has been penetrated. In some cases, a computer program product can further include computer-executable code for automatically stopping transmission of light energy when an OCT scan performed by the fiber-based apparatus combined with the microscope based OCT apparatus indicates that an inner wall of Schlemm's canal has been penetrated. In some cases, a computer program product can further include computer-executable code for notifying the surgeon to stop transmission of light energy when an OCT scan performed by the fiber-based apparatus indicates that an inner wall of Schlemm's canal has been penetrated. In some cases, a computer program product can further include computer-executable code for notifying the surgeon to stop transmission of light energy when an OCT scan performed by the microscope-based OCT apparatus indicates that an inner wall of Schlemm's canal has been penetrated. In some cases, a computer program product can further include computer-executable code for notifying the surgeon to stop transmission of light energy when an OCT scan performed by the fiber-based apparatus combined with the microscope based OCT apparatus indicates that an inner wall of Schlemm's canal has been penetrated. In some cases, a computer program product can further include computer-executable code for instructing the microscope-based OCT apparatus to detect the fiber-based apparatus. In some cases, the fiber-based apparatus can be configured to be detected by a microscope-based OCT apparatus and information processed by both the fiber-based apparatus and the microscope-based OCT apparatus can be displayed so as to enable a surgeon to operate within the target tissue region.

In another aspect, embodiments of the present invention encompass treatment methods that include viewing an augmented image on a viewing device, where the augmented image has a microscope view or a microscope image of the eye, and where the augmented image further has an optical coherence tomography (OCT) image of a target tissue region. The OCT image can be registered with the microscope view or the microscope image. The OCT image can enable identification of a target location positioned in the target tissue region, and the target location may not be visible in the microscope view or the microscope image. Related methods may include advancing a distal end of an elongate probe within an anterior chamber of the eye toward the target tissue region while viewing the microscope view or the augmented image on the viewing device, where the distal end of the elongate probe is initially visible in the microscope view or the microscope image and thereafter becomes not visible in the microscope view or the microscope image due to total internal reflection in the eye. Related methods may further include performing the surgical procedure at the target location using the elongate probe while the distal end of the elongate probe is not visible in the microscope view or the microscope image, and while perceiving information from the augmented image regarding a relative position of the distal end of the elongate probe with respect to the target location.

In still another aspect, embodiments of the present invention encompass systems and methods for aiding a physician to perform a surgical procedure on an eye of a patient, where the procedure includes inserting an elongate probe from an opening into the eye across an anterior chamber to a target tissue region of the eye, and where the target tissue region includes a Schlemm's canal and a trabecular meshwork. An exemplary system can include an optical microscope, an optical coherence tomographer, and an image processing apparatus. The image processing apparatus can include a processor, an electronic storage location operatively coupled with the processor, and processor executable code stored on the electronic storage location and embodied in a tangible non-transitory computer readable medium. The processor executable code can include machine-readable instructions that, when executed by the processor, cause the processor to generate an augmented image of the eye. The augmented image can include a microscope image of the eye obtained by the optical microscope, where the microscope image corresponding to an x-y plane of the eye, and where the trabecular meshwork of the target tissue region not visible in the microscope image due to total internal reflection of the trabecular meshwork of the target tissue region (e.g. light reflecting from surface of trabecular meshwork encounters total internal reflection at the cornea). The augmented image can also include an optical coherence tomography image of the target tissue region of the eye, where the optical coherence tomography image is obtained by the optical coherence tomographer, and where the optical coherence tomography image corresponds to an anterior-posterior plane of the eye that is perpendicular to the x-y plane of the eye. The optical coherence tomography image can be in registration relative to the microscope image. The augmented image can further include a graphical visual element overlaid to and in registration with the microscope image. The graphical visual element can be mapped to a radial target location of the target tissue region, and the radial target location can be based on a preoperative optical coherence tomography image or a real-time optical coherence tomography image obtained by the optical coherence tomographer. The augmented image can also include a treatment reference marker overlaid to and in registration with the optical coherence tomography image. The treatment reference marker can be mapped to an anterior-posterior depth target location of the target tissue region and to the radial target location of the target tissue region. The anterior-posterior depth target location can correspond to the Schlemm's canal. In operation, the graphical visual element can aid the physician in advancing a distal end of the elongate probe to the radial target location and the treatment reference marker can aid the physician in advancing the distal end of the elongate probe to the anterior-posterior depth target location. In some cases, the optical coherence tomographer is a microscope-based optical coherence tomographer. In some cases, the optical coherence tomographer is a fiberoptic-based optical coherence tomographer. In some cases, the radial target location is based on the preoperative optical coherence tomography image. In some cases, the radial target location is based on the real-time optical coherence tomography image. In some cases, the radial target location corresponds to a collector channel network of the eye.

In another aspect, embodiments of the present invention encompass systems and methods for generating an augmented image of a target tissue region of an eye of a patient. An exemplary method can include obtaining a microscope image of the eye with an optical microscope, where the microscope image corresponds to an x-y plane of the eye, and where a trabecular meshwork of the target tissue region is not visible in the microscope image due to total internal reflection of the trabecular meshwork of the target tissue region. Methods may also include obtaining an optical coherence tomography image of the eye with an optical coherence tomographer, where the optical coherence tomography image corresponds to an anterior-posterior plane of the eye that is perpendicular to the x-y plane of the eye, and where the optical coherence tomography image is in registration relative to the microscope image. Further, methods can include generating the augmented image with an image processing apparatus, where the image processing apparatus includes a processor, an electronic storage location operatively coupled with the processor, and processor executable code stored on the electronic storage location and embodied in a tangible non-transitory computer readable medium. The processor executable code can include machine-readable instructions that, when executed by the processor, cause the processor to generate the augmented image of the eye. The augmented image can include the microscope image of the eye obtained by the optical microscope, the optical coherence tomography image of the eye obtained by the optical coherence tomographer, and a graphical visual element overlaid to and in registration with the microscope image. The graphical visual element can be mapped to a radial target location of the target tissue region, and the radial target location can be based on a preoperative optical coherence tomography image or a real-time optical coherence tomography image obtained by the optical coherence tomographer. The augmented image can also include a treatment reference marker overlaid to and in registration with the optical coherence tomography image, where the treatment reference marker is mapped to an anterior-posterior depth target location of the target tissue region and to the radial target location of the target tissue region, and where the anterior-posterior depth target location corresponding to a Schlemm's canal of the target tissue region. In some cases, the optical coherence tomographer is a microscope-based optical coherence tomographer. In some cases, the optical coherence tomographer is a fiberoptic-based optical coherence tomographer. In some cases, the radial target location is based on the preoperative optical coherence tomography image. In some cases, the radial target location is based on the real-time optical coherence tomography image. In some cases, the radial target location corresponds to a collector channel network of the eye.

In a still further aspect, embodiments of the present invention encompass computer systems to generate an augmented image of a target tissue region of an eye of a patient. An exemplary computer system includes a processor, an electronic storage location operatively coupled with the processor, and processor executable code stored on the electronic storage location and embodied in a tangible non-transitory computer readable medium. The processor executable code, when executed by the processor, can cause the processor to generate the augmented image of the target tissue region of the eye of the patient. The augmented image can include a microscope image of the eye obtained by an optical microscope, an optical coherence tomography image of the eye obtained by an optical coherence tomographer, and a graphical visual element overlaid to and in registration with the microscope image, where the graphical visual element is mapped to a radial target location of the target tissue region, and where the radial target location is based on a preoperative optical coherence tomography image or a real-time optical coherence tomography image obtained by the optical coherence tomographer. The augmented image can also include a treatment reference marker overlaid to and in registration with the optical coherence tomography image, where the treatment reference marker is mapped to an anterior-posterior depth target location of the target tissue region and to the radial target location of the target tissue region, and where the anterior-posterior depth target location corresponding to a Schlemm's canal of the target tissue region. In some cases, the optical coherence tomographer is a microscope-based optical coherence tomographer. In some cases, the optical coherence tomographer is a fiberoptic-based optical coherence tomographer. In some cases, the radial target location is based on the preoperative optical coherence tomography image. In some cases, the radial target location is based on the real-time optical coherence tomography image. In some cases, the radial target location corresponds to a collector channel network of the eye.

INCORPORATION BY REFERENCE

All publications, patents, patent applications, journal articles, books, technical references, and the like mentioned in this specification are herein incorporated by reference to the same extent as if each individual publication, patent, patent application, journal article, book, technical reference, or the like was specifically and individually indicated to be incorporated by reference.

BRIEF DESCRIPTION OF THE DRAWINGS

The novel features of the invention are set forth with particularity in the appended claims. A better understanding of the features and advantages of the provided system and methods will be obtained by reference to the following detailed description that sets forth illustrative embodiments, in which the principles of the invention are utilized, and the accompanying drawings of which:

FIG. 6A-1 depicts aspects of a patient eye, according to embodiments of the present invention.

FIGS. 6D-1 and 6D-2 depict aspects of registration and/or mapping techniques according to embodiments of the present invention.

FIGS. 7A to 7F-1 show exemplary real and augmented/virtual images as viewed by a surgeon or user during a procedure:

FIGS. 9 to 9-3 show exemplary augmented (virtual) images and augmented (virtual) view obtained using the system in FIG. 8;

FIGS. 12A to 12D-4 show examples of instruments that can be used in combination with the provided system;

DETAILED DESCRIPTION OF THE INVENTION

Figure 1:
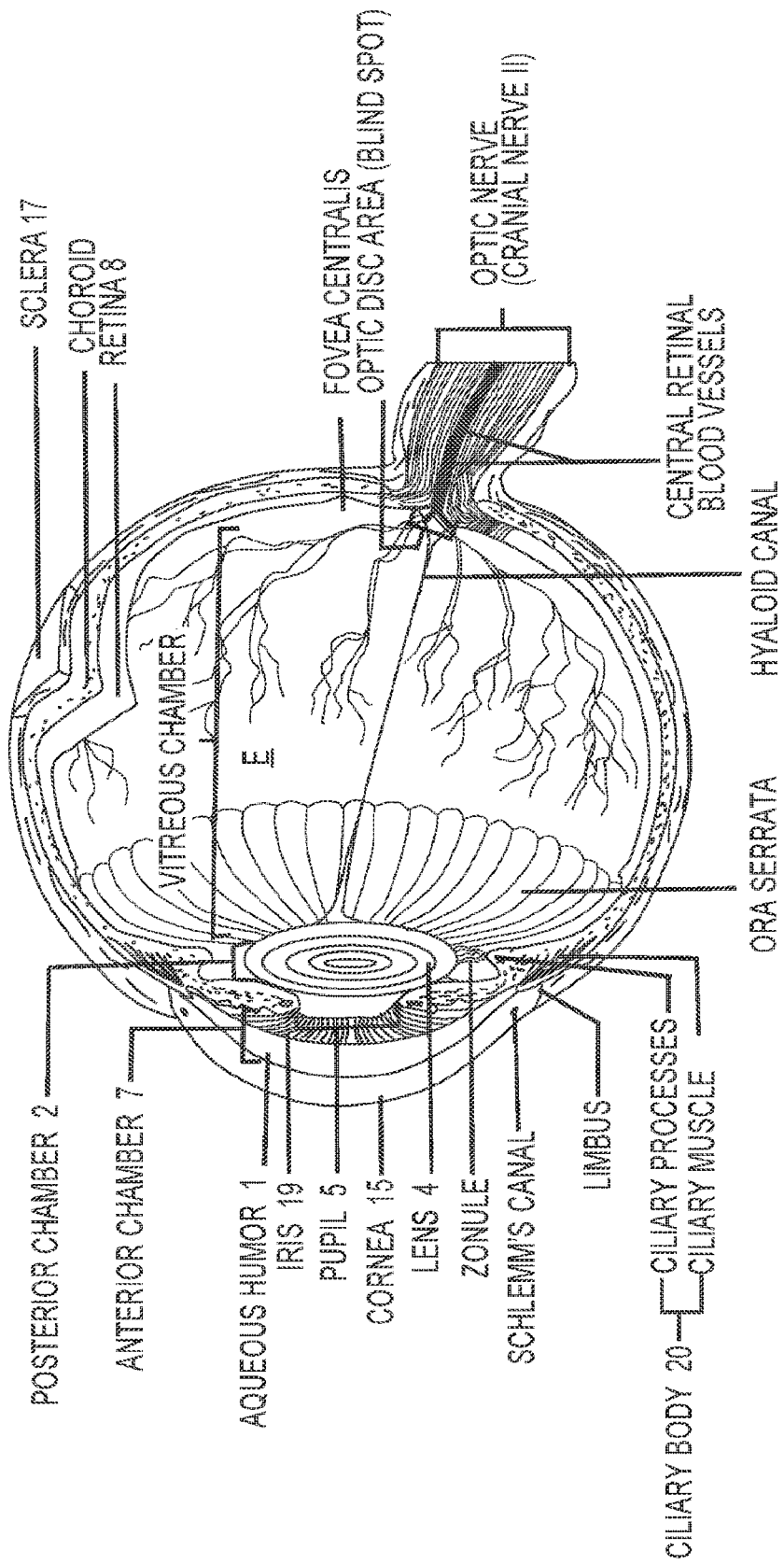
FIG. 1 is schematic sectional view of an eye illustrating anatomical structures.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The methods and apparatuses are well suited for combination with multiple alternative MIGS approaches to treating glaucoma, such as iStent®, iStent Inject, Cypass®, and others, for example. Although reference is made to treatment without a goniolens in some embodiments, the methods and apparatus disclosed herein are also well suited for combination uses with goniolenses.

Methods and systems disclosed herein can allow a larger cohort of ophthalmic surgeons to successfully perform MIGS procedures. For example, the disclosed methods and apparatus can allow for surgeries to more uniformly and consistently create openings to enable improved outflow of aqueous fluid from the eye's anterior chamber into Schlemm's canal, for example. In addition, the disclosed system and methods can lead to improved surgical outcomes, by allowing surgeons to identify target locations for openings into Schlemm's canal intended to increase outflow. In some cases, a target location may include a surface or layer of a tissue, or a position at a tissue, for example of the trabecular meshwork, the juxtacanalicular trabecular meshwork (JCTM), the inner wall of the Schlemm's canal, the outer wall of the Schlemm's canal, the sclera, or desired combinations thereof.

The presently disclosed methods and apparatus may include the combination of a surgical microscope image with sensing devices which enable real-time heads-up display images to be concurrently viewed by the surgeon. These real-time images can allow the surgeon to target and treat locations within an eye which may not be readily visualized using the operating microscope alone, such as structures including the trabecular meshwork and Schlemm's canal. The methods and apparatus disclosed herein can allow a surgeon to view angle structures that are obscured or blocked by total internal reflection. For example, the disclosed methods and apparatus can allow images or information of those otherwise poorly visible or non-visible structures, such as the collector channel system, to be collected using OCT optical coherence tomography (OCT) technologies. A surgeon can concurrently view a real image of the eye with an overlying projected image of ocular structures by the placement of an image of those structures, such as the collector channel system via, for example, an OCT image of the collector channel system obtained earlier which is registered to visible markers, to enable the surgeon to identify and target preferred surgical sites. In this manner, the images viewed by the surgeon include real (optical) and projected (virtual) images combined to enhance surgical targeting. Additional information can also be provided to the surgeon/viewer, such as virtual images of otherwise non-visible structures and one or more symbols to indicate both distances and movement, such as from a probe tip to trabecular meshwork to Schlemm's canal. In some embodiments, OCT imaging can be used to identify collector channels of the eye, and enable the surgeon to identify sites by these target locations (e.g. by using a graphical visual element such as a treatment reference marker to identify a target location) displayed to the user to assist in the creation of openings at appropriate locations in eye's trabecular meshwork to increase flow. Embodiments of the present invention encompass any of a variety of OCT scanning modalities or maps, including pre-operative and/or intra-operative OCT maps or images of the outflow system (e.g. Schlemm's canal and collector channels) such as those depicted in FIGS. 15A to 15C, which can be overlaid onto a microscope image or view. In some cases, one or more OCT images can be used to generate a virtual image of the angle structures, for example as shown in image 610 of FIG. 6. In some cases, one or more OCT images can be used to generate a graphic depiction of the relationships of various structures and the surgical instrument (e.g. fiber/probe), for example as shown in feature 620 of FIG. 6.

Such displays can be coupled to the operating microscope in order to present monocular or binocular virtual images from a display which is visually combined with binocular real optical images of the eye, for example. The methods and apparatus disclosed herein are well suited for utilization with ELT surgery and with implant device surgeries which provide openings to drain fluid from the eye. However, the provided system and methods can also be applied to various other surgical procedures where fiberoptic-based OCT may be utilized, e.g. any and all surgeries using an endoscope.

Although specific reference is made to the treatment of glaucoma using excimer laser trabeculostomy (ELT), the methods and systems disclosed herein can be used with many other types of surgeries. For example, the embodiments disclosed herein can be used with other surgical procedures, including endoscopic procedures relating to orthopedic, neurosurgical, neurologic, ear nose and throat (ENT), abdominal, thoracic, cardiovascular, endocardiac, and other applications. The presently disclosed methods and apparatus can utilize OCT to improve targeting accuracy and provide virtual visualization for enabling surgeons to perform procedures in regions that may not be readily visualized either microscopically or endoscopically. Such applications include any endoscopic procedure in which virtual visualization is augmented to real images to assist surgical accuracy in 3-dimensional space, one example of which is an endovascular procedure in which the vessel curves or bends. Certain aspects may also be used to treat and modify other organs such as brain, heart, lungs, intestines, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone, as well as body lumens and passages such as the sinuses, ureter, colon, esophagus, lung passages, blood vessels, and throat. For example, the devices disclosed herein may be inserted through an existing body lumen, or inserted through an opening created in body tissue.

Devices for performing glaucoma surgery are described in U.S. Pat. Nos. 4,846,172 and 9,820,883, the entire contents of which are herein incorporated by reference.

In order to appreciate the described embodiments, a brief overview of the anatomy of the eye E is provided. As schematically shown in FIG. 1, the outer layer of the eye includes a sclera 17. The cornea 15 is a transparent tissue which enables light to enter the eye. An anterior chamber 7 is located between the cornea 15 and an iris 19. The anterior chamber 7 contains a constantly flowing clear fluid called aqueous humor 1. The crystalline lens 4 is supported and moved within the eye by fiber zonules, which are connected to the ciliary body 20. The iris 19 attached circumferentially to the scleral spur includes a central pupil 5. The diameter of the pupil 5 controls the amount of light passing through the lens 4 to the retina 8. A posterior chamber 2 is located between the iris 19 and the ciliary body 20.

Figure 1A:
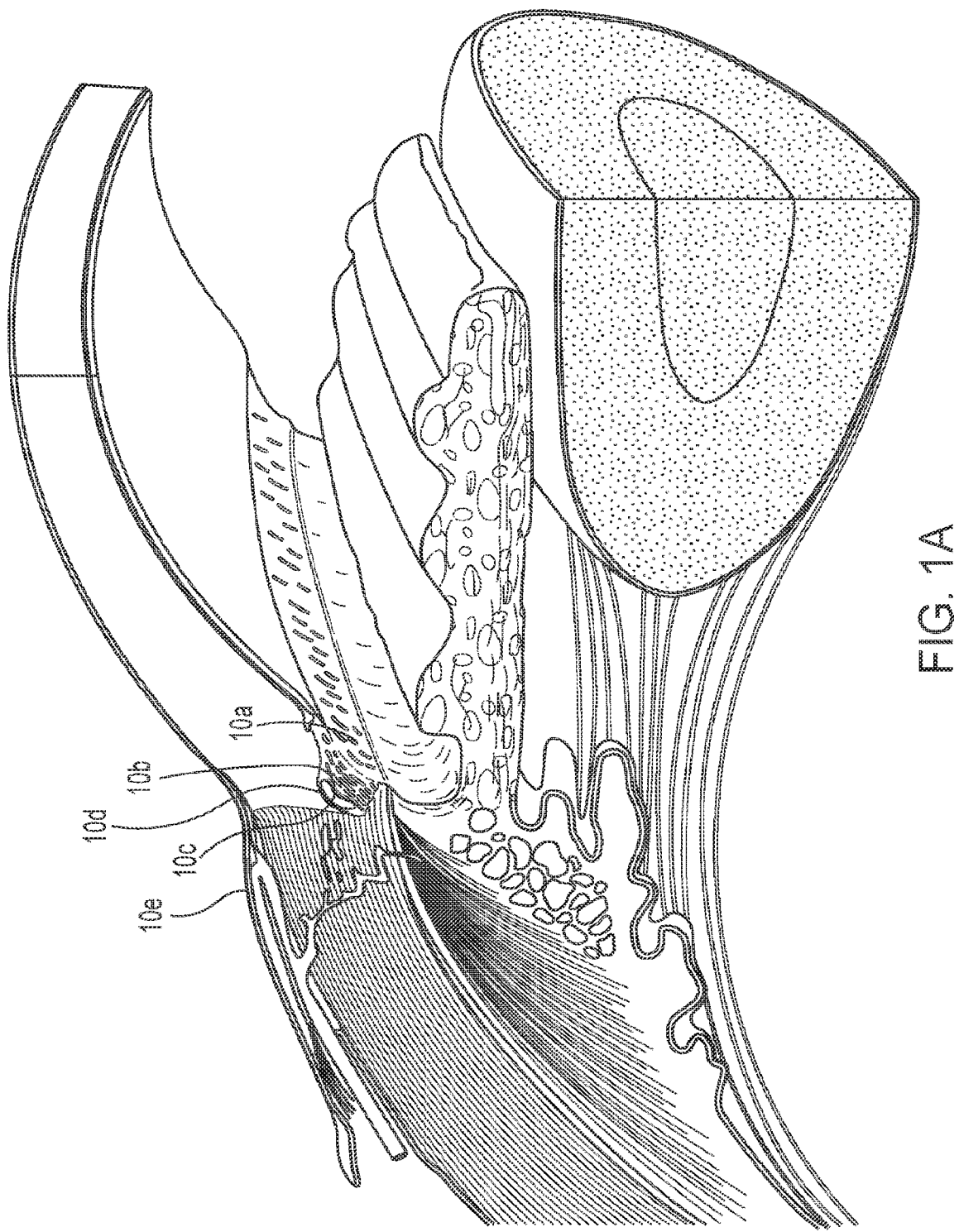
FIG. 1A depicts anatomical aspects of the iridocorneal angle.

FIG. 1A depicts anatomical aspects of the eye at or near the iridocorneal angle. As shown here, the eye includes a trabecular meshwork 10a, a juxtacanalicular trabecular meshwork (JCTM) 10b, an inner wall 10c of Schlemm's canal, an outer wall 10d of Schlemm's canal, and a sclera 10e. Schlemm's canal is represented by the space between inner wall 10c and outer wall 10d.

Figure 2:
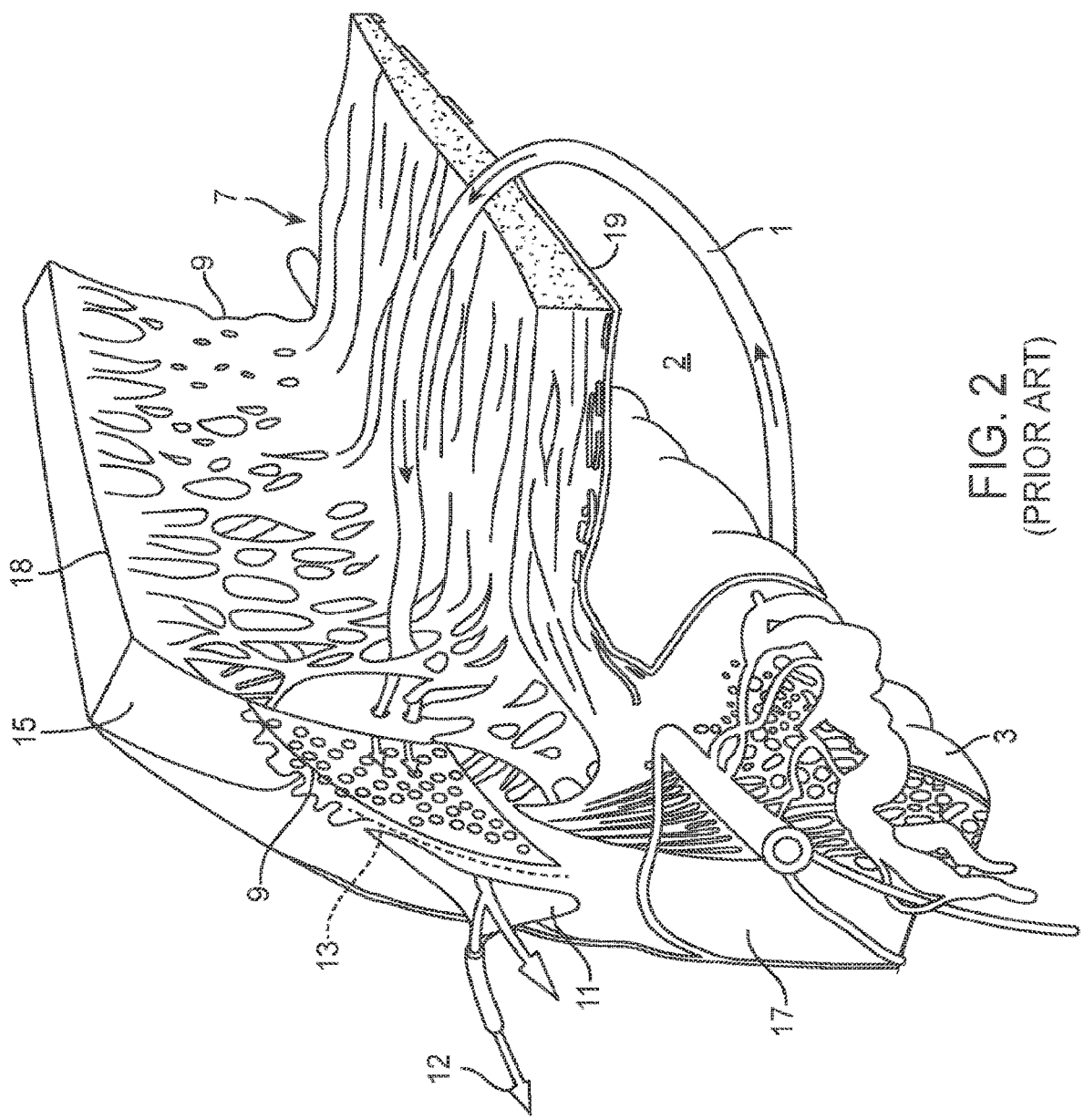
FIG. 2 is a perspective fragmentary view of the anatomy adjacent to the anterior chamber of an eye depicting the corneo-scleral angle and flow of aqueous fluid.

As shown in FIG. 2, the anatomy of the eye further includes a trabecular meshwork (TM) 9, a triangular band of spongy tissue within the eye that lies anterior to the iris 19 insertion to the scleral spur. The mobile trabecular meshwork varies in shape and is microscopic in size. It is generally triangular in cross-section, varying in thickness from about 100-200 µm. It is made up of different fibrous layers having micron-sized pores forming fluid pathways for the egress of aqueous humor from the anterior chamber. The trabecular meshwork 9 has been measured to about a thickness of about 100 µm at its anterior edge, Schwalbe's line 18, at the approximate juncture of the cornea 15 and sclera 17.

The trabecular meshwork widens to about 200 µm at its base where it and iris 19 attach to the scleral spur. The height of the trabecular meshwork can be about 400 µm. The passageways through the pores in trabecular meshwork 9 lead through a very thin, porous tissue called the juxtacanalicular trabecular meshwork 13, which in turn abuts the interior wall of a vascular structure, Schlemm's canal 11. The height of Schlemm's canal can be about 200 µm, or about half the height of the trabecular meshwork. Schlemm's canal (SC) 11 is filled with a mixture of aqueous humor and blood components, and connects to a series of collector channels (CCs) 12 that drain the aqueous humor into the venous system. Because aqueous humor 1 is constantly produced by the ciliary body, and flows through the pupil into the anterior chamber from which it passes through pores in the TM and JCTM into the SC and aqueous veins, any obstruction in the trabecular meshwork, the juxtacanalicular trabecular meshwork, or Schlemm's canal, prevents the aqueous humor from readily escaping from the anterior eye chamber. As the eye is essentially a closed globe, this results in an elevation of intraocular pressure within the eye. Increased intraocular pressure can lead to damage of the retina and optic nerve, and thereby cause eventual blindness.

The obstruction of the aqueous humor outflow, which occurs in most open angle glaucoma (i.e., glaucoma characterized by gonioscopically readily visible trabecular meshwork), is typically localized to the region of the juxtacanalicular trabecular meshwork (JCTM) 13, located between the trabecular meshwork 9 and Schlemm's canal 11, and, more specifically, the inner wall of Schlemm's canal.

When an obstruction develops, for example, at the juxtacanalicular trabecular meshwork 13, intraocular pressure gradually increases over time. Therefore, a goal of current glaucoma treatment methods is to prevent optic nerve damage by lowering or delaying the progressive elevation of intraocular pressure. Many have searched for an effective method of lowering and controlling intraocular pressure. In general, various pharmaceutical treatments have been employed to control intraocular pressure. While these treatments can be effective for a period of time, the intraocular pressure often continues to increase in many patients. However, patients often fail to follow prescribed treatment regimens. As a result, inadequately controlled glaucoma leads to an increased risk of irreversible damage to the optic nerve, and ultimately, vision loss.

Figure 3:
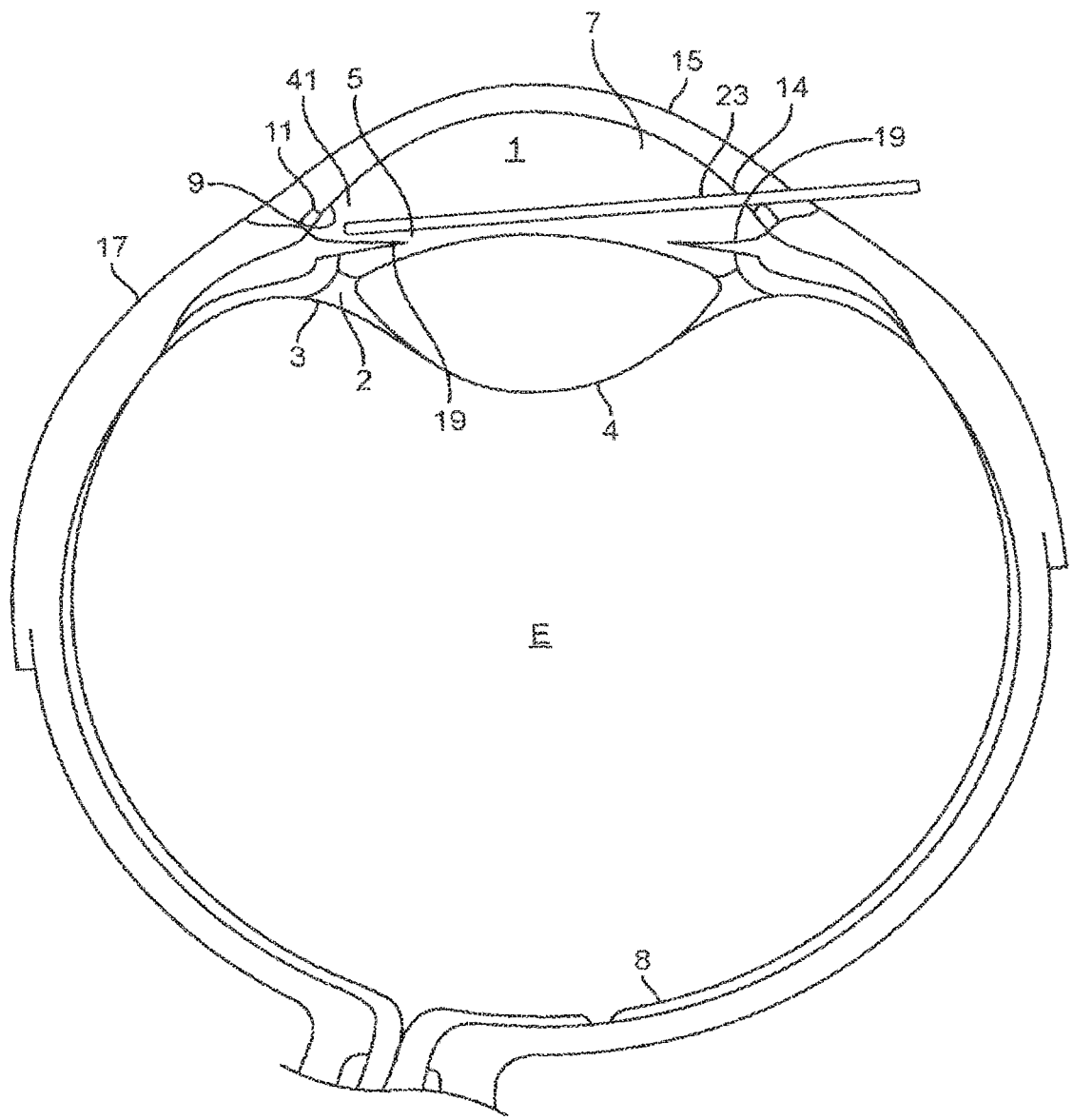
FIG. 3 is schematic sectional view of an eye illustrating a fiber-optic probe crossing the anterior chamber from a corneal limbal paracentesis site toward the trabecular meshwork in the anterior chamber of the eye.

FIG. 3 is a side sectional view of the interior anatomy of a human eye E showing fiber-optic probe 23 in relation to an embodiment of a method of treating glaucoma. After applying topical, peribulbar and/or retrobular anesthesia, a small self-sealing paracentesis incision 14 is created in the cornea 15. The anterior chamber is stabilized with either a chamber maintainer using liquid flows or a viscoelastic agent. Fiber-optic probe 23 can then be positioned and advanced through the incision 14 into the anterior chamber 7 until a distal end of the fiber-optic probe 23 contacts and slightly compresses the desired target TM tissues.

Photoablative laser energy produced by laser unit 31 (shown in FIG. 4) is delivered from the distal end of fiber-optic probe 23 in contact to the tissue to be ablated. The tissue to be ablated may include the trabecular meshwork 9, the juxtacanalicular trabecular meshwork 13 and an inner wall of Schlemm's canal 11. An aperture in the proximal inner wall of Schlemm's canal 11 is created in a manner which does not perforate the distal outer wall of Schlemm's canal. In some embodiments, additional apertures are created in the target tissues. Thus, the resultant aperture or apertures are effective to restore relatively normal rates of drainage of aqueous humor.

The fiber-optic probe 23 may comprise an optical fiber or a plurality of optical fibers encapsulated by an encapsulating sheath. The diameter of a single optical fiber should be sufficiently large to transmit sufficient light energy to effectively result in photoablation of target tissues and in some embodiments to enable OCT imaging of the target tissues. In some embodiments, the optical fiber diameter is in a range from about 4-6 µm. A single optical fiber or a plurality of optical fibers can be used in a bundle of a diameter ranging from about 100 µm to about 1000 µm, for example. Core and sheaths can be encased within an outer metal sleeve, or shield. In some embodiments the sleeve is fashioned from stainless steel. In some embodiments, the outer diameter of sleeve is less than about 100 µm. In some embodiments, the diameter can be as small as 100 µm, as where smaller optical fibers are implemented with laser delivery system. In some cases, the optical fiber may have a diameter of about 200 μm and the fiber-optic probe 23 may have a greater diameter such as 500 μm to encapsulate one or more optical fibers. In some embodiments, the sleeve can be flexible so that it can be bent or angled.

Figure 4:
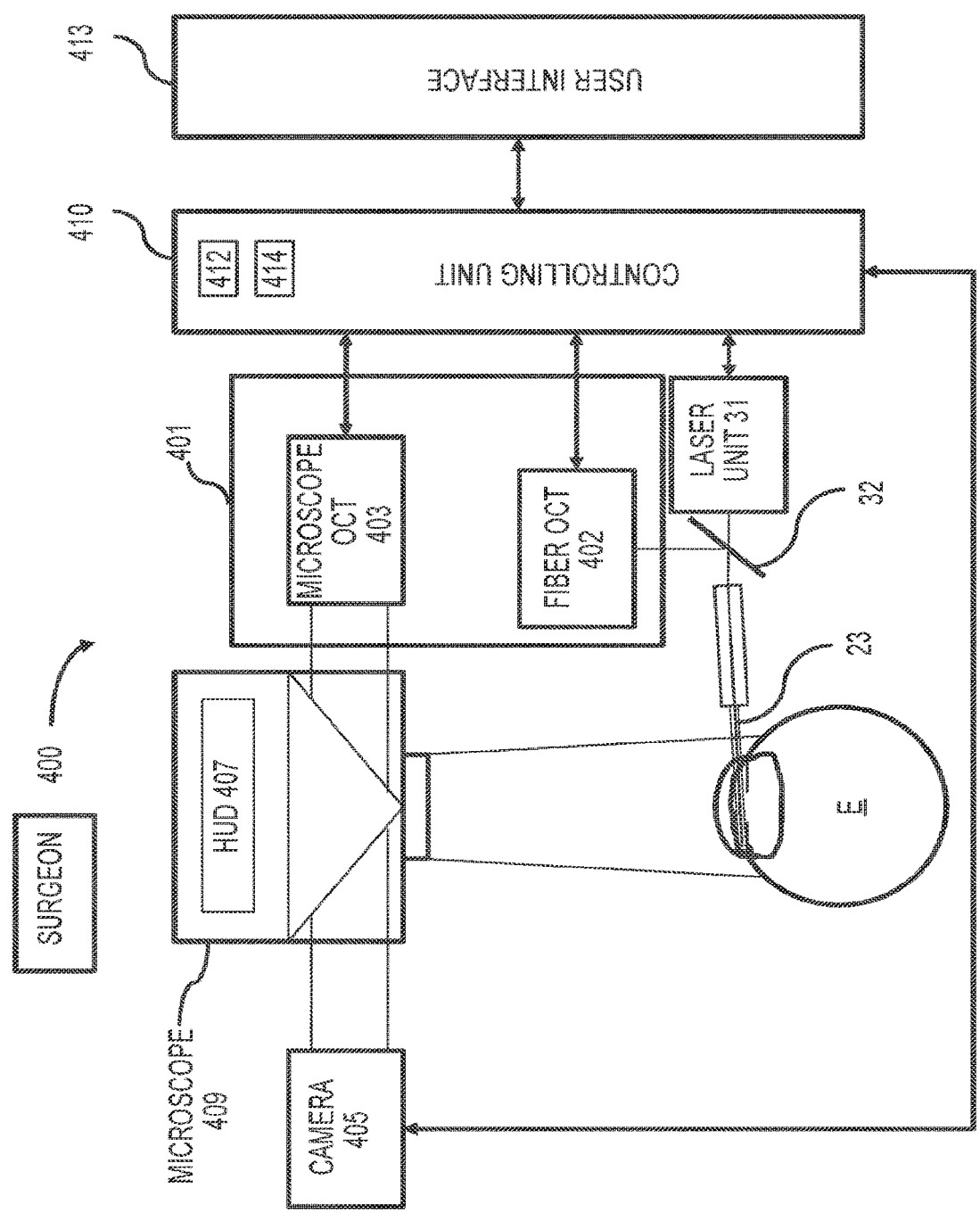
FIGS. 4 and 5 schematically illustrate a system for aiding a physician to perform a surgical procedure on an eye, in accordance with embodiments of the invention.
Figure 5:
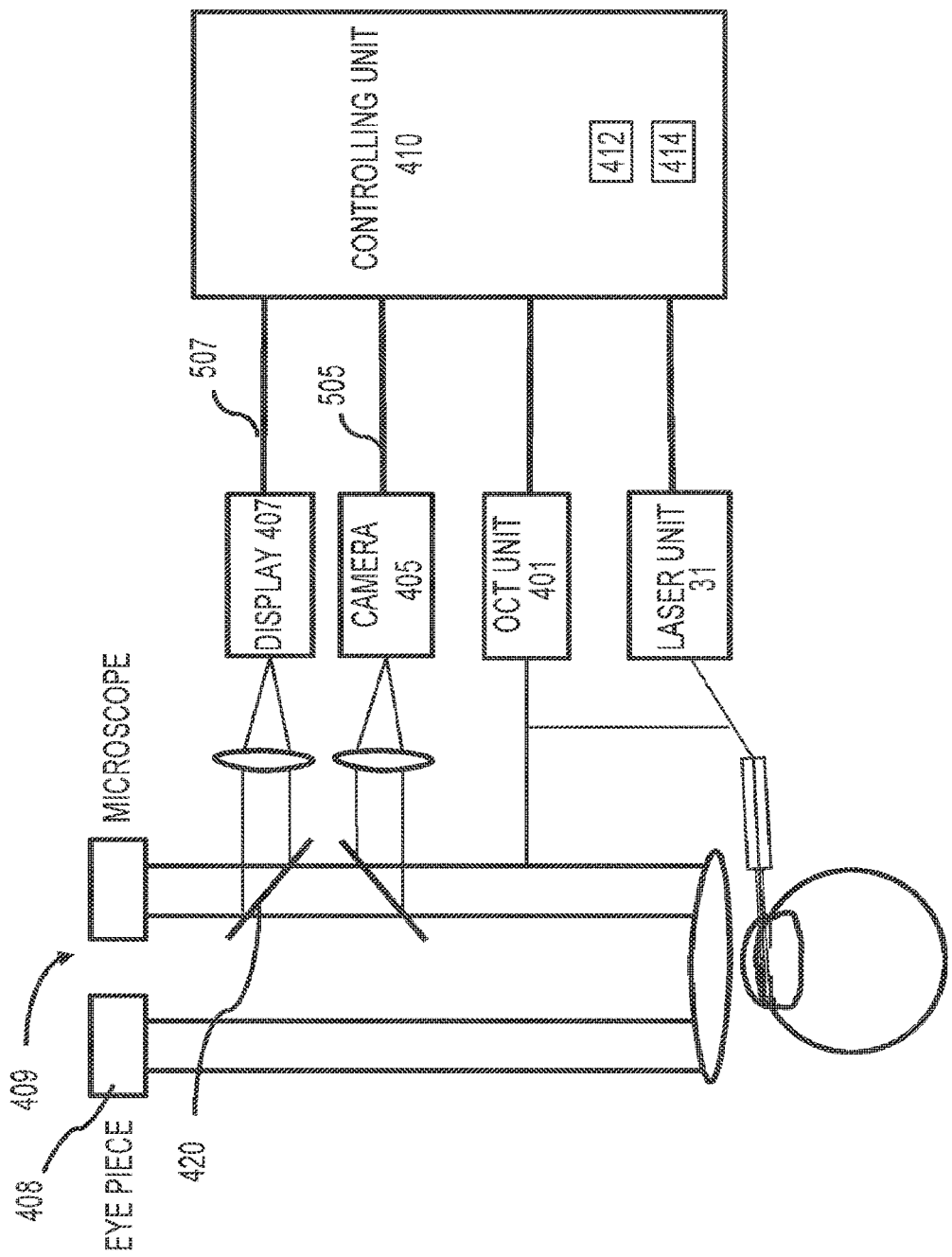

FIG. 4 and FIG. 5 schematically illustrate a system 400 for aiding a physician to perform a surgical procedure on an eye E, in accordance with embodiments of the invention. The surgical operation procedure may comprise inserting an elongate probe 23 from an opening into the eye across an anterior chamber to a target tissue region comprising a trabecular meshwork and a Schlemm's canal. In some embodiments, the system 400 may comprise an optical microscope 409 for the surgeon to view the eye during the procedure in real-time. Integrated within the optical microscope 409 may be an optical coherence tomography (OCT) apparatus. The microscope may comprise a surgical operating microscope, for example. The system 400 may comprise an OCT unit 401 configured to perform an OCT scan of one or more target locations in the target tissue region during the procedure. The OCT unit 401 as described herein may comprise microscope OCT 403 or fiber OCT 402, and combinations thereof, for example. In some cases, an OCT device such as OCT unit 401, microscope OCT 403, and/or fiber OCT 402 can be referred as an optical coherence tomographer. Images captured by the OCT unit 401, microscope OCT 403, and/or fiber OCT 402 may be processed by an image processing apparatus 412 of the controlling unit 410 to generate a plurality of augmented images visualized by the physician in real time. The augmented images can be shown on a display of the heads up display 407, and combined with optical images from the microscope with an internal beam splitter to form monocular or binocular images as is known to one of ordinary skill in the art. As discussed elsewhere herein, a microscope view can include a "real" image, a "real" image and an overlaid virtual image, or an OCT image, for example. When a microscope view includes an overlaid image, the overlaid image can be registered with the "real" image using elements which enable such alignment. According to some embodiments, a surgeon may first view a surgical instrument such as a probe a "real" image in the microscope or a video image from the microscope. In some cases, the surgeon may view an augmented image or view. If there is an OCT overlaid on the "real" image, the surgeon might view both the "real" image and concurrently the overlaid OCT image. The augmented images may be presented to the physician through an eyepiece (or eyepieces) or oculars of the microscope and/or a display of the microscope, and in some configurations may be viewed on a monitor screen. This may be beneficial to allow a surgeon to maintain a stereoscopic view of an operative site through the oculars of the microscope while simultaneously viewing superimposed or adjacent images or information concurrently either stereoscopically or monocularly, for example. OCT scanned real time images, thereby enabling the creation of 3D OCT images and/or OCT-based real time information can be superimposed to the live view of one or both oculars. In some embodiments, the system and method provides a real-time view including real and virtual images from both outside and inside of the anterior chamber during these surgeries.

The optical microscope 409 may be optically coupled with an OCT unit 401. The optical microscope 409 may comprise a binocular microscope such as a stereo-microscope comprising imaging lens elements to image an object onto an eyepiece(s) or ocular 408 and concurrently to a camera 405. The camera 405 is configured to capture optical images 505 of the eye. The optical images 505 may be transmitted to the controlling unit 410 for processing. The camera 405 may comprise optical elements (e.g., lens, mirrors, filters, etc.). The camera may capture color images, greyscale image and the like. In some embodiments, an optical image or view 505 can be obtained by an optical microscope. In some cases, an optical image or view 505 from an optical microscope can be viewable optically from one or more eyepieces of the optical microscope and/or via one or more electronic images created from one or more cameras in the optical pathway of the optical microscope. In some cases, the microscope image or view 505 can correspond to an x-y plane or an iris plane of the eye, while one or more structures of the target tissue region are not visible in the microscope image or view due to total internal reflection in this portion of the eye under observation.

The optical images 505 may be acquired at an appropriate image frame resolution. The image frame resolution may be defined by the number of pixels in a frame. The image resolution can be smaller than or equal to about 160×120 pixels, 320×240 pixels, 420×352 pixels, 480×320 pixels, 720×480 pixels, 1280×720 pixels, 1440×1080 pixels, 1920×1080 pixels, 2048×1080 pixels, 3840×2160 pixels, 4096×2160 pixels, 7680×4320 pixels, 15360×8640 pixels or greater pixel frame, or within a range defined by any two combinations of the preceding pixel ranges. The imaging device or camera may have pixel size smaller than 1 micron, 2 microns, 3 microns, 5 microns, 10 microns, 20 microns and the like. The camera 405 may be, for example, a 4K or higher resolution color camera.

The captured optical images 505 may be a sequence of image frames captured at a specific capture rate. In some embodiments, the sequence of images may be captured at standard video frame rates such as about 24p, 25p, 30p, 48p, 50p, 60p, 72p, 90p, 100p, 120p, 300p or higher, 50i or 60i. In some embodiments, the sequence of images may be captured at a rate less than or equal to about one image every 0.0001 seconds, 0.0002 seconds, 0.0005 seconds, 0.001 seconds, 0.002 seconds, 0.005 seconds, 0.01 seconds, 0.02 seconds, 0.05 seconds. 0.1 seconds, 0.2 seconds, 0.5 seconds, second, 2 seconds, 5 seconds, or 10 seconds. In some cases, the capture rate may change depending on user input and/or external conditions under the guidance of the control unit 410 (e.g. illumination brightness).

The optical images 505 may be captured in real time, such that images are produced with reduced latency, that is, with negligible delay between the acquisition of data and the rendering of the image. Real time imaging allows a surgeon the perception of smooth motion flow that is consistent with the surgeon's tactile movement of the surgical instruments (e.g. the elongate probe and the probe tip) during surgery. Real time imaging may include producing images at rates faster than 30 frames per second (fps) to mimic natural vision with continuity of motion, and at twice that rate to avoid flicker (perception of variation in intensity). In many embodiments, the latency may comprise a time interval from light from the OCT system illuminating the eye until information is shown to the user, and can no more than about 100 ms, for example. In many instances, the latency comprises no more than one or two frames of the image shown on the display. For embodiments comprising A-scan imaging from the distal end of the probe inserted into the eye, the latency can be less than an image frame rate, for example no more than about 10 ms.

In some embodiments, the optical microscope 409 may be coupled to an electronic display device 407. The electronic display 407 may be a heads up display device (HUD). The HUD may or may not be a component of the microscope system 409. The HUD may be optically coupled into the field-of-view (FOV) of one or both of the oculars. The display device may be configured to project augmented images 507 generated by the controlling unit 410 to a user or surgeon. The display device may be coupled to the microscope via one or more optical elements such as beamsplitter or semi-reflection mirror 420 such that a physician looking into the eyepieces 408 can perceive in addition to the real image augmented images represented and presented by the display device 407. The display device may be visible through a single ocular to the surgeon or user. Alternatively, the HUD may be visible through both eyepieces 408 and visible to the surgeon as a binocular image combined with the optical image formed with components of the microscope, for example.

The display device or heads up display 407 is in communication with the controlling unit 410. The display device may project augmented images produced by the controlling unit 410 in real-time to a user. As described herein, real time imaging may comprise capturing the images with no substantial latency, and allows a surgeon the perception of smooth motion flow that is consistent with the surgeon's tactile movement of the surgical instruments during surgery. In some cases, the display device 407 may receive one or more control signals from the controlling unit for adjusting one or more parameters of the display such as brightness, magnification, alignment and the like. The image viewed by a surgeon or user through the oculars or eyepieces 408 may be a direct optical view of the eye, images displayed on the display 407 or a combination of both. Therefore, adjusting a brightness of the images on the HUD may affect the view of the surgeon through the oculars. For instance, processed information and markers shown on the display 407 can be balanced with the microscope view of the object.

The heads up display 407 may be, for example, a liquid crystal display (LCD), a LED display, an organic light emitting diode (OLED), a scanning laser display, a CRT, or the like as is known to one of ordinary skill in the art.

In some embodiments, the HUD 407 may comprise an external display. For example, the HUD may not be perceivable through the oculars in some embodiments. The HUD may be located in close proximity to the optical microscope. The HUD may comprise a display screen, for example. The HUD may comprise a light-emitting diode (LED) screen, OLED screen, liquid crystal display (LCD) screen, plasma screen, or any other type of screen. The display device 407 may or may not be a touchscreen. A surgeon may view real-time optical images of the surgical site and depth information provided by OCTs simultaneously from the HUD.

The OCT unit 401 may be coupled to the optical microscope 409. The OCT unit 401 may comprise a microscope OCT unit 403, a fiberoptic-based OCT unit 402 or a combination of both. The OCT unit 401 can comprise swept source OCT (SS-OCT), spectral domain OCT (SD-OCT), Fourier domain OCT (FD-OCT), or time domain OCT (TD-OCT), as known for OCT systems in the art. The OCT system may comprise a suitable resolution for viewing tissue structures of the eye such as Schlemm's canal and/or collector channels and may comprise a resolution within a range from less than 1 to 10 microns, for example within a range from about 3 to 6 microns, for example. The OCT unit 401 may comprise a low-coherence light source suitable for producing OCT image information and interferometric information. The OCT unit 401 may produce OCT images with depth information and transmit the OCT images to the controlling unit 410. The OCT unit may be at least partially controlled by the controlling unit. Control of the OCT unit by the controlling unit may include, for example, activation of an OCT scan, parameters set-up, or customizable control parameters.

The OCT unit may comprise a microscope OCT unit 403. The microscope OCT unit 403 may comprise a component of the optical microscope 409 or share components with the optical microscope. In some cases, the microscope OCT unit 403 may comprise a stand-alone OCT unit adapted for such use. The microscope OCT unit may be positioned at a distance from the eye without contacting the eye. The microscope OCT unit may be operably coupled to the optical microscope. The microscope OCT unit may utilize one or more optical elements of the optical microscope such as the objective lens. The microscope OCT unit 403 may be compatible with the optical microscope system 409. For instance, the microscope OCT unit 403 may be configured to allow for real-time adjustment of the OCT focal plane to maintain parfocality with the microscope view. In another instance, the microscope OCT unit 403 may be capable of adapting to changes in the optical power of one or more optical elements of the optical microscope, such as the magnification of lenses such as the objective lens or other lenses of the microscope. Microscope OCT unit 403 may be configured to acquire OCT images using an engine (e.g., SDOCT engine) with a light source (e.g., NIR light source) and a detector (e.g., line-scan CCD). Depending on the different types of OCT, different spectrometers such as CCD or photodiode array detector may be used. The microscope OCT unit 403 may be configured to produce OCT images as an A-scan, B-scan or C-scan depending on the scanning principles. For instance, by performing a fast Fourier transform (FF), an axial scan (i.e., A-scan) as a function of depth can be reconstructed. By moving a mirror in x direction, a succession of A-scan lines is created, which can be stacked together to create a B-scan image or two-dimensional image. By moving the mirror in both x-y directions, a full three-dimensional volume image or C-scan image (3D) can be generated. The mirror can be coupled to any suitable actuator known to one of ordinary skill in the art, such as a galvanometer, a translation stage, a MEMs actuator or a piezoelectric crystal, for example. In some embodiments, the microscope OCT unit 403 may be activated to acquire B mode images to provide information about a position of a probe relative to a target location along the anterior and posterior plane of the eye. In some cases, the microscope OCT unit 403 may perform C-scan to generate three-dimensional image of the target tissue region.

The OCT unit may comprise a fiberoptic-based OCT unit 402. According to some embodiments, the terms "fiberoptic-based OCT unit" and "fiber-based apparatus" may be used interchangeably. The fiberoptic-based OCT unit 402 may comprise an optical fiber or an array of optical fibers to direct laser light pulses internal to the eye structure and to capture images of the internal eye structures. The fiberoptic-based OCT unit may perform OCT imaging while also delivering laser light pulses. The optical fiber can be inserted within the eye and in contact with tissue inside the eye. In some embodiments, the optical fiber can be the same fiber used in the fiber optical probe 23 to transmit laser light. Alternatively, the optical fiber may be a separate fiber such as a standard single mode or multi-mode optical fiber. The separate fiber may be housed in the same fiber optic probe 23. For instance, the optical fiber may be encapsulated in an encapsulating sheath of the probe 23 that the encapsulating sheath is configured to stiffen the single optical fiber. This enables precise identification of a position of the tip of the probe 23 relative to Schlemm's canal, TM and the other target tissues. In some embodiments, a separate optical fiber for returning the back-scattered signal to the corresponding detector may be employed. A dichroic mirror 32 may be used to deflect the back-scattered signal to the detector. In some embodiments, the optical fiber of the OCT unit and the fiber-optic probe may be coaxial functioning as a coaxial endoscope for identifying a position of the distal end of the probe relative to target tissues. Alternatively, the optical fiber may be non-coaxial with the fiber-optic probe. In some cases, a probe may include an array of OCT detection fibers positioned around a treatment fiber.

The fiberoptic-based OCT unit 402 may be configured to generate axial scan images (A-Scan image). This may be beneficial to provide real time information about the relative position of the distal end of the probe with respect to the target site or target location. The A-scan images may be acquired at a high frequency such as in a range of 10 Hz to 5 kHz. The A-scan images may be processed by the controlling unit 410 to generate an image comprising a plurality of position or distance markers corresponding to a plurality of positions of target tissues and the probe tip. In some cases, a plurality of A-scan images may be averaged to generate an image for improved accuracy. The image from the A-scan(s) may be superimposed to the optical image to provide position information of the fiber optical tip relative to target tissues along the axial direction of the probe.

The system 400 may further comprise a user interface 413. The user interface 413 may be configured to receive user input and output information to a user. The user input may be related to control of a surgical tool such as the probe 23 operation. The user input may be related to the operation of the optical microscope (e.g., microscope settings, camera acquisition, etc.). The user input may be related to various operations or settings about the OCT unit. For instance, the user input may include a selection of a target location, a selection of a treatment reference marker, displaying settings of an augmented image, customizable display preferences and the like. The user interface may include a screen such as a touch screen and any other user interactive external device such as handheld controller, mouse, joystick, keyboard, trackball, touchpad, button, verbal commands, gesture-recognition, attitude sensor, thermal sensor, touch-capacitive sensors, foot switch, or any other device.

In some embodiments, a microscope-based OCT 403 is used for guiding the probe 23 and visualization. In some embodiments, a fiberoptic-based OCT 402 is used for guiding the probe 23 and visualization. In some embodiments, both of the microscope-based OCT and fiberoptic-based OCT are employed in the system and used for guiding the probe 23 and visualization. The microscope-based OCT and the fiberoptic-based OCT may perform OCT scans along one or more planes of the eye. In some cases, when both of the OCTs are employed, the microscope-based OCT may be configured to perform a first OCT scan along an anterior-posterior plane of the eye and the fiberoptic-based OCT may be configured to perform a second OCT scan along an axis transverse to the anterior-posterior plane. In some cases, either of the microscope-based OCT and fiberoptic-based OCT may be used independently.

The microscope-based OCT and the fiberoptic-based OCT may or may not comprise similar scan resolutions. In some cases, the microscope-based OCT may perform a scan with higher scan resolution than the fiberoptic-based OCT. For instance, a B-scan performed by the microscope-based OCT may have a higher resolution than an A-scan performed by the fiberoptic-based OCT. Alternatively, a scan resolution of the fiberoptic-based OCT may be higher than the microscope-based OCT. The axial resolution may be determined based on the bandwidth of the source spectrum. The scan resolution may be determined to provide a fast enough frame rate to ensure real-time feedback. The resolution of each of the OCT systems can be within ranges as described herein.

The microscope-based OCT and the fiberoptic-based OCT may or may not have the same frame/scan rate. In some cases, the microscope-based OCT performs B-scan and the fiberoptic-based OCT performs A-scan, and need not require a volume scan of the surgical site. This can provide real-time position feedback at a higher rate. The frame rate of the cross-section view provided by the microscope-based OCT and the axial view provided by the fiberoptic-based OCT may be influenced by various factors such as the size of the scanning field, resolution or scanning rate. In some cases, the two-dimensional OCT images (B-scan) obtained by the microscope-based OCT may be used to provide a coarse position of the probe relative to a target tissue or target location, in which case relatively high resolution and slow frame rate may be sufficient. In some cases, the axial scan image (A-scan) obtained by the fiberoptic-based OCT may provide fine and precise position of the distal end of the probe relative to a small sized structure (e.g., SC, CC, TM), thus higher frame rate may be desired. In some cases, high frame rate may be desired to minimize motion artifacts and enhance image quality. For instance, the axial scan of the fiberoptic-based OCT may have one dimensional A-scan frame/scan rate of at least 100 fps, or greater with a structural image resolution within a range from about 1 micron to about 20 microns, for example. In many embodiments, the A-scan frame rate is within a range from about 1 kHz to about 10 kHz. The OCT system can be configured to measure tissue while contacting the probe tip and up to a distance of at least about 10 mm from the probe tip, for example at least about 6 mm from the probe tip. These distances enable the probe tip to target Schlemm's canal from a range of up to 6 mm in distance from the target site or target location. In some embodiments, the OCT apparatus may comprise a phase-based OCT configured to detect a motion of the distal end of the elongate probe, for example motion in a range from about 20 nm to about 1 μm.

The system may provide surgeons augmented information overlaid to live view of optical images of a surgical site. This is beneficial to reduce disruptions in surgical procedures by allowing surgeons to view supplemental information without moving their eyes away from the microscope's viewing optics or a heads up display. The augmented information may comprise a magnified field view of various areas of the eye on which they are operating. The augmented information may comprise depth view comprising position information of the probe relative to a target tissue. The augmented information may comprise a navigate direction of an elongated probe. The augmented information may be provided to a surgeon in substantially real-time. The augmented information may comprise real time OCT images. The augmented information may comprise a plurality of visual graphical elements generated based on real time OCT images and/or static OCT images. The terms "visual graphical element" and "graphical visual element" may be used interchangeably throughout this application. The augmented information may comprise still and/or moving images and/or information (such as text, graphics, charts, plots, and the like) to be overlaid into an operating microscope surgical viewing field or an optical microscope image displayed on a screen.

In some cases, the augmented information may be overlaid or superimposed to an optical image obtained by an optical microscope to form an augmented image. The augmented image may be displayed on a screen either such as the heads up display, a separate viewing monitor or both. In some cases, the augmented information may be overlaid over direct optical path image such that the viewing field visible to a surgeon through the oculars of the microscope comprises both the optical path image and the overlaid augmented information. In some cases, the augmented information may be superimposed to the optical image in a picture-in-picture format.

The controlling unit 410 may be configured to generate an augmented layer comprising the augmented information. The augmented layer may be a substantially transparent image layer comprising one or more graphical elements. The terms "graphical element" and "graphical visual element" may be used interchangeably throughout this application. The augmented layer may be superposed onto the optical view of the microscope, optical images or video stream, and/or displayed on the display device. The transparency of the augmented layer allows the optical image to be viewed by a user with graphical elements overlay on top of it. In some embodiments, the augmented layer may comprise real time OCT images or other information obtained by an OCT unit coupled to the optical microscope.

As described above, the fusing of the optical microscopic image data and the augmented information may comprise incorporating the augmented information into the optical microscopic image. The augmented image data may comprise one or more graphical elements associated with the depth information, target location and various other supplemental information. The graphical elements may be overlaid onto the optical microscopic image with a beam splitter, for example. A graphical element can be directly overlaid onto an image of any object visible in the optical microscopic image. A graphical element may also include any shape, boundary, or contour surrounding an image of any object in the optical microscopic image. The object may be, for example, an instrument inserted into the eye (e.g., probe), a portion of the probe, target tissues (e.g., SC, CC, TM, JCTM, sclera), and the like.

In some embodiments, the graphical elements may be configured to dynamically change as a position or an orientation of the probe or instrument changes relative to a target location. For example, a graphical element may indicate a location of a distal end of the probe shown in the optical image, or relative location or spacing between tissues such as inner wall of SC, TM and the like. The graphical elements may be configured to dynamically show the change in spacing between the tissue walls or distance between the tip and a target location substantially in or near real-time on the optical image, as the relative distance between the probe tip and a target location changes, and/or when the probe tip compresses on tissue (e.g., surface of trabecular meshwork).

In some embodiments, the augmented information may comprise an orientation of the probe relative to the target location. The graphical elements may indicate the orientation of the probe relative to the target location. The graphical elements may be configured to dynamically show the orientation of the probe relative to the target location substantially in or near real-time on the optical image, as the orientation between the probe and the target location changes. In some instances, a graphical element may indicate an orientation or axial location of the elongated probe. To indicate orientation (e.g., direction), the graphical element may be provided in the form of an arrow. The arrow may be configured to change dynamically based on movement/advancing of the probe.

The augmented layer or at least some of the graphical elements can be mapped or matched to the optical image using object recognition techniques or pattern matching techniques, such as feature point recognition. A feature point can be a portion of an image (e.g., scleral landmarks, collector channel patterns, iris landmarks, etc.) that is uniquely distinguishable from the remaining portions of the image and/or other feature points in the image. A feature point may be detected in portions of an image that are relatively stable under perturbations (e.g., when varying illumination and brightness of an image).

Figure 6:
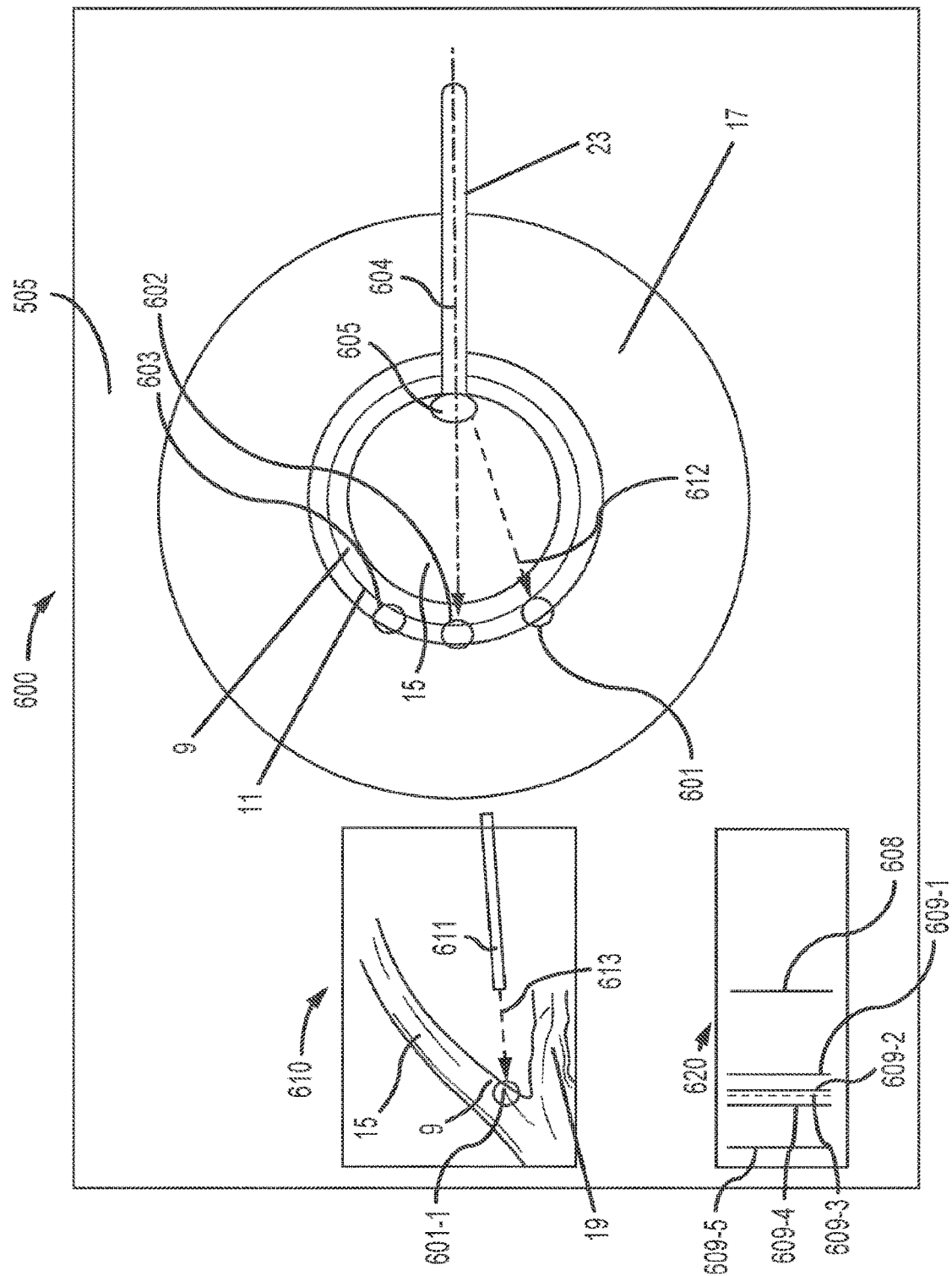
FIG. 6 illustrates both real images of the eye and fiber-optic probe and an exemplary augmented (virtual) image and augmented (virtual) view.

FIG. 6 illustrates an exemplary augmented image or augmented view 600. As described above, the augmented image 600 may be viewed binocularly by a user or surgeon through oculars of the microscope, and may be displayed on a heads up display, an external display device, or a display coupled to a user interface. The augmented image or view may comprise an optical image 505 or an optical path view through the oculars of an optical microscope. The optical image 505 may comprise a top-down view of the eye. The optical image or optical view may show anterior of an eye. The optical image or optical view may further show an elongated probe 23. According to some embodiments, probe 23 may include any of the fiber-optic probe structures or perform any of the fiber-optic probe functions described in U.S. Pat. No. 8,679,089, the contents of which are incorporated herein by reference. The augmented image or view 600 may comprise a plurality of graphical visual elements and one or more OCT images adjacent to or overlaid over the optical image, for example by optically coupling the display to the optical path of the microscope with a beam splitter. The plurality of graphical visual elements may comprise different shapes and/or colors corresponding to different objects such that different objects shown in the optical image can be easily distinguished from one another. As shown here, the optical image or view 505 can correspond to an x-y plane of the eye, or an iris plane of the eye. In some cases, optical image or view 505 is substantially parallel with an x-y plane of the eye or an iris plane of the eye. According to some embodiments, a substantially parallel optical image or view 505 is sufficiently parallel to the x-y plane or iris plane of the eye so as to enable the surgeon to adequately visualize the anatomical structures of interest within the anterior chamber when performing the surgical procedure.

In some embodiments, reference number 600 may refer to an augmented microscope view, reference number 505 may refer to a microscope image, reference number 610 may refer to a computer-generated image based on OCT information, and reference number 620 may refer to a graphical representation of OCT data. Relatedly, an augmented microscope view 600 may include a microscope image 505, a computer generated image based on OCT information obtained from an optical coherence tomographer, a graphical visual element overlaid to and in registration with the microscope image, where the graphical visual element is mapped to a radial target location of the target tissue region, and the radial target location based on a preoperative optical coherence tomography image or a real-time optical coherence tomography image obtained by the optical coherence tomographer. The augmented microscope view may also include a treatment reference marker overlaid to and in registration with the computer-generated image based on OCT information, where the treatment reference marker is mapped to an anterior-posterior depth target location of the target tissue region and to the radial target location of the target tissue region, and the anterior-posterior depth target location corresponds to a Schlemm's canal of the target tissue region.

The plurality of graphical visual elements may comprise one or more treatment reference markers 601, 602, 603 mapped to the one or more target locations. As discussed elsewhere herein, treatment reference markers 601, 602, 603 may correspond to target locations which are not optically visible to the surgeon in the optical image or optical path view 505. According to some embodiments, target locations may be located ab interno, and treatment of the target locations may involve an ab interno approach. In some cases, the one or more target locations may be determined or identified based on a preoperative OCT image.

As discussed elsewhere herein, preoperative and/or intraoperative OCT images may be obtained using either ab interno approaches and/or ab externo approaches. In some cases, microscope images may be obtained using ab externo approaches. According to some embodiments, a treatment reference marker or target location can be selected based on a location in the target tissue region that would provide a significant increase in outflow following the formation of a channel therethrough (e.g. channel passing through the trabecular meshwork, the juxtacanalicular trabecular meshwork, and the inner wall of Schlemm's canal, thus providing fluid communication between the anterior chamber and Schlemm's canal). Such a selection can be based on an identification of certain regions in collector channel networks or fields that are more dense, or that contain larger vessels, or a larger distribution of vessels, or that are less obstructed, or that correspond to circumferential flow areas provided by Schlemm's canal. During real time optical imaging, the one or more treatment reference markers 601, 602, 603 may be superimposed to the target locations by detecting a pattern of the target location identified from the preoperative OCT image (e.g., one or more specific collector channels). In some cases, a user or surgeon may be prompted to select a target location(s) or treatment reference marker(s) through the user interface 413. In some cases, a user or surgeon may be prompted to rank or order selected target locations for treatment. Hence, the user or surgeon can specify a desired sequence in which the target locations will be treated during the surgical procedure. For example, the user or surgeon can specify that treatment reference marker 601 corresponds to a target location that will be treated first, that treatment reference marker 602 corresponds to a target location that will be treated second, and that treatment reference marker 603 corresponds to a target location that will be treated third. As discussed elsewhere herein, for example with reference to FIGS. 15A to 15C, treatment reference markers can be selected based on locations (e.g. locations in a target tissue region) that have been determined to correspond to bigger collector channels, more dense collector channel networks or fields, and/or and greater outflow. In some cases, the treatment reference markers can be selected in an automated fashion. In some cases, the treatment reference markers can be selected manually. Systems can be configured to guide the surgeon to direct the laser fiber to each of the selected treatment reference markers, sequentially. In some cases, a plurality of treatment reference markers may be shown simultaneously such as in the beginning of a procedure for a user to select a target location. In some cases, the plurality of treatment reference markers may be shown sequentially as the surgical operation progresses. According to some embodiments, treatment reference markers 601, 602, and/or 603 can represent one or more radial target locations (e.g. distance relative to center or pupil of the eye).

The plurality of graphical visual elements may also comprise a probe line 604 coaxial with the elongate probe 23. The probe line 604 shows an orientation of the probe in relation to the one or more target locations. The plurality of graphical visual elements may also comprise a distal tip marker 605 overlapping with the distal end of the elongated probe. Both the probe line and the distal tip marker may dynamically change locations with respect to the actual positions and orientation of the elongate probe shown in the optical image or view 505, as the probe is moved within the anterior chamber of the eye. Hence, for example, a surgeon can use microscope to see the probe 23 as it enters the anterior chamber, and can watch the probe as it moves relative to the eye. An OCT detection mechanism can detect the probe 23, and an automated system or processor can generate the probe line 604 in response to the detection. Similarly, the automated system or processor can generate the guidance arrow 612.

Figure 15A:
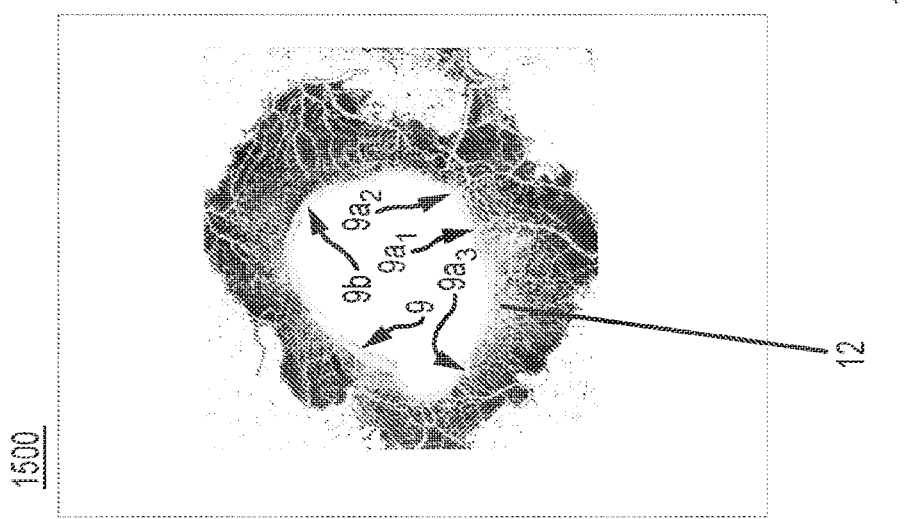
FIGS. 15A to 15C show examples of pre-operative OCT images, and augmented pre-operative OCT images showing collector channels and target locations.
Figure 15B:
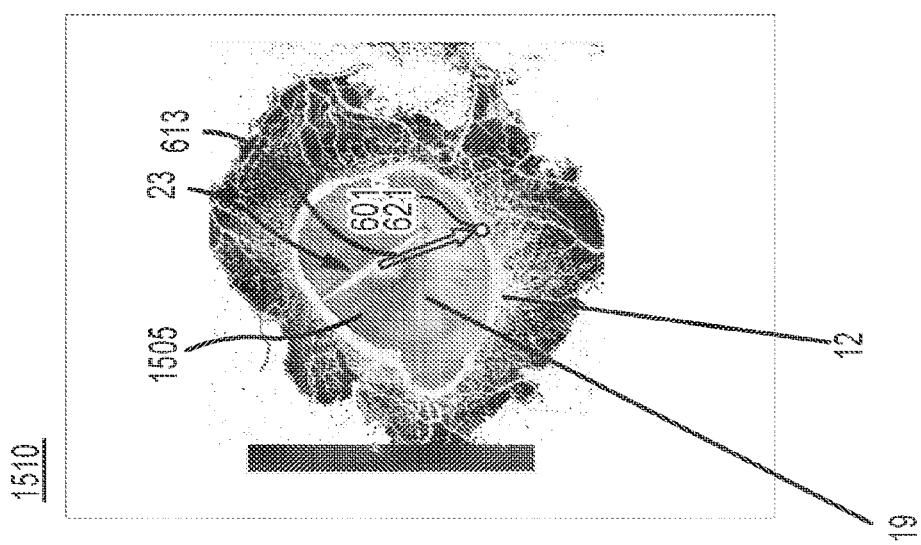
Figure 15C:
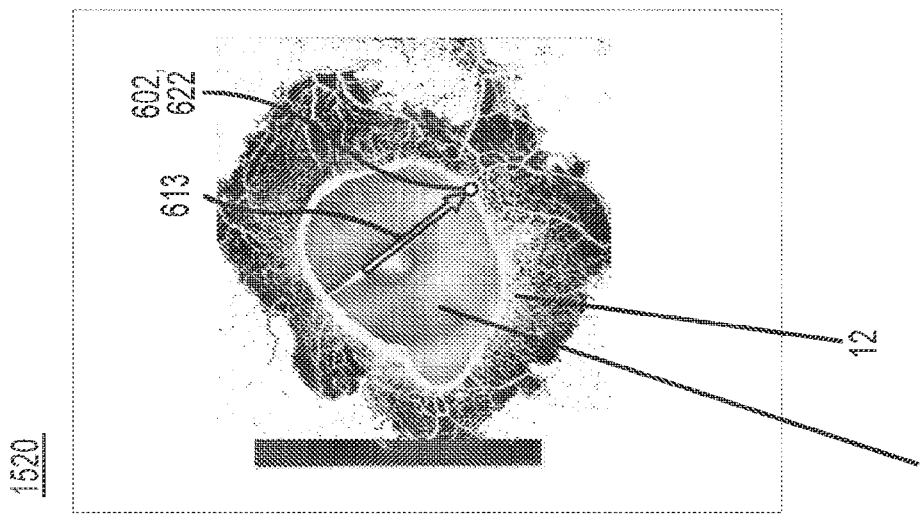

The plurality of graphical visual elements may further comprise one or more guidance arrows or markers 612 extending from the distal tip marker 605 towards the one or more treatment reference markers (e.g., marker 601). The one or more guidance arrows 612 may be configured to guide the physician in aligning the distal end of the elongate probe to point towards the one or more target locations during the procedure, or guide the physician in advancing the elongate probe towards the one or more target locations during the procedure. As discussed elsewhere herein, the one or more target locations may not be optically visible to the surgeon in the optical image or optical view 505. For example, upon a selection of a target location, a guidance arrow 612 may be generated pointing from the distal end of the probe (or the distal tip marker 605) to the selected target location (or the corresponding treatment reference marker) such that the physician may advance the probe parallel or coaxial to the guidance arrow. The one or more guidance arrows 612 may point radially from within the anterior chamber in different directions toward the target tissue region comprising the trabecular meshwork and the Schlemm's canal. As discussed elsewhere herein, the height of Schlemm's canal may be about half the height of the trabecular meshwork. In some cases, the one or more guidance arrows may automatically appear when the distal end of the probe is located at a predetermined distance away from the target location, for example when the distal end of the probe is located about 6 mm or less from the target location. Alternatively, the one or more guidance arrows may appear in response to a user input indicating a target location selected from the plurality of target locations. Although the guidance arrow 612 in FIG. 6 is depicted as originating from a location that is distal along the probe 23, it is appreciated that in some embodiments, a guidance arrow can originate from a location that is more proximal along the probe, for example as shown in FIGS. 15B and 15C. In some cases, the guidance arrow can provide an alignment indication to the surgeon, so that the surgeon may co-linearly align the probe with the guidance arrow.

The augmented layer may further comprise one or more OCT images overlaid to the optical image. The OCT image or OCT-based image may provide depth information or position of the probe relative to a target location in a plane extending in a direction transverse to the optical image plane, for example substantially perpendicular to the optical image plane. According to some embodiments, a substantially perpendicular OCT image plane is sufficiently perpendicular to the optical image plane so as to enable the surgeon to adequately visualize the anatomical structures of interest within the anterior chamber while performing the surgical procedure. In some cases, an OCT image or OCT-based image that provides the depth information and/or the position of the probe relative to the target location in the plane extending in a direction transverse to the optical image plane is obtained by a microscope OCT apparatus (e.g. overhead OCT apparatus). In some cases, an OCT image or OCT-based image that provides the depth information and/or the position of the probe relative to the target location in the plane extending in a direction transverse to the optical image plane is obtained by a fiberoptic OCT apparatus. In some embodiments, one or more magnified field views may be generated based on OCT images 610, 620. For example, the OCT-based image may be magnified by at least two to five times as compared to the optical image. For instance, as illustrated in FIG. 6, a two-dimensional OCT image 610 obtained by the microscope OCT is overlaid on the optical image 505. In some cases, the scan used to generate image 610 is performed intraoperatively. The terms "microscope OCT" and "microscope-based OCT" may be used interchangeably throughout this application. As shown here, the OCT image 610 can correspond to a longitudinal or anterior-posterior plane of the eye, and the longitudinal or anterior-posterior plane can be substantially perpendicular to an x-y plane of the eye or an iris plane of the eye. The two-dimensional OCT images 610-4, 610-5, 610-6, 610-7, and 610-8 as described elsewhere herein may comprise embodiments, variation, or examples of the two-dimensional OCT image 610 and may comprise substantially similar characteristics. For example, one or more of these images may be generated based on an intraoperative scan. In some cases, the OCT image 610 may comprise a B-scan image. Alternatively or in combination, the OCT image 610 may be a three-dimensional image (C-scan). In some cases, real time or substantially real-time OCT images may be displayed overlying the optical image in a picture-within-picture format. Alternatively or in combination, information derived from the OCT image may be overlaid to the optical image. In some embodiments, when the distal end of the probe is within a predetermined distance to the selected target location, a microscope-based OCT scan may be performed to produce the two-dimensional OCT image 610. The microscope based OCT scan may extend along a plane defined by the present target location, e.g. the target location corresponding to treatment reference marker 601, and an opening into the eye, e.g. a small incision into the cornea (paracentesis) as described herein.

The two-dimensional image 610 may comprise a B-scan OCT image and one or more visual graphical elements. The B-scan OCT image may comprise a density plot, for example. The horizontal axis may correspond to the direction of transverse scanning and the vertical axis may correspond to the scanning depth. A gray level can be plotted at a particular pixel on the OCT image corresponding to the magnitude of the depth profile at a particular depth and transverse scanning position. The B-scan OCT image may be post-processed by the image processing apparatus of the controlling unit 410 for image enhancement, image compression or the like. In some cases, the two-dimensional image 610 may be generated by averaging a plurality of B-scan OCT images such that the two-dimensional image may be updated at a lower rate than the acquisition frame rate of the B-scan OCT images. Alternatively, the two-dimensional image 610 may be updated at the same frame rate as the acquisition frame rate of the B-scan OCT images.

The B-scan OCT image may be obtained along an OCT image plane along the elongate axis of the probe 23. The B-scan OCT image plane can be aligned with the probe line 604 along an anterior-posterior plane of the eye. For instance, the probe axis may be determined by an analysis of the optical image acquired with the video, and the microscope-based OCT is controlled to align the OCT image plane with the elongate axis of the probe. The microscope OCT plane can be displayed to the user with a line extending along the probe axis with the line being shown on the display and optically coupled to the microscope image.

In some cases, the two-dimensional OCT scan (B-scan) may be performed automatically in a region where the probe line intersects at least one treatment reference markers. The OCT scan region may comprise the anterior-posterior plane of the eye along the probe elongate axis. The OCT scan region may comprise a portion of the anterior-posterior plane such as including a portion of the distal end of the probe and the region in front of the probe. The OCT scan region may not comprise the entire length of the probe. In some cases, the two-dimensional OCT scan may be performed automatically upon detecting that the probe line is substantially aligned coaxially with the one or more guidance arrows and oriented towards the one or more treatment reference markers. In some cases, the two-dimensional OCT scan may be performed automatically upon detecting that the distal end of the elongate probe is at a predefined distance from a target location. For example, the predefined distance can be within a range from about 1 mm to 6 mm.

The two-dimensional OCT image 610 may further comprise a plurality of graphical visual elements overlaid onto OCT image. For instance, one or more treatment reference markers 601-1 may be mapped to the target location in the OCT image. As discussed elsewhere herein, an OCT image may or may not be overlaid with a graphical visual element. In some cases, a graphical visual element can be separate from an OCT image and not overlying it. According to some embodiments, an OCT image may be overlying a microscope image. For example, an OCT image can be overlying a microscope image via a microscope, a display, or a microscope combined with a display. The plurality of graphical visual elements may also comprise a probe marker 611 indicating at least the position of the probe tip with respect to the target location corresponding to treatment reference marker 601-1 in the depth cross-section. This provides the physician depth information, thus guiding the physician in adjusting the advancing direction of the probe in the anterior-posterior plane of the eye (i.e., depth). In some embodiments, a guidance arrow 613 may also be overlaid to the OCT image for guiding the probe movement towards the target location, for example whereby the surgeon can visualize probe marker 611 advancing along guidance arrow 613 toward treatment reference marker 601-01. In some cases, probe marker 611 may indicate or identify the orientation of an elongate axis of the probe, for example with respect to the target location corresponding to treatment reference marker 601-1. In some cases, the probe marker 611 can be coaxial with the elongate axis of the probe.

In some cases, the two-dimensional OCT image 610 may provide information about another OCT scan. For instance, based on the relative position information between the probe tip and a target tissue location, a fiberoptic-based OCT scan may be activated and graphical elements may be overlaid to the OCT image 610 indicating the scan range (e.g., arrows 614 in FIG. 7C) of the fiberoptic-based OCT scan. The scan range may be in a range such as from 1 degree to 45 degrees. Alternatively, the fiberoptic-based OCT scan may comprise an A-scan.

The fiberoptic-based OCT scan can be performed by the fiberoptic-based OCT unit 402 as described above. The fiberoptic-based OCT scan may be performed along the probe line 605 along an axis of the eye. The fiberoptic-based OCT unit 402 may be configured to automatically perform the OCT scan upon detecting that the distal end of the elongate probe is at a second predefined distance from the target location. The second predefined distance may be within a range, for example, from about 1 mm to about 6 mm. In some cases, the fiberoptic-based OCT scan may be performed after the microscope-based OCT scan. In some cases, the fiberoptic-based OCT scan may be performed independent of the microscope-based OCT scan. In an example, the fiberoptic-based OCT scan may be activated when the probe line is detected to be aligned with the guidance arrow either in the x-y plane identified by the optical image or in the cross-section plane identified by the microscope-OCT image, or a combination of both. Alternatively, the fiberoptic-based OCT scan may be activated manually.

In some embodiments, an image 620 or other information based on the fiberoptic-based OCT scan may be generated and overlaid onto the optical image in a picture-within-picture like format. In some cases, the scan used to generate image 620 is performed intraoperatively. In some embodiments, the image 620 may be generated by the microscopic OCT. The image 620 may or may not comprise the fiberoptic-based OCT image. The image 620 may be positioned close to the tip of the probe. The image 620 can be positioned in any location within the optical view or on the augmented image. The OCT images 620-5, 620-6, 620-7, 620-8, 620-9, 620-90, and 620-91 as described elsewhere herein (e.g. FIGS. 7D-F and 9) may comprise embodiments, variation, or examples of the OCT image 620 and may comprise substantially similar characteristics. For example, one or more of these images may be generated based on an intraoperative scan.

The image 620 may comprise a plurality of graphical visual elements 608, 609-1, 609-2, 609-3, 609-4, 609-5 generated based on the fiberoptic-based OCT scan or microscope-based OCT scan. In some embodiments, the fiberoptic-based OCT scan is performed between a distal end of the elongate probe and a target location to generate an OCT A-scan of the target location comprising a portion of the trabecular meshwork and the Schlemm's canal. The plurality of graphical visual elements may comprise one or more A-scan distance markers 608, 609-1, 609-2, 609-3, 609-4, and 609-5. The A-scan distance markers may provide a magnified distance view of the relative position between the probe tip and tissue structures. The A-scan distance markers enable the physician to observe the distal end of the elongate probe when the distal end is no longer visible in the images collected by the optical microscopic apparatus, and also aid the physician in guiding the distal end of the elongate probe towards the target location and also guide the surgeon regarding applying compression to the trabecular meshwork. In some cases, the A-scan distance markers may be generated when the distal end of the elongate probe is no longer visible in the microscope image as a result of the distal end of the elongate probe being obscured due to total internal reflection of the corner near an iridocorneal angle of the eye. According to some embodiments, a distance marker (e.g. 608, 609-1, 609-2, 609-3, 609-4, and/or 609-5) can represent a radial target location (e.g. distance relative to center or pupil of the eye). In some cases, a radial target location may also be referred to as a radial depth target location, where, for example, the radial depth corresponds to the radial distance from the center of the eye or the radial distance from the center of the pupil. In some cases, the location of a distance marker (e.g. 608, 609-1, 609-2, 609-3, 609-4, and/or 609-5) can correspond to a distance from a corneal paracentesis incision through which an elongated probe can be inserted through and into the anterior chamber of the eye.

The A-scan distance markers may comprise a plurality of graphical visual elements showing relative distances between one or more of a distal end of the elongate probe (identified by distance marker 608), surface of the trabecular meshwork (identified by 609-1), juxtacanalicular trabecular meshwork (JCTM) (identified by distance marker 609-2), an inner wall of the Schlemm's canal (identified by distance marker 609-3), an outer wall of the Schlemm's canal (identified by distance marker 609-4), or sclera (identified by distance marker 609-5). According to some embodiments, the distance markers 609-2 and 609-3 may be so close together as to be indistinguishable, as the JCTM is a very thin membrane and is situated adjacent the inner wall of Schlemm's canal. It is appreciated that the inner wall of Schlemm's canal is balloon-like and mobile, whereas the outer wall of Schlemm's canal is fixed or adhered to the firm sclera and relatively immobile, and that the size of Schlemm's canal can depend on relative pressures and contents within the canal. In FIG. 6 the graphical elements are shown as lines and circles, however any other shapes or colors can be used to mark the relative distances. The plurality of lines may comprise different colors, patterns, or thicknesses. The plurality of lines may be visually distinguishable from one another. The A-scan distance markers are overlaid onto the microscope image of the eye. The microscope image shows a top-down view of the eye, and the A-scan distance markers show a magnified axial view of the target location. In some cases, the axial view of the target location is magnified by at least two to five times.

As illustrated in FIG. 6, the plurality of graphical visual elements may comprise a first line or distance marker 608 corresponding to the distal end of the elongate probe, a second line or distance marker 609-1 corresponding to the surface of the trabecular meshwork, a third line or distance marker 609-2 corresponding to the juxtacanalicular trabecular meshwork (JCTM), a fourth line or distance marker 609-3 corresponding to the inner wall of the Schlemm's canal, a fifth line or distance marker 609-4 corresponding to the outer wall of the Schlemm's canal, and a sixth line or distance marker 609-5 corresponding to the sclera, for example. Any number of lines or markers may be generated depending on the specific tissue structure. One or more of the graphical visual elements may move relative to each other to reflect the real-time relative position of the corresponding objects. For instance, the first line 608 may appear to move relative to each of the second through sixth lines as the distal end of the elongate probe advances towards the target location. The plurality of lines allows the physician to know where the distal end of the elongate probe is located relative to the surface of the trabecular meshwork, the JCTM, the inner wall of the Schlemm's canal, the outer wall of the Schlemm's canal, and the sclera. The plurality of lines allows the physician to advance the distal end of the elongate probe in a precise manner toward the target location comprising the trabecular meshwork and the inner wall of the Schlemm's canal. In some cases, the plurality of lines allows the physician to advance the distal end of the elongate probe to apply gentle compression on the trabecular meshwork, thereby avoiding over-compressing the trabecular meshwork. In some case, compression of the trabecular meshwork reduces the thickness of the trabecular meshwork to about 90 microns, for example from an original thickness of approximately 150 microns. In some cases, the plurality of lines allows the physician to know whether the inner wall of the Schlemm's canal has been penetrated, and to avoid penetrating the outer wall of the Schlemm's canal. For instance, when the inner wall of the Schlemm's canal has been penetrated, the lines 609-2 and 609-3 may disappear from the augmented image indicating the probe tip has passed the inner wall of the SC (or that the inner wall of SC has otherwise been penetrated), and in some cases, the physician may retract the elongate probe once the inner wall of the Schlemm's canal has been penetrated. The laser firing may automatically stop upon detection of penetration of the inner wall of Schlemm's canal, for example. In some cases, when the inner wall of the SC is penetrated, a next target location may be shown in the images to inform the surgeon where to aim the probe next to create another ablation channel in the inner wall of the Schlemm's canal, in the manner as described above. The target information may be generated from a fiber-optic A-scan of the new target location. Additionally or optionally, the target information may be generated from a microscope B-scan of the new target location.

As noted above, penetration of the inner wall of Schlemm's canal can be indicated by disappearance of line 609-3, which is a graphical visual element (e.g. A-scan distance marker) corresponding to the inner wall of Schlemm's canal. In some cases, embodiments of the present invention are configured so that line 609-3 disappears from image 620 when the probe tip penetrates the inner wall of Schlemm's canal. According to some embodiments, it can be assumed that the probe tip does not significantly move once the trabecular meshwork is compressed and laser pulses initiated. In some cases, embodiments of the present invention are configured so that line 609-3 disappears from image 620 when laser pulses penetrate the inner wall of Schlemm's canal. In some cases, embodiments of the present invention are configured so that line 609-3 disappears from image 620 when ablated tissue structures distal to the probe tip are converted to gas and enter Schlemm's canal. According to some embodiments, laser pulses can penetrate the inner wall of Schlemm's canal, or the gas ablation product can enter Schlemm's canal, while the probe tip does not penetrate into Schlemm's canal. According to some embodiments, an ablation channel can be created by ablation of the trabecular meshwork, the juxtacanalicular trabecular meshwork, and the inner wall of Schlemm's canal, so as to form an aperture. Compression of the trabecular meshwork can be monitored by evaluating the distance between line 609-1 corresponding to the surface of the trabecular meshwork and line 609-2 corresponding to the juxtacanalicular trabecular meshwork (JCTM). According to some embodiments, penetration of the inner wall of Schlemm's canal can be monitored by evaluating the distance between distance markers, which can be A-scan distance markers, such as the distance between line 609-3 and line 609-4. For example, as the inner wall of Schlemm's canal is penetrated and gas enters Schlemm's canal, a localized and transient expansion of Schlemm's canal may occur (e.g. as a result of the incoming gas), and the distance between the inner and outer walls of Schlemm's canal may increase. At some time following penetration, as Schlemm's canal is collapsed, the distance between the inner and outer walls of Schlemm's canal may decrease (e.g. from an initial distance of about 200 microns when the canal is expanded to a subsequent distance of about 20 microns when the canal is collapsed.

Figure 6A:
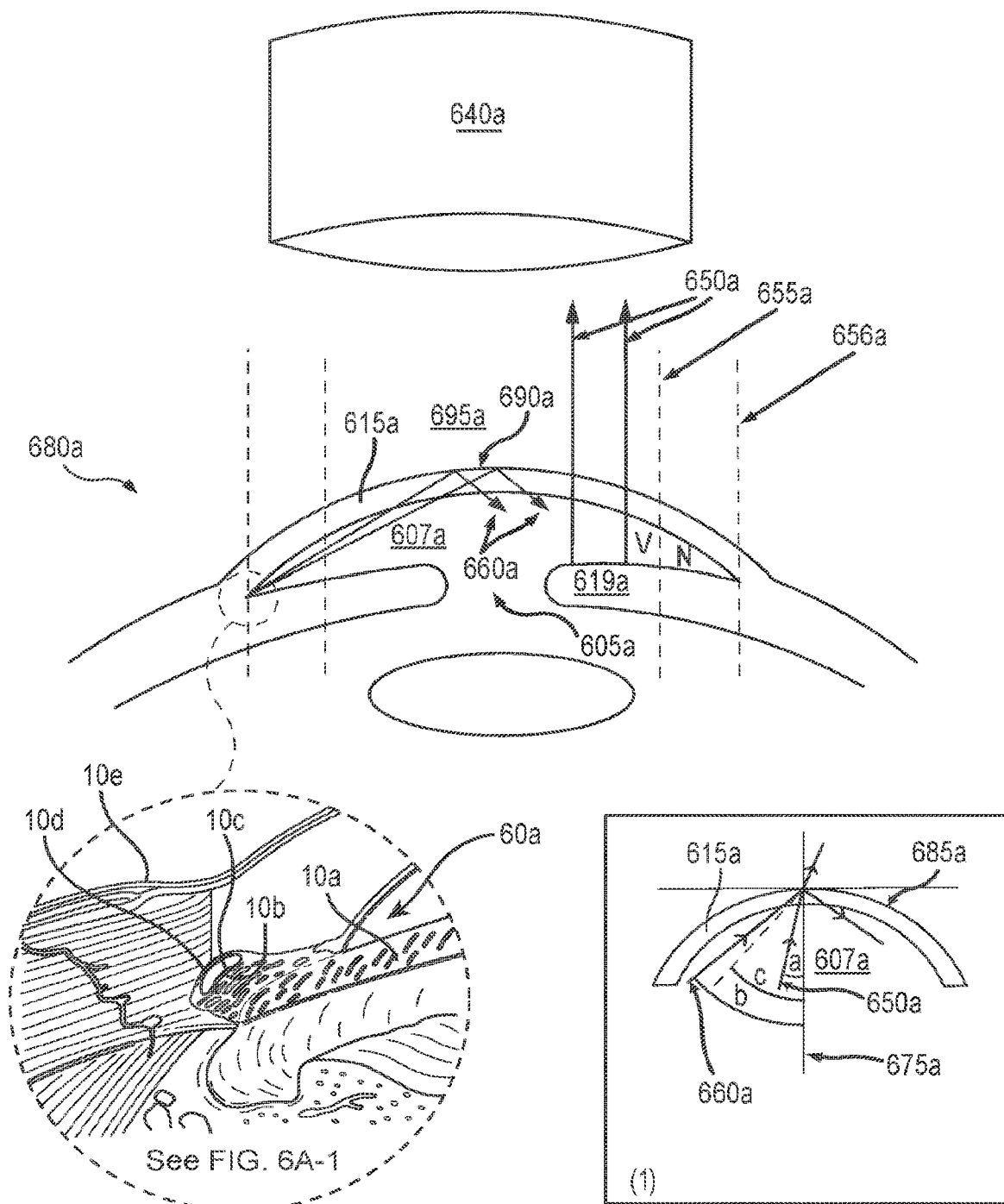
FIG. 6A depicts aspects of a patient eye and an optical device, according to embodiments of the present invention.
Figures 1, 6A:
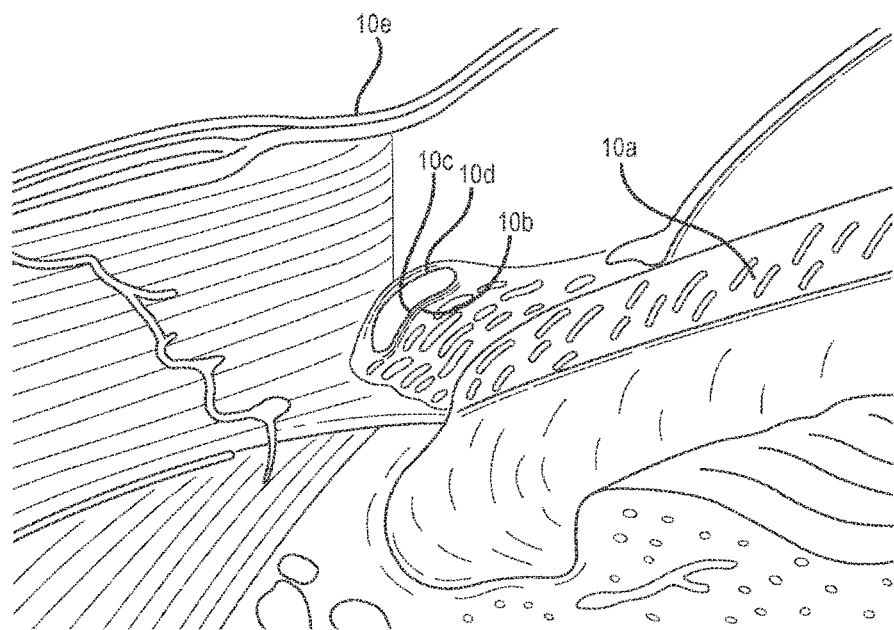

As discussed elsewhere herein, total internal reflection within the eye prevents a surgeon from viewing outflow structures that reside beyond the "critical angle" of the anterior segment optical viewing pathway. As shown in FIG. 6A, structures such as the central iris 619a can be viewed by the surgeon using an optical device 640a such as an optical microscope, camera, video camera, or the like. This is because light 650a from the central iris 619a exits the eye 680a passing through the cornea 615a and is received or detected by the optical device 640a. In contrast, structures in and near the iridocorneal angle 670a, such as the trabecular meshwork 672a, are not visible when using the optical device 640a, subsequent to the total internal reflection due to the dome shape of the cornea. This is because light 660a from the iridocorneal angle 670a undergoes total internal reflection at the interface between the eye's anterior surface structures, which include cornea and tear film 690a and the air 695a (or other material having a different refractive index that than of the anterior eye surface), and hence light from structures such as the trabecular meshwork 672a does not exit the eye 680a through the cornea and is not able to be received or detected by an optical device 640a.

When performing certain minimally invasive glaucoma surgery (MIGS) procedures and other medical treatments, a surgeon will often move an instrument such as a probe throughout various locations within the anterior chamber 607a of the eye 680a. When the instrument is located within the central or inner region of the anterior chamber 607a (e.g. near the central iris 619a and pupil 605a) as indicated by the letter V, the instrument is optically visible to the surgeon both directly and via a microscope. For example, the instrument may be seen in an optical path view or an optical path image provided by the optical device 640a. In this sense, area V represents the area or space within the anterior chamber which is optically visible to the surgeon, and for example can be seen in an image provided by the optical device 640a.

When the instrument (or a portion thereof, such as a distal tip) is located toward the peripheral or outer region of the anterior chamber (e.g. peripheral to line 655a, near the trabecular meshwork 672a) as indicated by the letter N, the instrument (or portion thereof) is not optically visible to the surgeon. For example, the instrument (or portion thereof) would not be able to be seen in a view or an image provided by the optical device 640a. In this sense, area N represents the region within the anterior chamber which is not optically visible to the surgeon, and for example cannot be seen in a view or an image provided by the optical device 640a.

Dashed line 655a provides a representative illustration of the boundary that separates the space V (visible) from the space N (not visible), and corresponds to the "critical angle" discussed elsewhere herein. Relatedly, dashed line 656a provides a representative illustration of the peripheral or outer boundary of space N.

Current methods to view structures which reside beyond the "critical angle" require the use of devices called "goniolenses" which alter the optical pathway by altering the optics of the curved corneal surface. There are two main categories of contact lenses used for this purpose: Those that allow a direct view into the iridocorneal angle 670a and those which allow an indirect e.g. reflected view using mirrors into the iridocorneal angle 670a. The use of such devices to enable viewing of the iridocorneal angle structures requires skill sets to manipulate these contact lenses in real time and to mentally invert the mirror images in the case of indirect goniolenses.

Advantageously, embodiments of the present invention provide systems and methods that enable the surgeon to effectively and accurately move and position a surgical instrument or probe, such as an excimer laser trabeculotomy (ELT) device, throughout various desired or target locations in the peripheral anterior chamber (e.g. throughout region N), the view or image of which would otherwise be obscured or blocked due to total internal reflection. What is more, embodiments of the present invention also enable the surgeon to effectively and accurately move and position a surgical instrument or probe, such as a laser trabeculotomy (ELT) device, throughout various desired or target locations that are located peripheral to space N (e.g. through the trabecular meshwork 672a and the inner wall 625a of Schlemm's canal 611a).

For example, according to embodiments of the present invention, systems and methods are detailed which provide the surgeon with an augmented view or image of structure which could be visualized optically with a goniolens, but in this case are instead imaged without a goniolens (e.g. a tissue or tissue layer such as the trabecular meshwork 672a) and, in addition, may also include images of structure which could not be visualized by a goniolens that includes an OCT image of a target location at a target tissue region (e.g. a tissue or tissue layer such as the juxtacanalicular trabecular meshwork, the inner wall of Schlemm's canal, the outer wall of Schlemm's canal, and the sclera). Such image may be represented by graphic images similar to the structures if they could be seen and also may be represented by, for example, graphical visual elements that identifies a target location and relative location. Relatedly, in some cases, a graphical visual element identifying a target location can operate to identify a particular tissue or tissue layer, such as the trabecular meshwork, the juxtacanalicular trabecular meshwork, the inner wall of Schlemm's canal, the outer wall of Schlemm's canal, or the sclera.

An augmented view or image can be generated by overlaying the OCT image and the graphical element, and the graphical element can be registered with an optical path view or an optical path image. The augmented view or image can also include a graphical element corresponding to the instrument and/or a target location. For example, the augmented view or image can include a probe marker that corresponds to the position of a probe or a probe tip. In some cases, the augmented view or image can include a graphical element corresponding to a probe line or a guidance arrow. The graphical elements are particularly useful in providing the surgeon with visible guiding cues for navigating space N and other areas or structures (e.g. sub-surface tissues or tissue layers disposed beneath or peripheral to the trabecular meshwork 672a such as the inner wall 625a of Schlemm's canal 611a) which are not optically visible.

In this way, the surgeon is presented with an augmented view or image wherein a target location and/or an instrument (or portion thereof), is made "visible" to the surgeon by virtue of one or more graphical visual elements alone or combined with one or more OCT images, wherein the target location and/or instrument (or portion thereof) is not visible in an optical view or an optical image without a goniolens. Hence, systems and methods disclosed herein enable a surgeon to perform glaucoma surgery of the outflow structures (e.g. MIGS) without having to use a goniolens.

Panel (1) of FIG. 6A illustrates additional aspects of a critical angle feature described herein. As shown here, light 650a from a location posterior to the cornea 615a, having an angle of incidence "a" with respect to a normal 675a to the medium boundary 685a (e.g. interface between tear film 690a and the air 695a), crosses the boundary with partial refraction. In contrast, light 660a from a more peripheral location within the anterior chamber 607a, having an angle of incidence "b" with respect to the normal 675a, does not cross the boundary 685a, but instead is reflected back into the anterior chamber 607a. According to some embodiments, a critical angle "c" can be defined as the threshold angle of incidence above which there is total internal reflection. Hence, it can be seen that with light 660a, there is a total internal reflection that prevents a surgeon from viewing certain outflow structures that reside beyond the critical angle "c" of the anterior segment optical viewing pathway. According to some embodiments, the critical angle "c" is about 46 degrees, such that light, coming from tissue structures or devices that are positioned within the anterior chamber, which exceeds an angle of 46 degrees at the boundary 685a is reflected back into the anterior chamber. In some cases, the value for the critical angle can be determined based on an average value for a patient population. In some cases, the value for the critical angle can be determined based on a specific value for a particular patient being treated. In some cases, the critical angle can correspond to a distance of between about 2 mm and about 4 mm from the surface of the trabecular meshwork. In some cases, the critical angle can correspond to a distance of about 3 mm from the surface of the trabecular meshwork.

FIG. 6A-1 depicts anatomical aspects of the eye at or near the iridocorneal angle. As shown here, the eye includes a trabecular meshwork 10a, a juxtacanalicular trabecular meshwork (JCTM) 10b, an inner wall 10c of Schlemm's canal, an outer wall 10d of Schlemm's canal, and a sclera 10e. Schlemm's canal is represented by the space between inner wall 10c and outer wall 10d. These features are also depicted in the circular inset in FIG. 6A.

As depicted in FIGS. 4, 5, 10, and 11, an OCT unit or device, which may for example include a microscope OCT, can share an imaging path with an optical device, which may for example include an optical microscope, camera, video camera, or the like. Embodiments of the present invention enable simultaneous imaging of the eye with an optical microscope and an OCT device. In some instances, the OCT device constructs its images by scanning depth profiles at individual X-Y coordinates, using a wavelength of about 1300 nm. In contrast, a typical optical device can allow the user to see visible light within a different part of the electromagnetic spectrum, which corresponds to wavelengths within a range from about 390 nm to about 700 nm. This allows separation of the OCT signal from the optical signal, even as they share an imaging path. OCT devices and optical devices operate on different principles, such that the optical device is limited by total internal reflection for purposes of viewing structures that reside beyond the critical angle of the anterior chamber optical viewing pathway (e.g. structures such as the surface of the trabecular meshwork), whereas the OCT device does not have those same limitations. This is in part due to the different types of electromagnetic radiation involved with these two imaging modalities, as well as the optical phenomena and operational principles involved. For example, the operation of optical devices involves reflection of light, whereas the operation of OCT devices involves backscattering of light, and/or the sequential interrogation of single points in the sample using a focused beam so as to build an image.

Figure 6B:
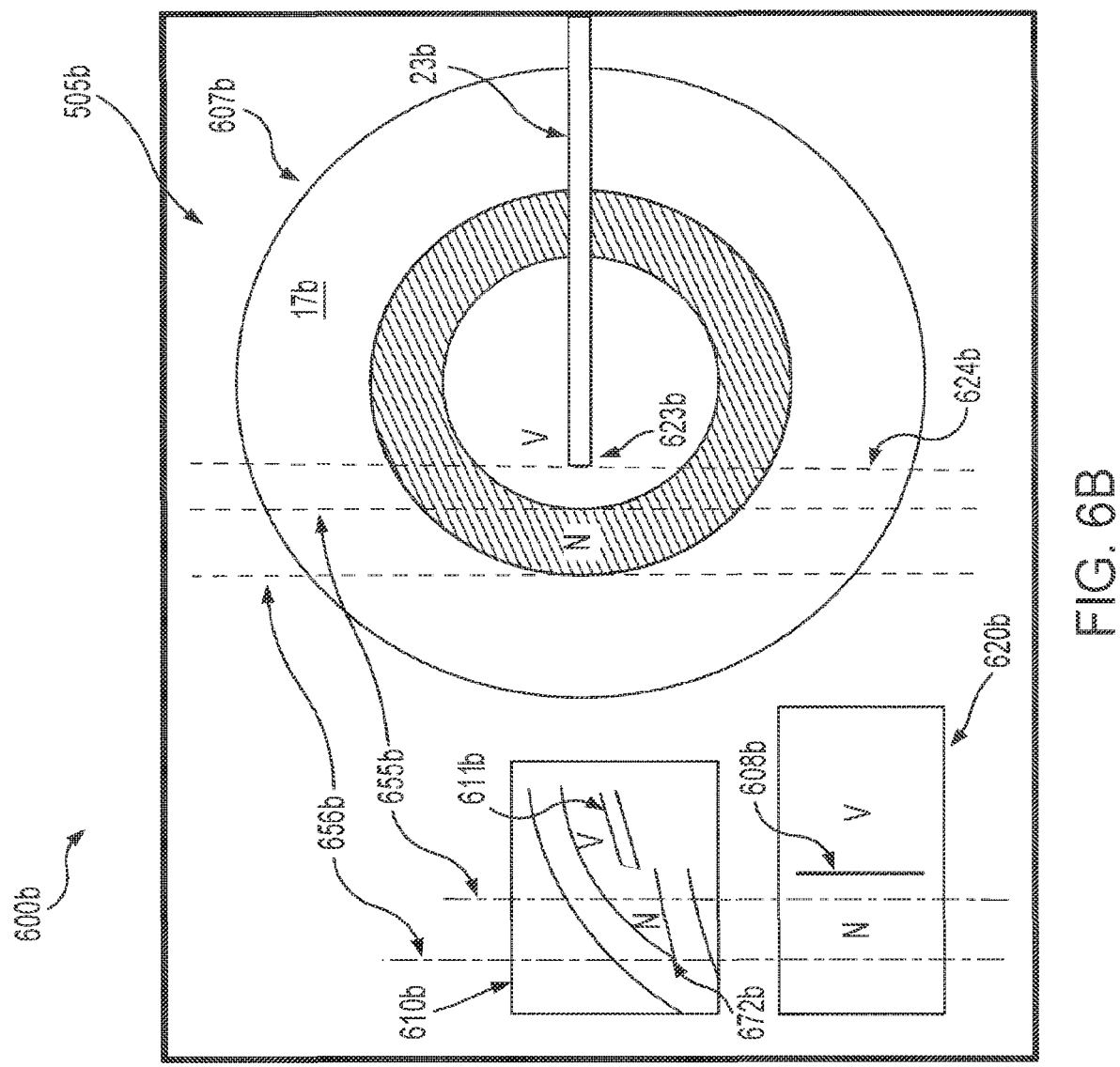
FIGS. 6B and 6C illustrate aspects of an augmented view or image, according to embodiments of the present invention.

FIG. 6B illustrates an exemplary augmented image or augmented view 600b. As described elsewhere herein, an augmented image may be viewed by a user or surgeon through oculars of a microscope for example with a heads up display adjacent to or overlying optically visible structures. Such an augmented image can be displayed on a heads up display, an external display device, or a display coupled to a user interface. According to some embodiments, augmented image 600 can be viewed on any of a variety of viewing of viewing devices, such as a display device, a microscope device, a heads up display, a viewing monitor, a virtual reality viewing device, an augmented reality viewing device, or the like. As shown here, the augmented image or view 600b can include an optical image 505b or an optical path view through the oculars of an optical microscope, and optical image 505b includes an anterior or top-down view of an eye 607b having a sclera 17b. The optical image or optical view also shows an elongated probe 23b that has been inserted through a corneal paracentesis incision and into the anterior chamber of the eye.

The augmented image or view 600b also includes an OCT image 610b. As shown here, OCT image 610b corresponds to a side or cross-section view of the eye. Further, augmented image or augmented view 600b can include another OCT image 620b. As shown here, image 620b corresponds to an anterior or top-down view of the eye.

Dashed line 655b provides a representative illustration of the boundary that separates the space V within the anterior chamber which is optically visible from the space N within the anterior chamber which is not optically visible, and this boundary corresponds to the "critical angle" visibility discussed elsewhere herein. Relatedly, dashed line 656b provides a representative illustration of the peripheral or outer boundary of space N within the anterior chamber.

Embodiments of the present invention provide systems and methods that enable the surgeon to effectively and accurately move and position a surgical instrument, such as a probe, throughout various desired or target locations within the peripheral anterior chamber (e.g. throughout space N), the optical image or view of which would otherwise be blocked due to total internal reflection, and to also navigate the surgical instrument to other areas or structures (e.g. sub-surface tissues or tissue layers disposed beneath or peripheral to the trabecular meshwork 672b) which are not optically visible. For example, as discussed elsewhere herein, OCT images 610b and 620b can include graphical visual elements that are disposed, or are at least partially disposed, peripheral to dashed line 655b.

As shown here, OCT image 610b includes a graphical visual element 611b corresponding to the elongate probe 23b, which is disposed in space V, the space within the anterior chamber which is optically visible to the surgeon. The portion of the iris posterior to the elongate probe may not be visible in image 610b (e.g. below graphical visual element 611b) due to an OCT shadowing phenomena, whereby an object can cause optical shadowing that obscures underlying tissues in an OCT image. Relatedly, OCT image 620b includes a graphical visual element 608b corresponding to a distal end 623b of the elongate probe 23b, which is similarly disposed in space V. Dashed line 624b represents the location of the probe distal end 623b.

Figure 6C:
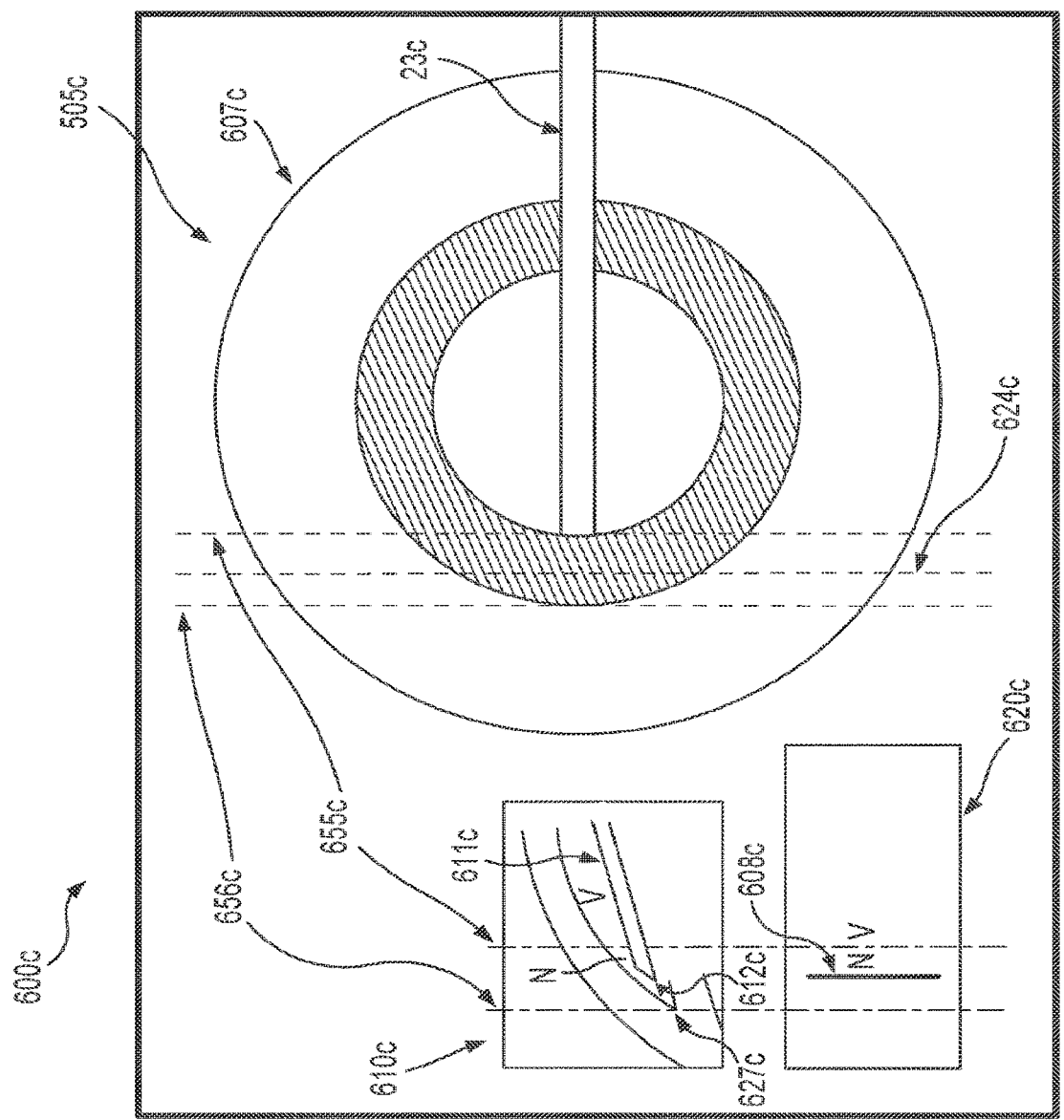

As discussed elsewhere herein, for example with reference to FIG. 6C, as the surgeon moves the distal end of the elongate probe from space V to space N, the distal end of the probe 23b will disappear from the optical image or view 505b, while OCT image 610b allows the surgeon to seamlessly visualize the probe across this transition by virtue of observing graphical visual element 611b as it moves from space V to space N, and optionally into other areas or structures (e.g. sub-surface tissues or tissue layers disposed beneath or peripheral to the trabecular meshwork 672b). Likewise, OCT image 620b allows the surgeon to seamless visualize the probe across this transition by virtue of observing graphical visual element 608b as it moves from space V to space N, and optionally into other areas or structures (e.g. sub-surface tissues or tissue layers disposed beneath or peripheral to the trabecular meshwork). According to some embodiments, the boundary itself (i.e. dashed line 655b) is described here for illustration purposes only, and is not displayed anywhere in the augmented image or view 600b.

FIG. 6C illustrates an exemplary augmented image or augmented view 600c. The distal end (not shown) of the probe 23c has now been advanced from space V (the positioning depicted in FIG. 6B) to space N, as indicated by dashed line 624c of the optical view or image 505c. The augmented image or view 600c also includes an OCT image 610c. As shown here, OCT image 610c corresponds to a side or cross-section view of the eye. The portion of the iris posterior to the elongate probe may not be visible in image 610c (e.g. below graphical visual element 611c) due to an OCT shadowing phenomena. Further, augmented image or augmented view 600c can include another OCT image 620c. As shown here, image 620c corresponds to an anterior or top-down view of the eye 607c.

Dashed line 655c provides a representative illustration of the boundary that separates the space V within the anterior chamber which is optically visible from the space N within the anterior chamber which is not optically visible, and this boundary corresponds to the "critical angle" visibility discussed elsewhere herein. According to some embodiments, the boundary itself (i.e. dashed line 655c) is described here for illustration purposes only, and is not displayed anywhere in the augmented image or view 600c. Relatedly, dashed line 656c provides a representative illustration of the peripheral or outer boundary of space N within the anterior chamber.

OCT images 610c and 620c can include graphical visual elements that are disposed, or are at least partially disposed, peripheral to dashed line 655c. As shown here. OCT image 610c includes a graphical visual element 611c corresponding to the elongate probe 23c, which is disposed in space V (the space within the anterior chamber which is optically visible to the surgeon) and extends into space N (the space within the anterior chamber which is not optically visible to the surgeon). Relatedly. OCT image 620c includes a graphical visual element 608c corresponding to a distal end of the elongate probe 23c, which is disposed in space N.

Because the surgeon has moved the distal end of the elongate probe 23c from space V to space N, the distal end of the probe has disappeared from the optical image or view 505c. During this movement, however, OCT image 610c allows the surgeon to seamlessly visualize the probe across this transition from space V to space N, by virtue of observing the distal portion 612c of graphical visual element 611c moving from space V to space N. Optionally, the surgeon may be guided by other graphical visual elements overlaid with OCT image 610c, as discussed elsewhere herein, to move the probe throughout various locations in space N. During this guided navigational process, the surgeon can use OCT image 610c to visualize the position and/or location of probe 23c relative to anatomical structures of the eye 607c by observing graphical visual element 611c (and optionally, distal portion 612c) move relative to the other graphical visual elements. For example, other graphical visual elements may correspond to sub-surface tissues or tissue layers disposed beneath or peripheral to the trabecular meshwork 672*c*.

Likewise, OCT image 620*c* allows the surgeon to seamless visualize movement of the probe across this transition from space V to space N, by virtue of observing graphical visual element 608*c* as it moves from space V to space N. Optionally, the surgeon may be guided by other graphical visual elements overlaid with OCT image 620*c*, as discussed elsewhere herein, to move the probe throughout various locations in space N. During this guided navigational process, the surgeon can use OCT image 620*c* to visualize the position and/or location of probe 23*c* relative to anatomical structures of the eye 607*c* by observing graphical visual element 608*c* move relative to the other graphical visual elements. For example, other graphical visual elements may correspond to sub-surface tissues or tissue layers disposed beneath or peripheral to the trabecular meshwork. In some cases, graphical visual element 608*c* may be generated when the distal end of the elongate probe is no longer visible in the microscope image as a result of the distal end of the elongate probe being obscured due to total internal reflection of the corner near an iridocorneal angle of the eye.

Hence, embodiments of the present invention are well suited for use in viewing and navigating in and around structures of the eye near the iridocorneal angle, such as the trabecular meshwork and Schlemm's canal, which would otherwise involve more difficult techniques, for example techniques requiring the use of a goniolens. Likewise, systems and methods disclosed herein can allow a surgeon to view angle structures that are block by total internal reflection, by providing the surgeon with images or information of those otherwise poorly visible or non-visible structures, such as the collector channel system. Such images or information can be generated by making use of OCT optical coherence tomography (OCT) technologies.

As discussed elsewhere herein, various image types, graphical visual elements, and/or treatment reference markers can be in registration. For example, one or more OCT images, microscope images, graphical visual elements, and/ or treatment reference markers can be in registration with one another (e.g. properly aligned). In some cases, one or more graphical visual elements and/or treatment reference markers can be mapped to their corresponding locations in an image. In an exemplary embodiment, an optical coherence tomography image is in registration relative to a microscope image, a graphical visual element is overlaid to and in registration with the microscope image, and a treatment reference marker is overlaid to and in registration with the optical coherence tomography image.

Figures 1, 6D:
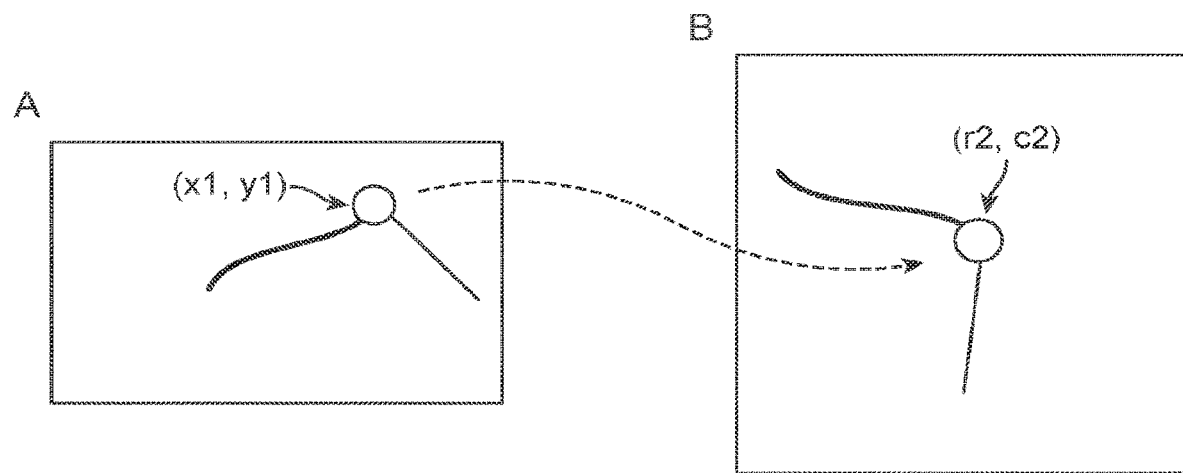
Figures 2, 6D:
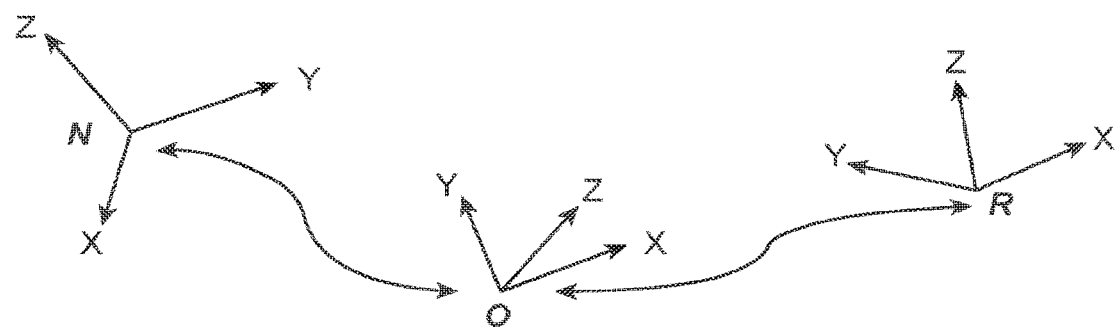

According to some embodiments, registration can involve the mapping a treatment reference marker, a first image or view, and/or a graphical visual element, to a second image or view. As shown in FIG. 6D-1, a first two dimensional coordinate system A that corresponds to a treatment reference marker, a first image or view, and/or a graphical visual element, can be in registration with a second coordinate system B that corresponds to a second image. In this way, an object at one position (e.g. x1,y1) in the first image can be mapped to a corresponding position (e.g. r2, c2) in the second image. In the context of overlapping or overlaid images, for example, this means that different viewpoints of the same physical space can be associated, such that the same feature may be depicted differently in two different images.

According to some embodiments, registration can be performed in three dimensions and/or using an intermediate coordinate system. For example, as depicted in FIG. 6D-2, an intermediate coordinate system (O) can be used to register a first (N) coordinate system with a second (R) coordinate system. That is, by having a known relationship between first coordinate system (N) and intermediate coordinate system (O), and a known relationship between intermediate coordinate system (O) and second coordinate system (R), it is possible to have a known relationship, or registration, between first coordinate system (N) and second coordinate system (R).

Figure 6E:
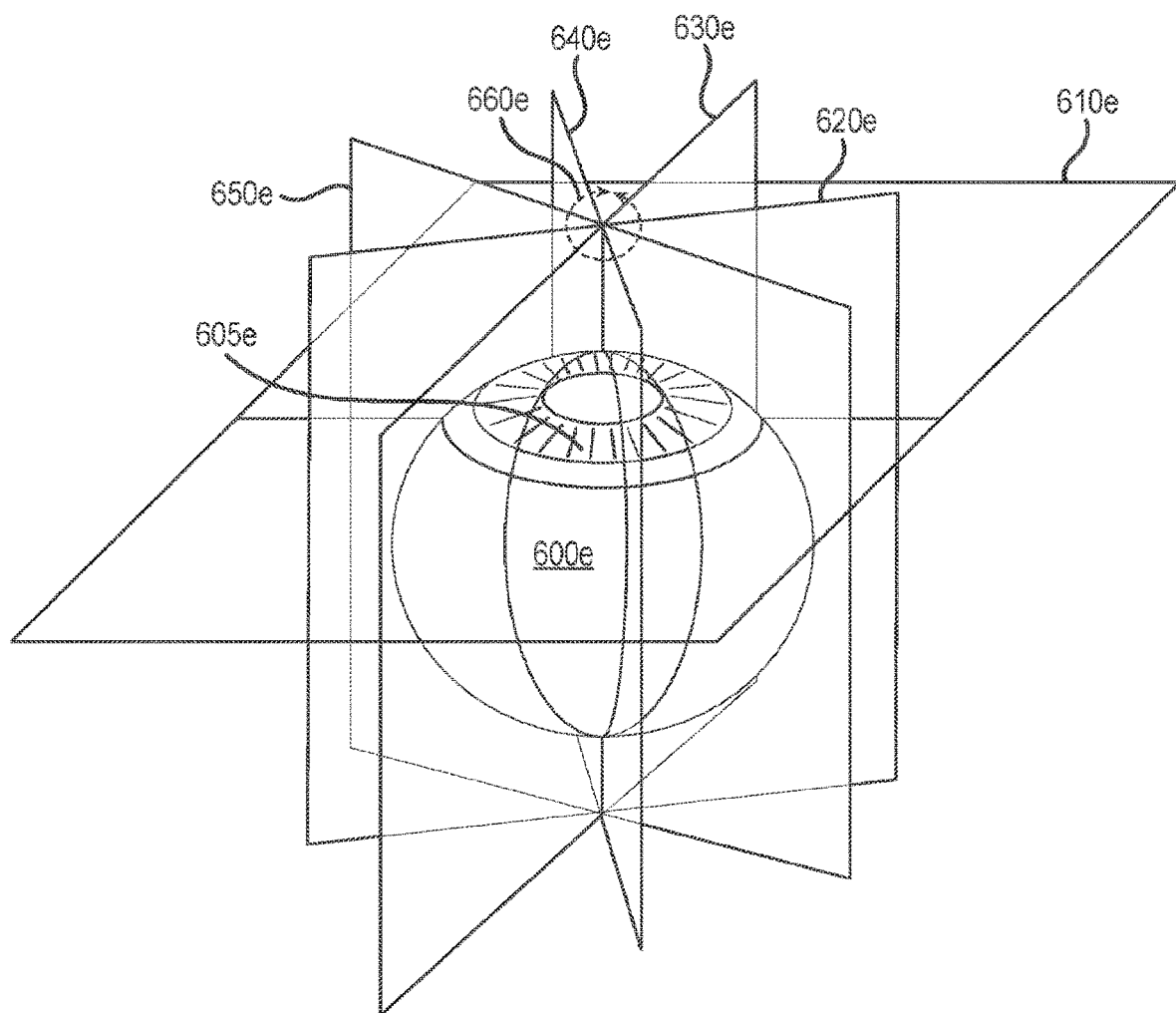
FIG. 6E depicts aspects of imaging planes according to embodiments of the present invention.

FIG. 6E provides additional information concerning the various imaging planes that may be involved when generating an augmented image according to embodiments of the present invention. According to some embodiments, a microscope image or view allows the a surgeon to view tissue or structures of the eye 600*e* corresponding to an x-y plane 610*e* of the eye, which may also be referred to as an optical image plane, coronal plane, or an iris plane (e.g. being co-planar with iris 605*e*). As discussed elsewhere herein, an optical image or view can be substantially parallel to or in co-planar alignment with the x-y plane 610*e* of the eye. According to some embodiments, an image or view that is substantially parallel to or in co-planar alignment with the x-y plane 610*e* of the eye enables the surgeon to adequately visualize the anatomical structures of interest (e.g. iris) within the anterior chamber when performing the surgical procedure. The x-y plane 610*e* can also correspond to radial depth locations or markers discussed elsewhere herein. The OCT imaging modalities disclosed herein can allow a surgeon to view tissue or structures of the eye corresponding to any of a variety of transverse or radial planes as well, depicted here for example as first transverse plane 620*e*, second transverse plane 630*e*, third transverse plane 640*e*, and a fourth transverse plane 650*e*. Transverse planes may also be referred to as anterior-posterior planes. Although only four transverse planes are depicted here, OCT imaging modalities enable the imaging of planes at any orientation throughout the 360 range 660*e* depicted here. The transverse planes can provide information about tissue structures at various depths perpendicular or transverse to the optical image plane 610*e*. According to some embodiments, OCT imaging modalities can also allow a surgeon to view tissue or structures of the eye corresponding to the x-y plane 610*e*. According to some embodiments, an augmented image can include a microscope image of the eye obtained by the optical microscope, where the microscope image corresponding to an x-y plane 610*e* of the eye. The trabecular meshwork of a target tissue region may not be visible in the microscope image due to total internal reflection of the trabecular meshwork of the target tissue region. The augmented image can also include an optical coherence tomography image of the target tissue region of the eye, where the optical coherence tomography image is obtained by an optical coherence tomographer or tomography apparatus. The optical coherence tomography image can correspond to a transverse or anterior-posterior plane (e.g. 620*e*, 630*e*, or 640*e*) of the eye that is perpendicular to the x-y plane 610*e* of the eye. As discussed elsewhere herein, the optical coherence tomography image can be in registration relative to the microscope image. Augmented images can also include one or more graphical visual elements overlaid to and in registration with the microscope image (e.g. corresponding to x-y plane 610*e*), for example where a graphical visual element is mapped to a radial target location of the target tissue region, and the radial target location is based on a preoperative optical coherence tomography image or a real-time optical coherence tomography image obtained by an optical coherence tomographer. As depicted in FIGS. 15A to 15C, preoperative OCT images and/or augmented preoperative OCT images can correspond to the x-y plane 610e as well (e.g. depicting collector channels and/or target locations). As further discussed elsewhere herein, one or more treatment reference markers can be overlaid to and in registration with an optical coherence tomography image (e.g. corresponding to a transverse plane such as 620e, 630e, or 640e) where a treatment reference marker is mapped to an anterior-posterior depth target location of the target tissue region and to a radial target location of the target tissue region. In some cases, the anterior-posterior depth target location corresponds to the Schlemm's canal. The graphical visual element (e.g. depicted in an image corresponding to plane 610e) can aid the physician in advancing a distal end of an elongate probe to a radial target location, and the treatment reference marker (e.g. depicted in an image corresponding to plane 620e) can aid the physician in advancing the distal end of the elongate probe to an anterior-posterior depth target location.

As discussed elsewhere herein, embodiments of the present invention allow a surgeon to have a field of view (e.g. observable area via an optical device) that includes multiple perspectives. For example, a field of view corresponding to augmented image 600 of FIG. 6 includes optical image or view 505 for a perspective associated with x-y plane 610e of FIG. 6E, as well as an OCT image 610 for a perspective associated with a transverse plane (e.g. transverse plane 620e of FIG. 6E). The mapping and registration techniques disclosed herein can operate to preserve spatial relationships between these different perspective views and the objects and movements within them, such that the surgeon or operator can concurrently view any changes in the optical image or view 505, the OCT image 610, and/or the OCT image 620, while observing a single field of view as provided by augmented image 600. Note that although the transverse planes are shown as traversing the entirety of the eye, from the anterior-most portions to the posterior-most portions, the transverse-oriented images provided to the surgeon during surgery correspond to a more narrow band or region within these planes. Specifically, the images depict tissue that is at or near the iris plane of the eye (e.g. as shown in OCT images 610 and 620 of FIG. 6).

Figure 7A:
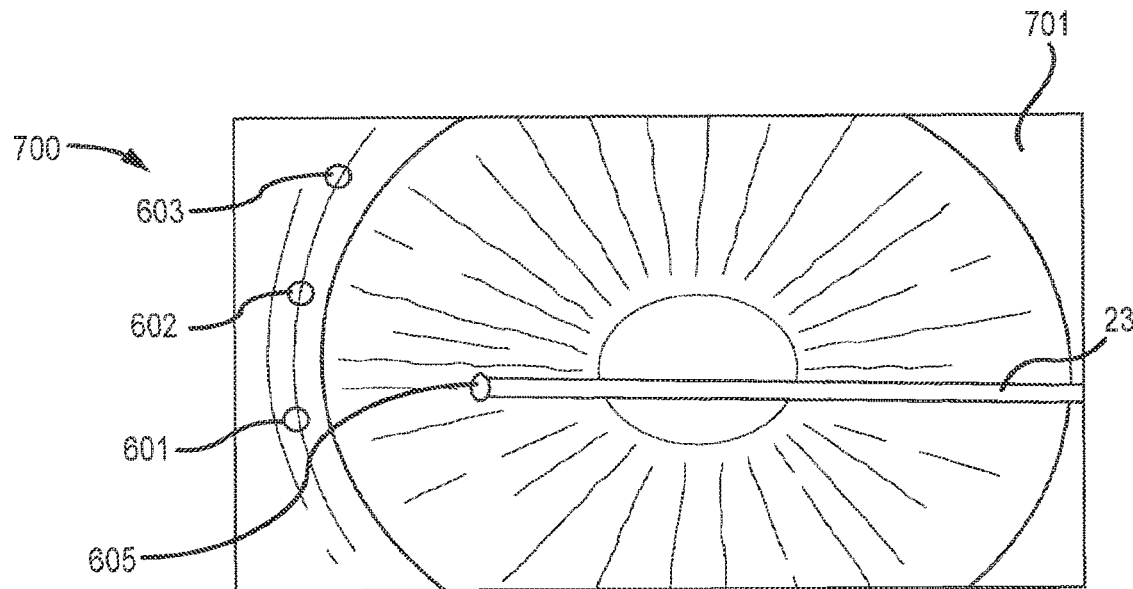
Figures 1, 7A:
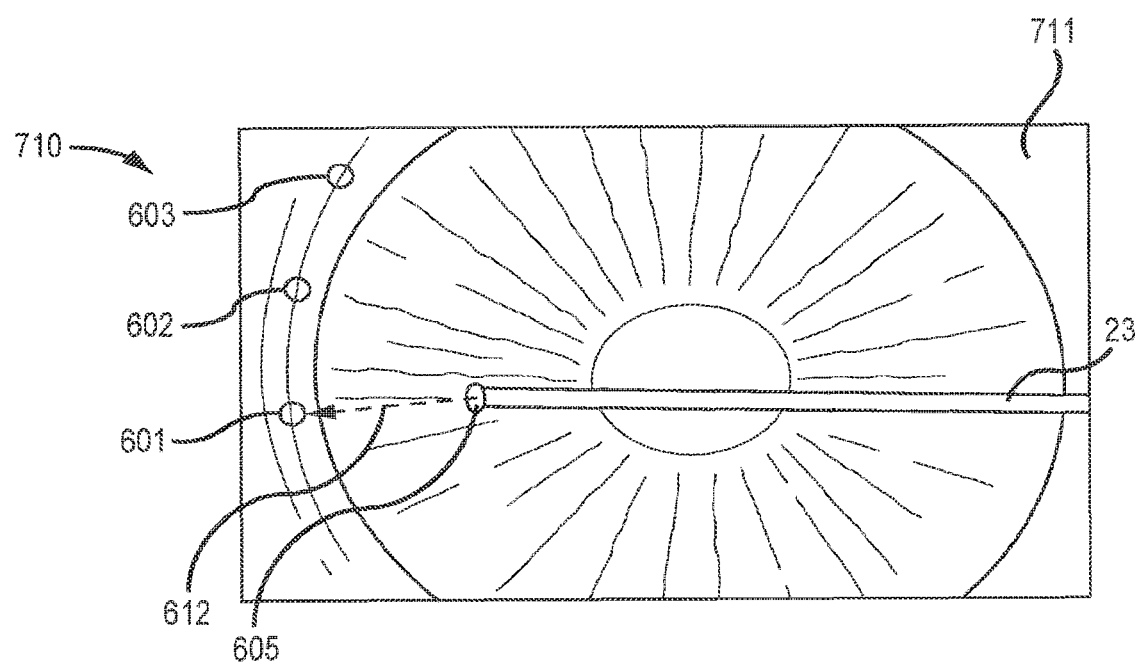
Figure 7B:
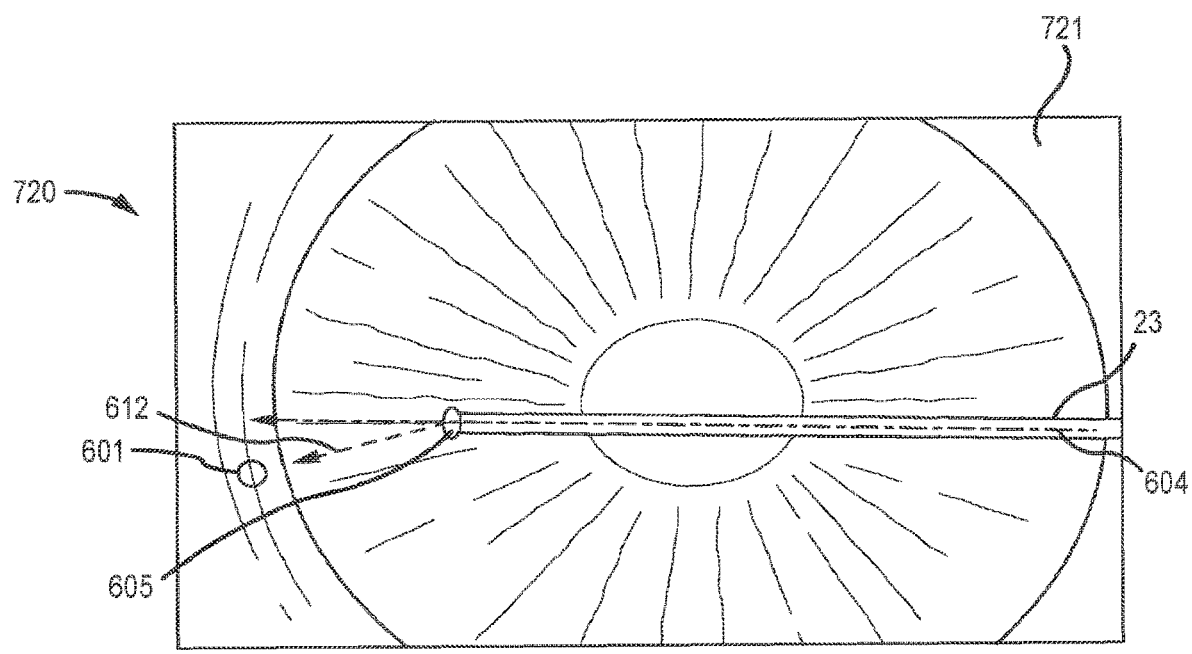

FIGS. 7A to 7F-1 show exemplary augmented images 700, 710, 720, 730, 740, 750, 760, 770, 780, and 790 perceived by a physician or user during a procedure. As illustrated in FIG. 7A (augmented image 700), one or more treatment reference markers 601, 602, 603 corresponding to one or more target locations may be overlaid over the optical image 701 of an eye or an optical path view through the oculars of an optical microscope for a physician to view and select. In the optical image or optical path view 701 shown here, it is possible to visualize the anatomical structures of the eye within the anterior chamber, from the pupil to the trabecular meshwork. As discussed elsewhere herein, however, the peripheral structures at or near the iridocorneal angle, such as the trabecular meshwork, may not be visible in the optical image or view. Hence, according to some embodiments, the optical image or view provided here is for illustration purpose only, and in practice will not include such peripheral structures. The one or more target locations may be determined from a preoperative OCT image or other images then mapped to the live optical image as described elsewhere herein. Upon a selection of a target location, a guidance arrow 612, (shown in augmented image 710 of FIG. 7A-1), extending from the distal tip marker 605 towards the selected treatment reference marker 601 corresponding to that selected target location may be generated (e.g. overlaid to optical image or view 711) to guide the physician, to orient the probe 23 to longitudinally align with the guidance arrow. In some cases, the treatment reference markers 602, 603 corresponding to the non-selected target locations may disappear from the view after the first treatment reference marker 601 (or corresponding target location) has been selected. Proceeding to FIG. 7B (augmented image 720), the probe 23 may be advanced towards the selected target location corresponding to treatment reference marker 601 guided by the probe line 604 coaxial with the elongate axis of the probe and the guidance arrow 612. As depicted here, treatment reference marker 601, probe line 604, distal tip marker 605, and guidance arrow 612 can be overlaid to optical image or view 721. When the probe tip is detected to be within a predetermined distance from the target location or when the probe line is aligned with the guidance arrow as shown in FIG. 7C (augmented image 730), an OCT scan may be performed. Relatedly, the OCT scan may be performed with the probe tip is detected to be beyond the "critical angle" visibility, and consequently OCT image 610-4 may be generated. As described elsewhere herein, the detection may be based on the live optical images. The OCT scan may be a microscope-based OCT scan and in some cases, a two-dimensional image may be overlaid onto the optical image. In some cases, arrows 614 indicating a scanning range of the microscope-based OCT may be overlaid to the optical image or view 731 when a 3D scan (i.e., C-scan) is desired. The scanning range or volume may be defined by the two arrows 614 pointing from the fiber tip to the target location. Alternatively, the microscope-based OCT may be 2-D scan (i.e., B-scan). The scanning plane may be along the longitudinal axis of the probe and the anterior-posterior plane of the eye. The scanning range may be from the fiber optic tip to the target location as indicated by the arrow 612. In some cases, the arrows 614 may indicate a scanning range for fiberoptic-based OCT. Similarly, the arrows 614 may define a scanning range for a 3-D scan or 2-D scan of the fiberoptic-based OCT. The scanning range may be in a range defined by an angle 714 such as from 1 degree to 45 degrees.

As shown in augmented image 740 of FIG. 7C-1, the microscope-based OCT image 610-4 may comprise guidance arrows 613 to guide the physician in adjusting the probe orientation and advancing direction within an anterior-posterior plane of the eye. Alternatively, the guidance arrows may indicate a 3D OCT scan range. This OCT image supplements positional information that may not be perceivable from the optical image 741. As described elsewhere herein, a probe marker 611 indicating at least the position of the probe tip with respect to the target location corresponding to treatment reference marker 601-1 may be overlaid onto the microscope-based OCT image. As discussed elsewhere herein, the height of Schlemm's canal may be about half the height of the trabecular meshwork. According to some embodiments, the guidance arrow 613 points in a direction toward Schlemm's canal. The location of treatment reference marker 601-1 can correspond to the position of Schlemm's canal. According to some embodiments, treatment reference marker 601-1 can represent a depth target location (e.g. depth relative to an anterior-posterior axis of the eye) and/or a radial target location (e.g. distance relative to center or pupil of the eye). In some cases, a radial target location may also be referred to as a radial depth target location, where, for example, the radial depth corresponds to the radial distance from the center of the eye or the radial distance from the center of the pupil. In some cases, the location of a treatment reference marker (e.g. 601-1) corresponds to a distance from a corneal paracentesis incision through which an elongated probe can be inserted through and into the anterior chamber of the eye.

Figures 4, 7D:
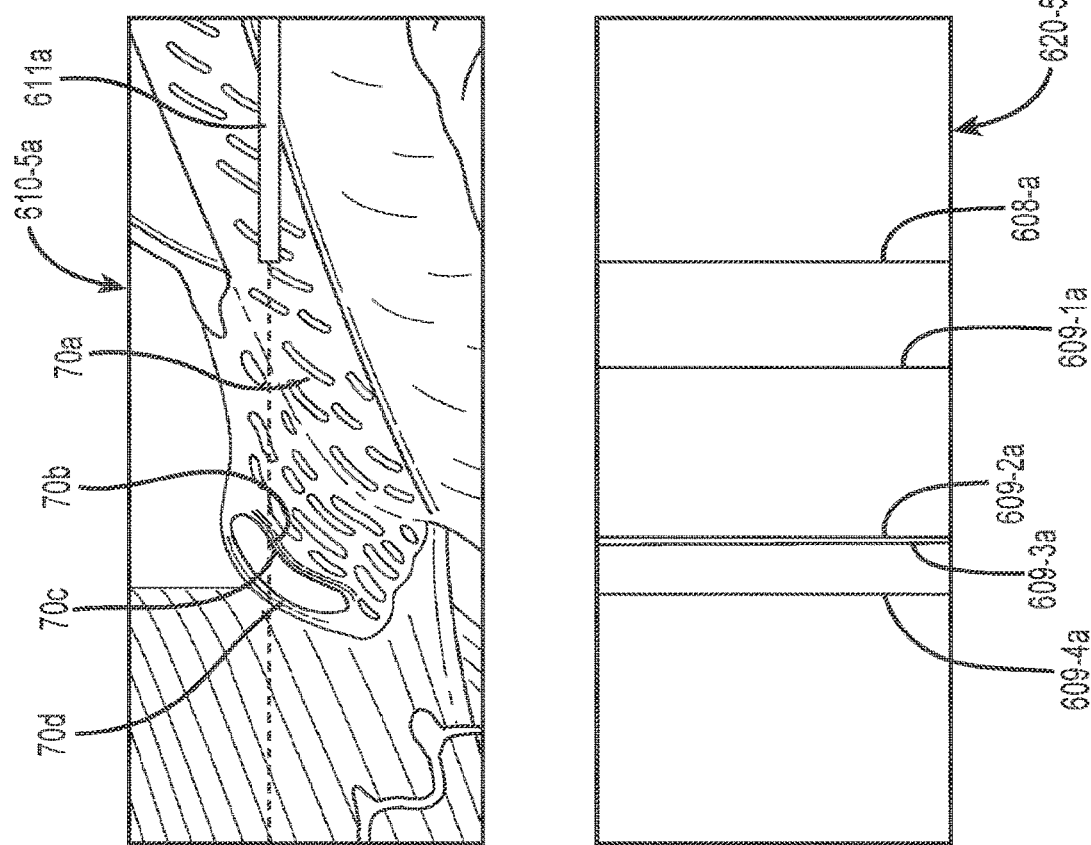

As illustrated in FIG. 7D-2 (augmented image 750), as the distal tip marker 605 corresponding to the distal end of the elongate probe 23 approaches the treatment reference marker 601 corresponding to the target location and is detected to be within a predetermined distance from the treatment reference marker 601 (or where the distal end is detected to be within a predetermined distance from the target location), a second OCT scan may be performed. The second OCT scan may be a fiberoptic-based OCT scan which can be used to generate image 620-5. In some cases, the second OCT scan may be a B-scan and arrows indicating a scan range may be overlaid to the optical image 751. Alternatively, the second OCT scan may be an A-scan along the axial of the probe and the scan range may not be shown on the augmented image 750. A magnified view of the second OCT scan (A-scan or image 620-5) may be overlaid onto the optical image 751 in a picture-within-picture like format. For clarity, FIG. 7D shows a magnified view of an A-scan image 620-5 showing a plurality of A-scan distance markers, which may be overlaid on the augmented image. A plurality of A-scan distance markers such as lines may be generated based on the A-scan result and overlaid to the optical image 751. The distance markers (e.g., fiberoptic tip position marker 608, TM distance marker 609-1) may dynamically change locations or spacing to reflect the relative locations between the distal end of the probe and the surface of the trabecular meshwork, the JCTM, the inner wall of the Schlemm's canal, the outer wall of the Schlemm's canal, or the sclera.

The accurate and precise positioning measurements of the probe tip and associated markers can be used in combination with various ophthalmic surgeries. In an example, ELT procedure may be performed under guidance of the augmented images. The plurality of A-scan distance markers as shown in the example, may comprise a distance marker 608 corresponding to a distal end of the elongate probe or fiber optic tip, a distance marker 609-1 corresponding to a surface of the trabecular meshwork, a distance marker 602-2 corresponding to a juxtacanalicular trabecular meshwork (JCTM), a distance marker 609-3 corresponding to an inner wall of the Schlemm's canal, a distance marker 609-4 corresponding to an outer wall of the Schlemm's canal, or a distance marker 609-5 corresponding to a sclera. The outer wall of Schlemm's canal may be relatively fixed with regard to the overall structure of the eye, whereas the inner wall of Schlemm's canal can move, along with the trabecular meshwork, relative to the overall eye structure. Due to normal physiological processes, the distance between the inner and outer walls of Schlemm's canal can dynamically fluctuate, for example between 20 microns (e.g. when filled with aqueous humor only) and 200 microns (e.g. when filled with aqueous humor and red blood cells). An ELT laser probe can have an accuracy on the order of 1.7 microns per pulse, and thus can be operated to effectively ablate the inner wall of Schlemm's canal without ablating the outer wall of Schlemm's canal. As discussed elsewhere herein, when the distance marker 609-3 corresponding to the inner wall of Schlemm's canal disappears (e.g. the overlay is removed from the OCT image due to penetration of the inner wall, a signal can be transmitted to the laser to cease delivery of ablation pulses, and a signal can be provided to the surgeon indicating that penetration has been completed. In this way, the system can provide an automated stop signal, an informative stop signal, or both.

Figures 1, 12B:
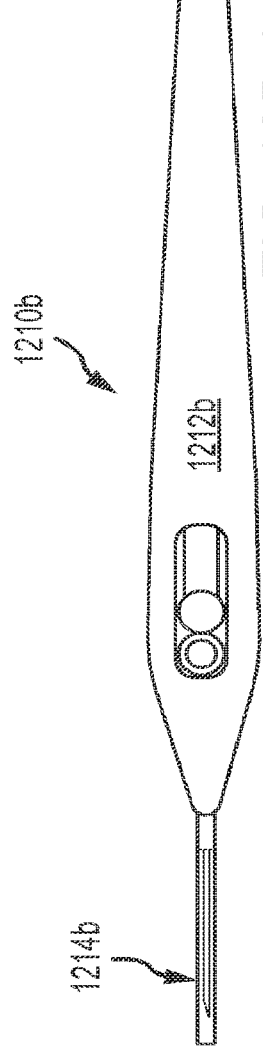
Figures 2, 12B:
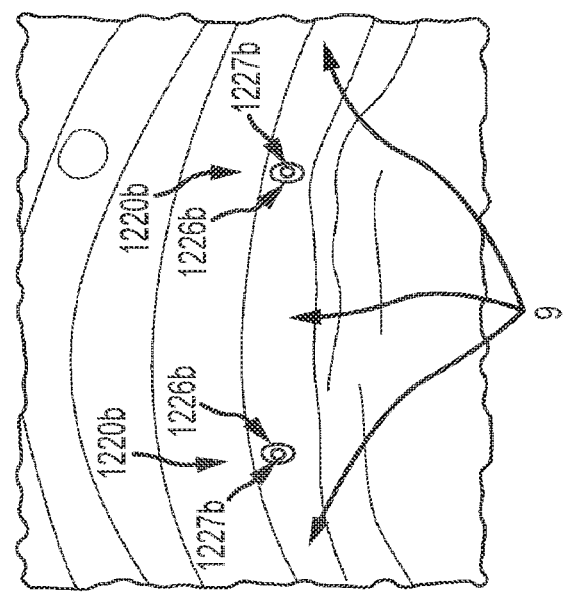
Figures 3, 12B:
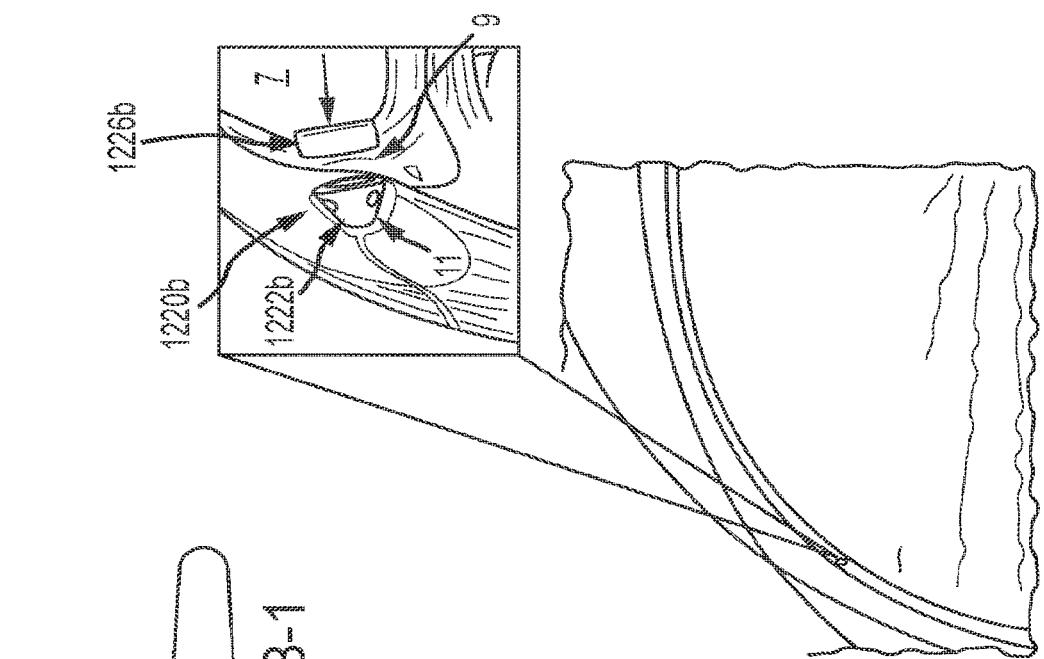
Figures 4, 12B:
Figures 1, 12C:
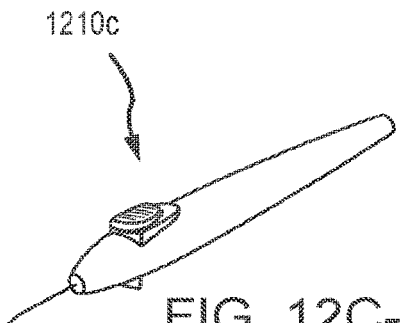
Figures 2, 12C:
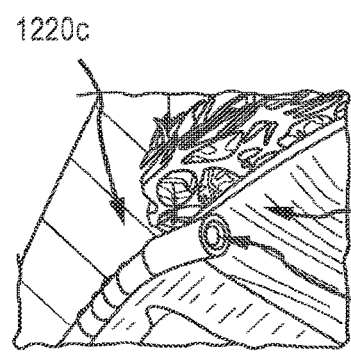
Figures 3, 12C:
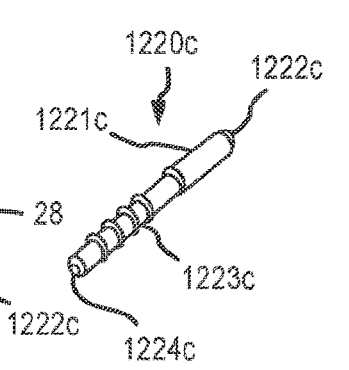
Figures 4, 12C:
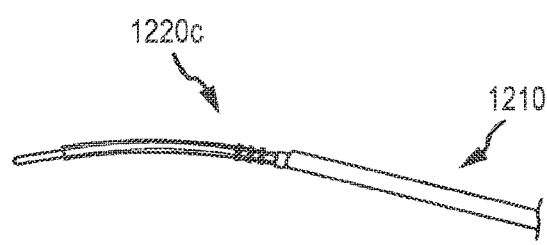
Figures 5, 12C:
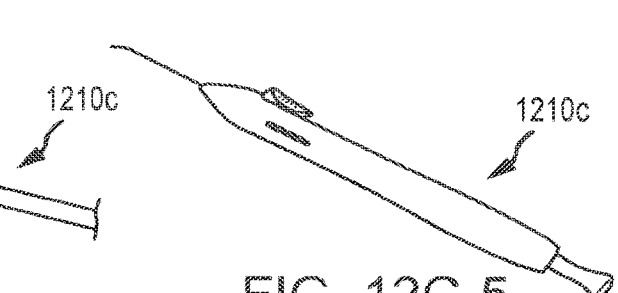
Figures 6, 12C:
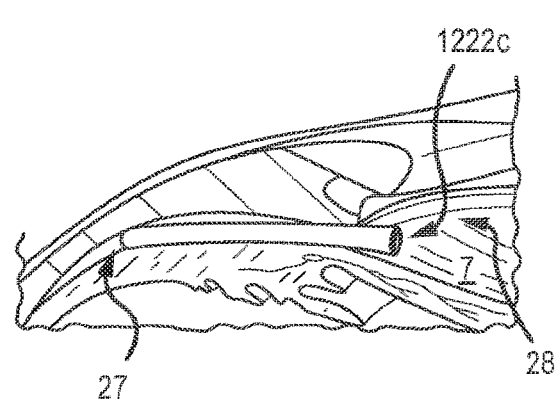
Figures 7, 12C:
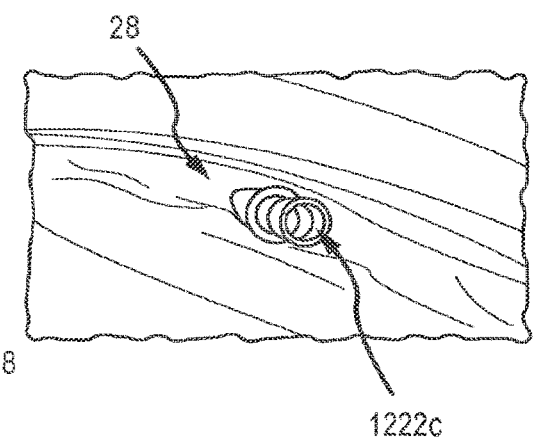

For additional clarity, FIG. 7D-4 provides an enhanced illustration of aspects of FIGS. 7 and 7D-2 (specifically, images 610-5 and 620-5), and depicts additional details of the anatomical features involved. As depicted in FIG. 7D-4, image 610-5a and image 620-5 can both be within the field of view of the surgeon, for example as pan of an augmented image or augmented microscope view, as discussed elsewhere herein. Image 610-5a depicts a probe 611a, a trabecular meshwork 70a, a juxtacanalicular trabecular meshwork (JCTM) 70b, an inner wall 70c of Schlemm's canal, an outer wall 70d of Schlemm's canal, and a sclera 70e. Schlemm's canal is represented by the space between inner wall 70c and outer wall 70d. The reference numbering included in FIG. 7D-4 corresponds to that which is provided in FIGS. 7D and 7D-2, with the letter "a" added to certain reference numbers. Hence, reference number 608 in FIG. 7D corresponds to reference number 608a in FIG. 7D-4.

As illustrated in FIG. 7D-3 (augmented image 760), in OCT image 610-6, a real time image may show probe marker 611 moving toward the trabecular meshwork 9, as the microscope image 761 shows distal tip marker 605 moving toward treatment reference marker 601, and hence the surgeon can view the displayed movement of the probe as the probe tip advances toward the target. As shown in OCT image 620-6, when the probe tip advances toward the target, the fiber optic tip distance marker 608 may move closer to the distance markers corresponding to the target tissue region, which may include the trabecular meshwork and Schlemm's canal, as depicted by distance marker 609-1 (corresponding to trabecular meshwork), 609-2 (corresponding to juxtacanalicular trabecular meshwork), 609-3 (corresponding to inner wall of Schlemm's canal), 609-4 (corresponding to outer wall of Schlemm's canal), and 609-5 (corresponding to sclera). For clarity. FIG. 7D-1 shows a magnified view of an A-scan image 620-6 showing a plurality of A-scan distance markers, which may be overlaid on the augmented image.

As shown in FIG. 7E-2 (augmented image 770), when the probe tip is in contact with the trabecular meshwork as depicted in the optical image or view 771, the probe marker is in contact with the trabecular meshwork as shown in OCT image 610-7, and distance marker 609-1 may disappear from OCT image 620-7. When the probe tip is in contact with the trabecular meshwork, photoablation of the target tissue may be performed. The probe coupled to an energy source may be configured to deliver a plurality of pulses to the target location upon detecting that the distal end of the elongate probe is compressing the portion of the trabecular meshwork. As described herein, the plurality of pulses is configured to produce an aperture through the trabecular meshwork and into the Schlemm's canal by photoablation. For clarity, FIG. 7E shows a magnified view of an A-scan image 620-7 showing a plurality of A-scan distance markers, which may be overlaid on the augmented image.

As shown in FIG. 7E-3 (augmented image 780), the A-scan distance markers in OCT image 620-8 may indicate a penetration of the Schlemm's canal inner wall. For instance, when the inner wall of the Schlemm's canal has been penetrated as shown in OCT image 610-8, the lines 609-2 and 609-3 may disappear from the augmented image 780 indicating the probe tip has passed the inner wall of the SC (or that the inner wall of Schlemm's canal has otherwise been penetrated) and in some cases, physician may retract the elongate probe once the inner wall of the Schlemm's canal has been penetrated. According to some embodiments, a fiberoptic-based OCT can be used to detect tissue structures within the target tissue region, and can be used to detect when the inner wall of Schlemm's canal has been ablated and penetrated. Relatedly, because the ablation process converts the tissue into gas, detection of gas in Schlemm's canal (which was previously filled only with liquid, e.g. plasma or aqueous humor) can be used as another marker to identify when the inner wall of Schlemm's canal has been penetrated. The laser firing may automatically stop upon detection of penetration of the inner wall of Schlemm's canal, for example. Alternatively, in another example, the user may be notified by a processor to manually stop the laser firing. For clarity, FIG. 7E-1 shows a magnified view of an A-scan image 620-8 showing a plurality of A-scan distance markers, which may be overlaid on the optical image or view 781 shown in FIG. 7E-3, to form at least part of the augmented image 780.

The controlling unit 410 (e.g. as depicted in FIG. 4, 5, 8, 10, or 11) may comprise a steering and control unit 414 configured to automatically control the energy source to deliver the plurality of pulses upon detecting that the distal end of the elongate probe is compressing the portion of the trabecular meshwork. Alternatively, the steering and control unit 414 may be configured to generate an alert to the physician to manually control the energy source to deliver the plurality of pulses upon detecting that the distal end of the elongate probe is compressing the portion of the trabecular meshwork. In some cases, the steering and control unit 414 may be configured to determine an amount by which the portion of the trabecular meshwork is compressed by the distal end of the elongate probe based on the A-scan distance markers. For instance, the amount of compression of the trabecular meshwork is determined based on a change in relative distance between a first distance marker corresponding to the surface of the trabecular meshwork and a second distance marker corresponding to the JCTM. In another instance, the steering and control unit 414 is configured to determine whether the portion of the trabecular meshwork is compressed to a predetermined thickness based on the A-scan distance markers. In some cases, the steering and control unit 414 may be configured to control an energy source to deliver a plurality of pulses to cause photoablation of the portion of the trabecular meshwork and the inner wall of the Schlemm's Canal upon determining that the portion of the trabecular meshwork has been compressed to the predetermined thickness Referring back to FIGS. 7E to 7E-3, the energy source may stop delivering the plurality of pulses to the target location upon detecting that the inner wall of the Schlemm's canal has been penetrated by the laser pulses. The inner wall of the Schlemm's canal penetration may be indicated by the disappearance of the line marker 609-3 corresponding to the inner wall of the Schlemm's canal. In some cases, the steering and control unit 414 may be configured to detect whether the inner wall of the Schlemm's canal has been penetrated by the photoablation of the portion of the trabecular meshwork based in part on changes in relative distances between the A-scan distance markers. In some cases, the steering and control unit 414 is further configured to generate an alert to the physician to retract the elongate probe away from the target location upon detecting that the inner wall of the Schlemm's canal is penetrated. The alert may be in any form such as text, graphical visual elements overlaid over the optical image or audible alert.

Figure 7F:
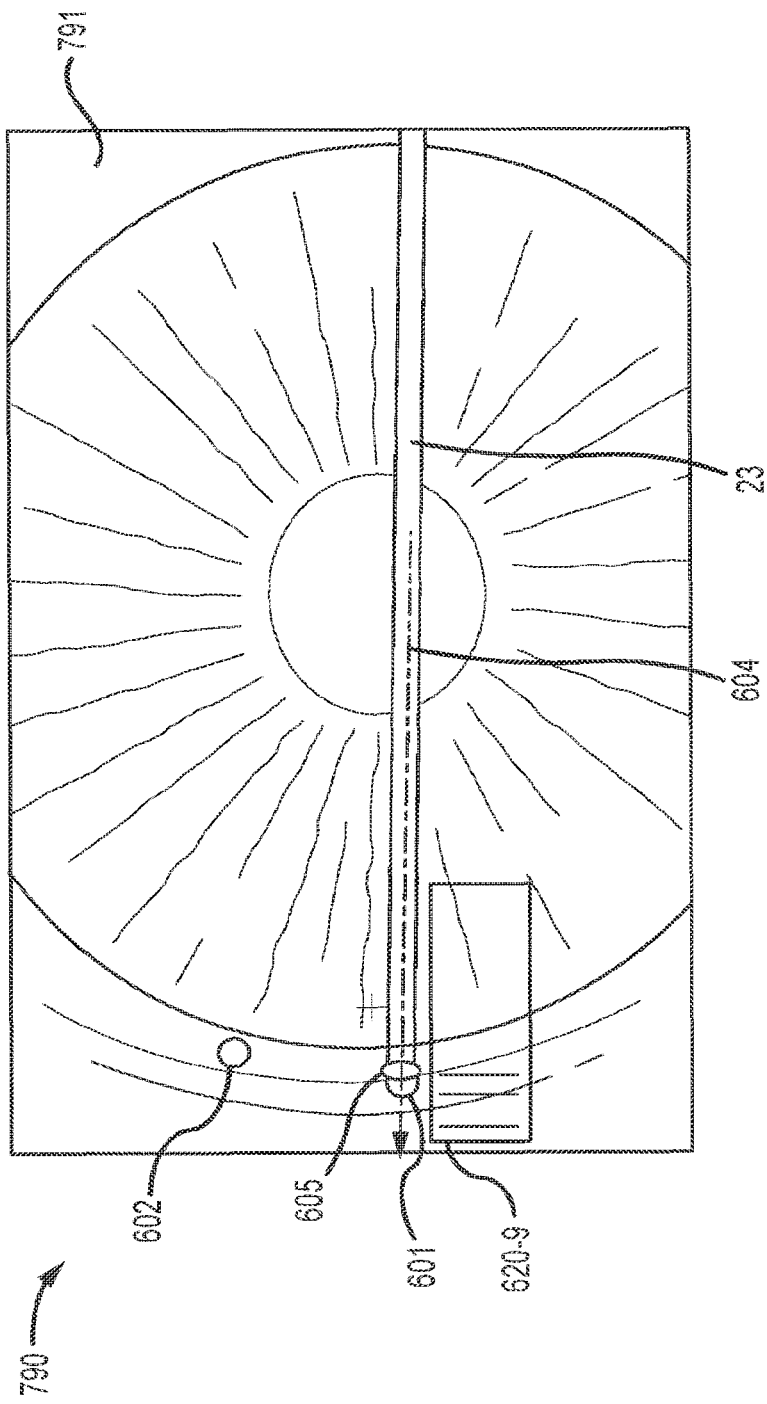
Figures 1, 7F:
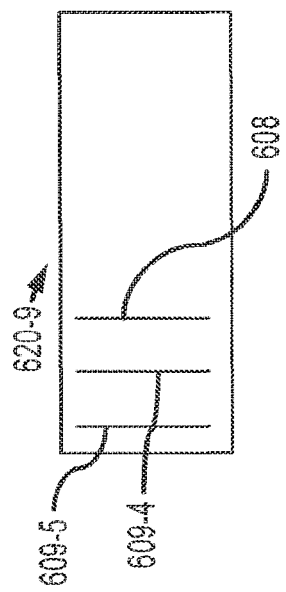

As illustrated in FIG. 7F (augmented image 790), the steering and control unit may be further configured to generate an alert to the physician to locate another treatment reference marker corresponding to the mapped location of another target location of the eye upon successful completion of the current operation. For example, when the inner wall of Schlemm's canal is detected to be penetrated and laser pulses are stopped, the subsequent treatment reference marker 602 corresponding to the next target location may appear and the surgeon can be guided to move to the next treatment location as described elsewhere herein. Some or all of the previous described steps may be repeated for the subsequent target locations. For clarity, FIG. 7F-1 shows a magnified view of an A-scan image 620-9 showing a plurality of A-scan distance markers, which may be overlaid on the optical image or view 791 so as to form at least part of the augmented image 790.

Figure 8:
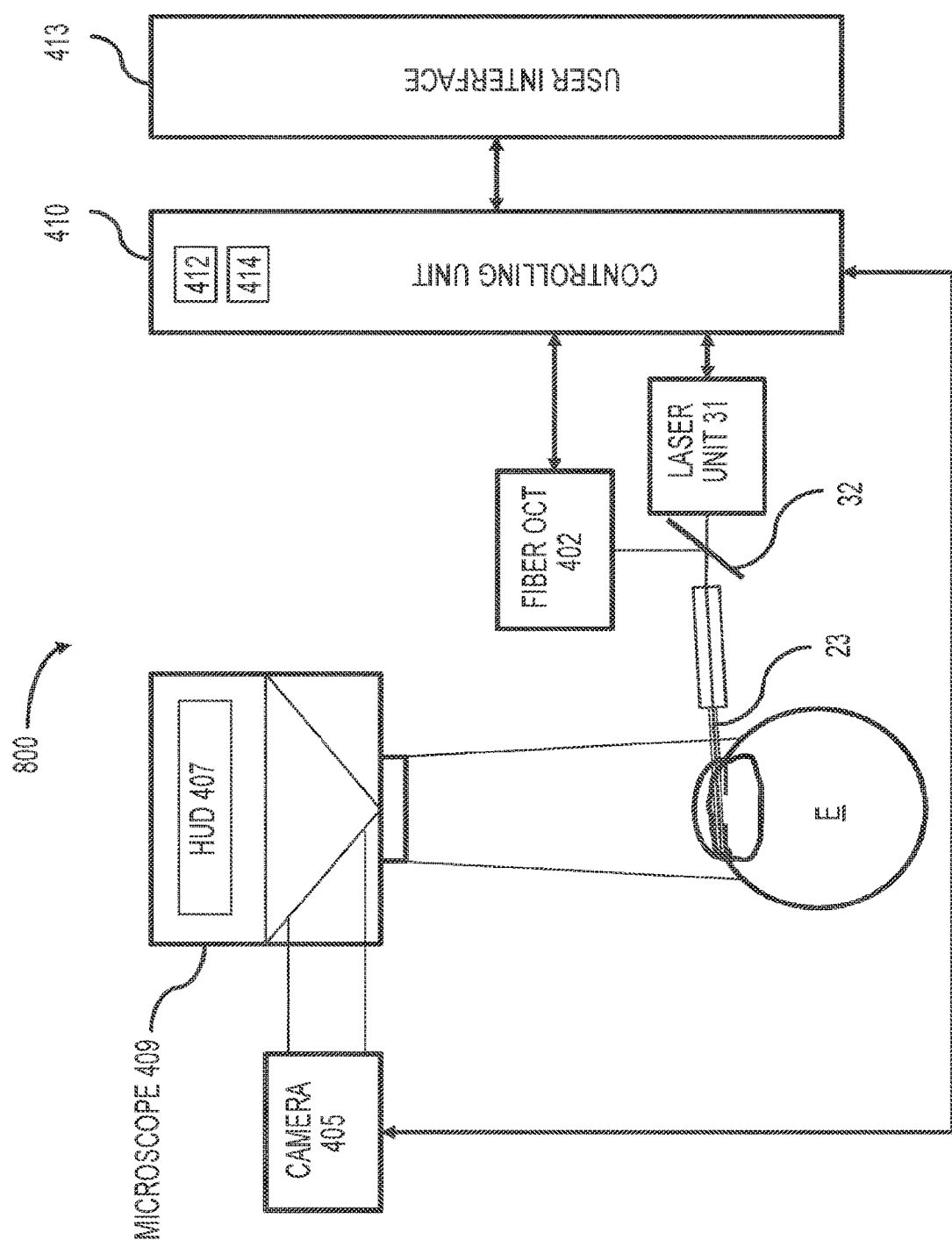
FIG. 8 shows an exemplary system based on fiberoptic-based OCT, in accordance with embodiments of the invention.

FIG. 8 shows another example of the system 800, accordance with embodiments. The system 800 may be substantially the similar to the system 400 as described in FIG. 4, and may comprise one or more components of system 400. The system 800 may utilize only a fiberoptic-based OCT 402 to measure the eye E with OCT. The microscope 409 may comprise the same optical microscope as described in FIG. 4. In this case, the OCT unit 401 may comprise only the fiberoptic-based OCT 402, and the OCT unit may not share optical components of the microscope 409. The A-scan information provided by the probe can be used to determine a distance from the trabecular meshwork. The surgeon can use the A-scan information provided on the display to align the probe with Schlemm's canal. For example, the A-scan information can be displayed to the surgeon with an indication of the distance from Schlemm's canal, and an indication as to whether the distal end of the fiber optic probe is aligned with Schlemm's canal, for example.

FIGS. 9-2 and 9-3 show exemplary augmented images 900 and 910 shown to a user during a procedure using the system 800. The steps of overlaying guidance arrows, probe markers, probe tip markers 605, treatment reference markers to the optical image or view may be similar to those described in FIGS. 7A, 7A-1, and 7B, in images 700, 710, and 720. The orientation and advancing direction of the probe may be adjusted to such that the probe axial marker is aligned with the guidance arrow. The alignment of the probe in the x-y plane may be achieved by using the top-down view of the optical image of the eye. The position of the probe relative to the target location in the anterior-posterior plane may be estimated or calculated by a preoperative OCT image. When the probe tip (corresponding to distal tip marker 605) is detected to be within a predetermined distance from the target location (corresponding to treatment reference marker 601), a fiberoptic-based OCT scan may be performed. The fiberoptic-based OCT scan may be an axial scan (i.e., A-scan) or B-scan as described above. The fiberoptic-based OCT scan can be the same as described elsewhere herein. A magnified view 620-90 of the OCT result may be overlaid onto the optical image 901 so as to generate augmented image 900. The OCT image 620 may comprise a plurality of A-scan distance reference markers such as 608, 609-1 as described previously. Alternatively, the OCT image may comprise a two-dimensional OCT live image when a B-scan is performed. The OCT image 620-90 and 620-91 are useful to guide the physician in advancing the tip in the axial direction, and provides information about the relative position of the probe tip with respect to one or more tissues structures (e.g., trabecular meshwork 609-1). For example, as shown in image 910, as the tip is advanced, the distance marker 608 in the OCT image 620-91 may move toward the other distance markers. For clarity, FIGS.

9 and 9-1 show magnified views of A-scan images 620-90 and 620-91 showing a plurality of A-scan distance markers, which may be overlaid on the augmented image. In some cases, a magnified view 620-91 of the OCT result may be overlaid onto the optical image 911 so as to generate augmented image 910.

Figure 10:
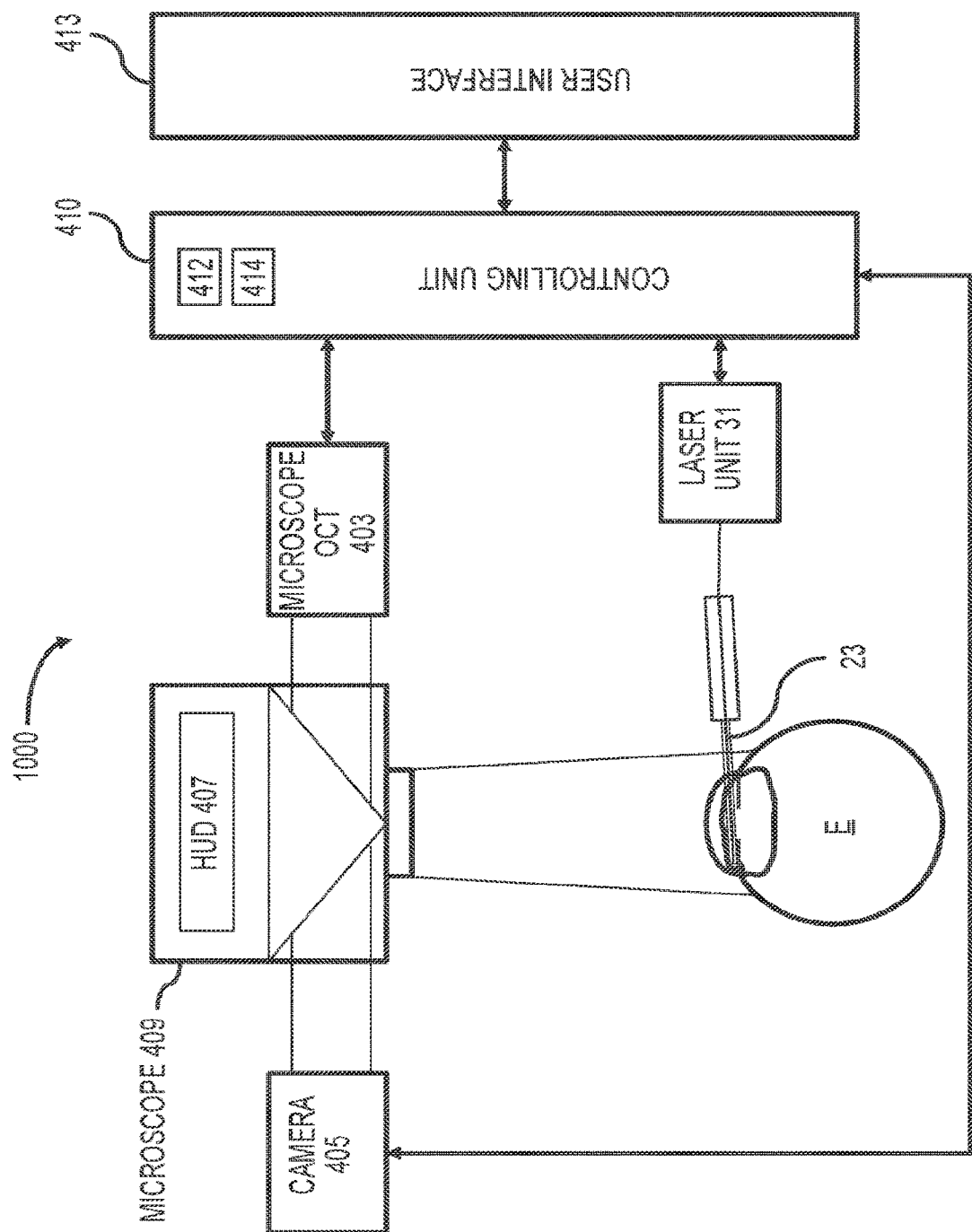
FIG. 10 shows an exemplary system based on microscope-based OCT, in accordance with embodiments of the invention.

FIG. 10 shows another example of the system 1000, in accordance with embodiments of the invention. The system 1000 may utilize only a microscope-based OCT unit 403. The OCT unit in the system 1000 may comprise a microscope-based OCT. In this case, the OCT based augmented information overlaid onto the optical image may be provided by the OCT scan performed by the microscope-based OCT unit 403. For instance, when the probe tip is detected to be within a predetermined distance from the target location, a microscope-based OCT scan may be performed. The scan plane may be along an anterior-posterior plane of the eye E and along the probe elongated axis as described elsewhere herein. The OCT scan may be a high resolution scan. For example, a structural scan resolution may be in a range from about 1 μm to about 5 μm. The scan may provide positional information of the probe tip relative to the target location or tissue structures (e.g., trabecular meshwork, juxtacanalicular trabecular meshwork (JCTM), an inner wall of the Schlemm's canal, an outer wall of the Schlemm's canal, or sclera). In some cases, a real time OCT image with markers such as image 610 may be produced and overlaid onto the optical image. In some cases, in addition to the image 610, a magnified view of relative positions of the probe tip and the tissue structure such as image 620 may be generated based on the microscope-based OCT and overlaid onto the optical image.

Figure 11:
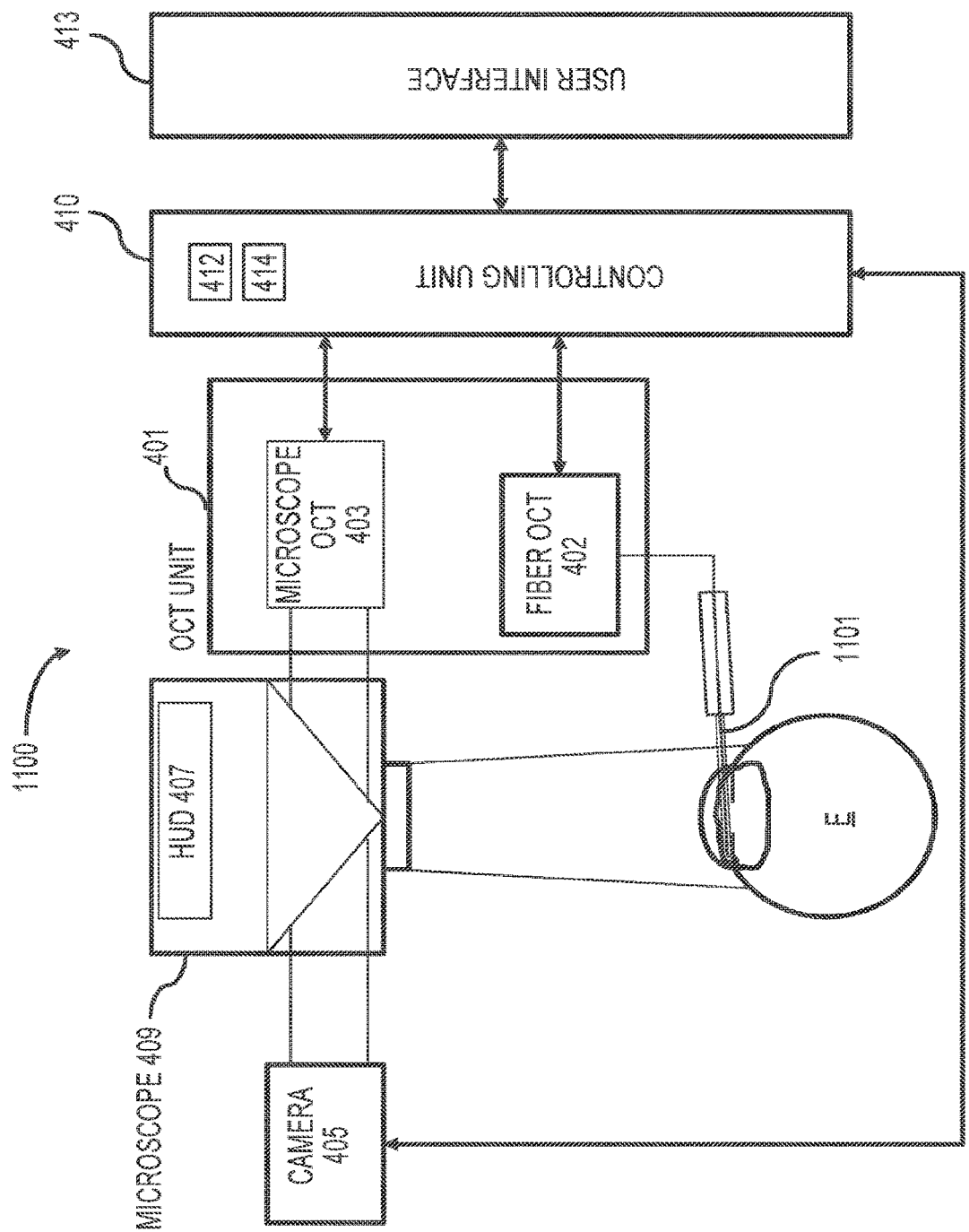
FIG. 11 schematically illustrates an example of the OCT guidance system 1100, in accordance with embodiments of the invention.

FIG. 11 schematically illustrates an example of the OCT guidance system 1100, in accordance with embodiments of the invention. The system 1100 may comprise the same components of the system 400 as described in FIG. 4, except that the system 1100 may not comprise a separate laser unit for the fiber optic probe. The system 1100 may be used for guiding any surgical tools inserted internal to the eye E as described elsewhere herein. For instance, the system 1100 may provide guidance to locate stent location for implant. Examples of implant devices include the CyPass® microstent and the iStent®, which target the suprachoroidal space and Schlemm's canal, respectively. In this case, the fiber optic for the OCT scan may be co-axial with a surgical tool 1101 that may not comprise the fiber optic for the ELT surgery.

FIGS. 12A to 12D-4 show examples of instruments that can be used in combination with the provided system. The various instruments may not be coupled to a laser source. The device may comprise a substantially elongated shape. As illustrated in the anterior view of an eye depicted in FIGS. 12A and 12A-1, augmented information may be overlaid onto the optical view or image 505 of the eye and the instrument in a similar as described elsewhere herein. For instance, one or more treatment reference markers 601 and an arrow or probe line 604 co-axial to the instrument 24 may be superimposed to the optical image. As shown here, the eye includes an iris 19, a trabecular meshwork 9, and a cornea 15. It is understood that instead of depicting the cornea 15, this image could also depict the sclera in substitution of the cornea. In an optical image or view 505 shown here, it is possible to visualize the anatomical structures of the eye within the anterior chamber, from the inner pupil to the iridocorneal angle. As discussed elsewhere herein, however, the peripheral structures at or near the iridocorneal angle, such as the trabecular meshwork 9, may not be visible in the optical image or view. Hence, according to some embodiments, the optical image or view provided here is for illustration purpose only, and in practice will not include such peripheral structures.

A guidance arrow 612 may be displayed to guide the advancing direction and orientation of the instrument 24. In some cases, the fiber optic for OCT scan may be co-axial or enclosed in a housing of the instrument 24 to provide a relative position of the distal end of the instrument with respect to treatment location. In some cases, an elongate probe 24 may comprise one or more stents 1220a loaded thereon, and the stents 1220a may be implanted in the trabecular meshwork 9 and configured to connect the anterior chamber to the Schlemm's canal and create a permanent opening into Schlemm's canal. Embodiments of the system described herein can be configured to aid a physician in advancing and implanting the one or more stents 1220a at target locations with aid of the graphical visual elements (e.g. treatment reference markers and arrows) registered with a real microscope image of the eye. For example, the disclosed system may be configured to aid the physician in advancing and sliding a stent 1220a sideways into Schlemm's canal and positioning the stent permanently in Schlemm's canal with aid of the graphical visual elements (e.g. treatment reference marker 601, probe line 604, and/or guidance arrow 612) registered with the microscope image.

In some cases, the system may be configured to aid the physician in advancing a plurality of stents along an elongate axis of the elongate probe, injecting the plurality of stents into Schlemm's canal, and positioning the plurality of stents permanently in Schlemm's canal, with aid of the graphical visual elements registered with the microscope image. For example, as depicted in FIG. 12B-1, an elongate probe 1210b includes a housing 1212b and an insertion mechanism 1214b. As depicted in FIG. 12B-2, the insertion mechanism 1214b can be loaded with a stent 1220b, and the stent 1220b can include a head 1222b, a thorax 1224b, a flange 1226b, and an outflow orifice 1228b. FIG. 12B-3 depicts two stents 1220b which have been implanted into the trabecular meshwork 9, as viewed from the anterior chamber. As shown here, the flange 1226b of each stent 1220b includes an inlet orifice 1227b, which is in fluid communication with one or more outflow orifices (not shown). Because stents 1220b do not extend significantly from the trabecular meshwork 9 toward the central portion of the anterior chamber, the stents are not visible in a microscope image or view as a result of being obscured due to total internal reflection of the corner near the iridocorneal angle of the eye. OCT guidance embodiments as disclosed elsewhere herein are well suited for assisting the surgeon in delivering the stents (while loaded on the elongate probe) to the trabecular meshwork 9. For example, OCT guidance embodiments as discussed with reference to FIG. 6 can be used to help guide the surgeon to implant a stent at a target location in the trabecular meshwork. In some cases, the target location can correspond to the location of a collector channel, or be based on the distribution or density of multiple collector channels. With reference to FIG. 12B-4, when a stent 1220b is implanted in the eye, the flange 1226b resides in the anterior chamber 7, the thorax (not visible) resides in the trabecular meshwork 9, and the head 1222b resides in Schlemm's canal 11. Because the inlet orifice is in fluid communication with the outflow orifices, aqueous humor can flow from the anterior chamber into Schlemm's canal.

As depicted in FIGS. 12C-1 to 12C-7, in some cases, an elongate probe 1210c may comprise a micro-stent 1220c loaded thereon, and the micro-stent 1220*c* may be configured to create a permanent conduit between the anterior chamber 7 and a supraciliary space 27. In some cases, the stent 1220*c* may include a sleeve 1221*c*, such as a titanium sleeve, an inlet 1222*c*, a retention feature 1223*c*, and an outlet 1224*c*. The system disclosed herein can be configured to aid the physician in advancing the micro-stent 1220*c* to the supraciliary space 27 with aid of the graphical visual elements registered with the microscope image. For example, the system can be configured to aid the physician in advancing the micro-stent 1220*c* to the supraciliary space 27 using a real time OCT image of the supraciliary space 27 generated by any of the OCT apparatus described elsewhere herein. The system can also be configured to aid the physician in positioning a proximal collar portion or sleeve 1221*c* of the micro-stent 1220*c* in an anterior chamber angle 28 with aid of the graphical visual elements registered with the microscope image. OCT guidance embodiments as disclosed elsewhere herein are well suited for assisting the surgeon in delivering the stent (while loaded on the elongate probe) to the anterior chamber angle. For example, OCT guidance embodiments as discussed with reference to FIG. 6 can be used to help guide the surgeon to implant a stent at a target location in the anterior chamber angle.

In some cases, as depicted in FIGS. 12D-1 to 12D-4, an elongate probe 1210*d* may comprise a gel stent 1220*d* configured for subconjunctival filtration loaded thereon. As shown in FIG. 12D-1, an injector or elongate probe 2120*d* can be inserted through an incision in the cornea 15, and advanced across the anterior chamber 7. As shown in FIG. 12D-2, the elongate probe can be further advanced into the subconjunctival space 27. FIG. 12D-3 illustrates deployment of the distal portion of the gel stent 1220*d* into the subconjunctival space. FIG. 12D-4 depicts gel stent 1220*d* in the implanted position, where it functions to drain aqueous humor from the anterior chamber 7 into the subconjunctival space 27. The gel stent 1220*d* may be configured to create a channel through the sclera to allow flow of aqueous humor from the anterior chamber into a subconjunctival space. The system disclosed herein can be configured to aid the physician in positioning and implanting the gel stent 1220*d* with aid of the graphical visual elements registered with the microscope image. For example, OCT guidance embodiments as disclosed elsewhere herein are well suited for assisting the surgeon in delivering the stent (while loaded on the elongate probe) to the subconjunctival space. Relatedly, OCT guidance embodiments as discussed with reference to FIG. 6 can be used to help guide the surgeon to implant a stent at a target location in the subconjunctival space.

Figure 13:
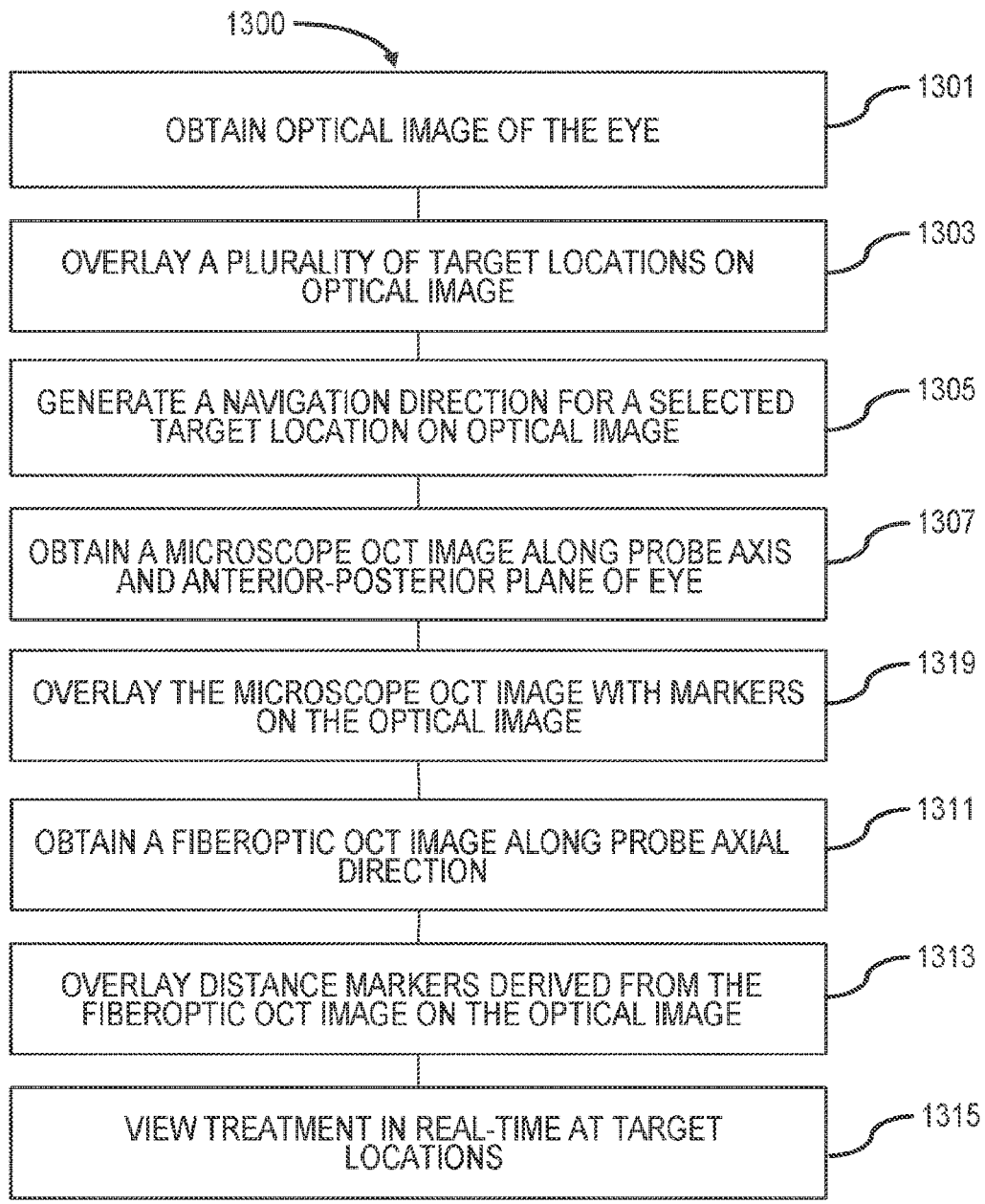
FIG. 13 shows a flowchart of a method for determining a target location and probe location, in accordance with embodiments.

FIG. 13 shows a flowchart of a method 1300 for determining a target treatment location and probe location, in accordance with embodiments. The method may use one or more of the systems described herein. In a first step 1301, an anterior image of the eye may be obtained by a camera or video camera of an optical microscope. In a second step 1303, one or more target locations (or treatment reference markers corresponding to the target locations) are overlaid or mapped over the optical image or optical view to the user. The one or more target locations may be determined based on reference image data comprising an OCT image of the eye. The OCT image of the eye may be obtained using an OCT apparatus prior to the surgical procedure. In some cases, the OCT image of the eye may comprise an image of an anterior segment of the eye comprising a network of collector channels and one or more individual collector channels in at least two quadrants from the OCT image may be identified. The preoperative OCT image may have high resolution.

FIGS. 15A to 15C show examples of preoperative OCT images 1500, and augmented preoperative OCT images 1510 and 1520 showing collector channels and target locations. As shown in the examples, the preoperative OCT images may be 3D images. One or more collector channels and/or target locations may be identified from the high resolution preoperative images. As discussed elsewhere herein, the trabecular meshwork 9 is in fluid communication with a series or network of collector channels 12 (via Schlemm's canal). OCT image 1500 depicts locations $9a_1$, $9a_2$, and $9a_3$ of the trabecular meshwork 9 associated with subsurface tissue where the number or density of collector channels 12 is relatively high. In contrast, location 9*b* of the trabecular meshwork 9 is associated with subsurface tissue where the number or density of collector channels 12 is relatively low. The locations can be selected based on any of a variety of criteria. For example, the locations $9a_1$, $9a_2$, and $9a_3$ can be selected based on number or density of collector channels, such that $9a_1$ corresponds to the location having the most number or highest density of collector channels, $9a_2$ corresponds to the location having the next most number or highest density of collector channels, and $9a_3$ corresponds to the location having the next most number or highest density of collector channels. The ordering of the target locations can also be selected so that the first location is where collector channels are larger and/or collector channel networks or fields are more dense, and the following locations are selected in descending order based on the size and/or density criteria. In some embodiments, the locations and/or ordering of the locations can be based on based on a preoperative OCT image or a real-time OCT image. In some cases, the locations and/or ordering of the locations can be chosen by a surgeon or by artificial intelligence pattern recognition techniques.

In some cases, augmented information such as guidance arrows 613 may be overlaid onto the preoperative images. For example, preoperative OCT image 1510 is overlaid with a guidance arrow 613 that can be used for guiding an elongate probe toward a target location. As depicted in FIGS. 15A to 15C, preoperative OCT image 1510 can also be combined with a microscope view or microscope image 1505, in which iris 19 and elongate probe 23 can be seen. As noted above, the locations $9a_1$, $9a_2$, and $9a_3$ can be selected and ordered based on number or density of collector channels corresponding to those respective locations. A treatment reference marker 601 can be overlaid on the OCT image and/or on the microscope view or image at target location 621 corresponding to location $9a_1$, as depicted in FIG. 15B.

Relatedly, a guidance arrow 613 can point to the location corresponding to treatment reference marker 601 and/or target location 621. In this way, the surgeon can be guided to perform an ablation at target location 621. In some embodiments, this may be the first treatment ablation step applied to the patient eye. A series of ablations can be performed in this way. For example, a treatment reference marker 602 can be overlaid on the OCT image and/or on the microscope view or image at target location 622 corresponding to location 982, as depicted in FIG. 15C. Relatedly, a guidance arrow 613 can point to the location corresponding to treatment reference marker 602 and/or target location 622. In this way, the surgeon can be guided to perform an ablation at target location 622. In some embodiments, this may be the second treatment ablation step applied to the patient eye. Although the guidance arrow 613 in FIGS. 15B and 15C is depicted as originating from a location that is somewhat proximal along the probe 23, it is appreciated that in some embodiments, a guidance arrow can originate from a location that is distal along the probe, for example as shown in FIG. 6. In some cases, the guidance arrow can provide an alignment indication to the surgeon, so that the surgeon may co-linearly align the probe with the guidance arrow.

As discussed elsewhere herein, a treatment reference marker can correspond to or can be mapped to a target location in an OCT image. In some cases, one or more target locations can be identified or designated in an OCT image. In some cases, the one or more target locations (e.g. 621, 622) are located at positions corresponding to the one or more individual collector channels (or alternatively, positions corresponding to one or more regions containing dense networks or fields of collector channels) proximal to the trabecular meshwork and an inner wall of the Schlemm's canal. As shown here, treatment reference marker 601 can be overlaid on the OCT image and/or on the microscope view or image at target location 621, and treatment reference marker 602 can be overlaid on the OCT image and/or on the microscope view or image at target location 622. In some cases, locations of the one or more individual collector channels (or network regions) may be registered relative to at least one distinguishable anatomical structure in the eye such as the iris. The plurality of target locations may be estimated manually by the user or automatically by the processor. A user or physician may be allowed to select a target location through the user interface as described elsewhere herein. According to some embodiments, the technique of identifying target locations and/or treatment reference markers depicted in FIGS. 15A to 15C can be used in conjunction with a subsequent goniolens-facilitated treatment. According to some embodiments, the technique of identifying target locations and/or treatment reference markers depicted in FIGS. 15A to 15C can be used in conjunction with other OCT guided techniques discussed herein with reference to, for example, FIG. 6. As shown in FIGS. 15A to 15C, an OCT image can be used to identifying and/or target collector channels or networks of collector channels. Target locations can be selected based on where collector channels are larger and/or collector channel networks or fields are more dense (e.g. 4 o'clock position), as opposed to where collector channels are smaller and/or collector channel networks are less dense (e.g. 2 o'clock position). In some cases, a target location can be designated to at positions in Schlemm's canal that are close to the collector channels are larger, the collector channel networks or fields are more dense, and/or the collector channels, networks, or fields are the least obstructed (e.g. that provide the highest volume of outflow). In some cases, target locations can be ranked or ordered based on these size, density, and/or obstruction or flow parameters. In some cases, OCT images can be used to determine locations where flow in Schlemm's canal is circumferential and/or where flow is segmented, and target locations can be selected so as to correspond to locations where flow is circumferential. In some cases, a surgeon can use OCT images such as those depicted in FIGS. 15A to 15C to make a decision regarding where to position or move a treatment probe or device, without requiring the assignment of a target location or the overlaying of a graphical visual element. For example, the OCT image may show the collector channels, networks, and/or fields, and the surgeon may make the probe positioning or movement decision based on such anatomical features. In some cases, the surgeon can make the decision based on a visual inspection of the anatomical features depicted in the image. The OCT image can enable the surgeon to identify a target location or desired treatment location positioned in the tissue without requiring that that target location or treatment location be labeled or marked, for example with a graphical visual element or a treatment reference marker.

With returning reference to FIG. 13, in a third step 1305, one or more guidance graphical elements may be superimposed to the optical image such that the physician may adjust the advancing direction and/or orientation of the probe to move towards the selected target location in at least the optical image plane. In a fourth step 1307, when the probe tip is detected to be within a predetermined distance from the target location, a microscope-based OCT image may be obtained along the longitudinal axis of the probe and the anterior-posterior plane of the eye. Next 1309, the microscope-based OCT image and associated markers may be overlaid onto the optical image to guide the physician in adjusting the probe orientation and advancing direction in the OCT image plane. In a sixth step 1311, a fiberoptic-based OCT scan may be performed along the axis of the probe. The fiberoptic-based OCT scan may be an A-scan or B-scan to provide relative position between the probe tip and tissues when the probe tip is within a predetermined distance from the target location. According to some embodiments, a microscope-based OCT scan is performed to obtain a microscope-based OCT image, and no fiberoptic-based OCT scan is performed. According to some embodiments, a fiberoptic-based OCT scan is performed to obtain a fiberoptic-based OCT image, and no microscope-based OCT scan is performed. According to some embodiments, a microscope-based OCT scan is performed to obtain a microscope-based OCT image, and a fiberoptic-based OCT scan is performed to obtain a fiberoptic-based OCT image. In some cases, a microscope-based OCT scan and a fiberoptic-based OCT scan are performed sequentially. In some cases, a microscope-based OCT scan and a fiberoptic-based OCT scan are performed simultaneously. The fiberoptic-based OCT image and/or distance markers generated based on the OCT image may be overlaid to the optical image 1313. In an eighth step 1315, the treatment may be displayed or viewed in real-time at the treatment locations in order to adjust movement of the probe based at least in part on the augmented information.

Although FIG. 13 shows a method in accordance with some embodiments a person of ordinary skill in the art will recognize many adaptations for variations. For example, the steps can be performed in any order. Some of the steps may be deleted, some of the steps repeated, and some of the steps may comprise sub-steps of other steps. The method may also be modified in accordance with other aspects of the disclosure as provided herein.

Figure 13A:
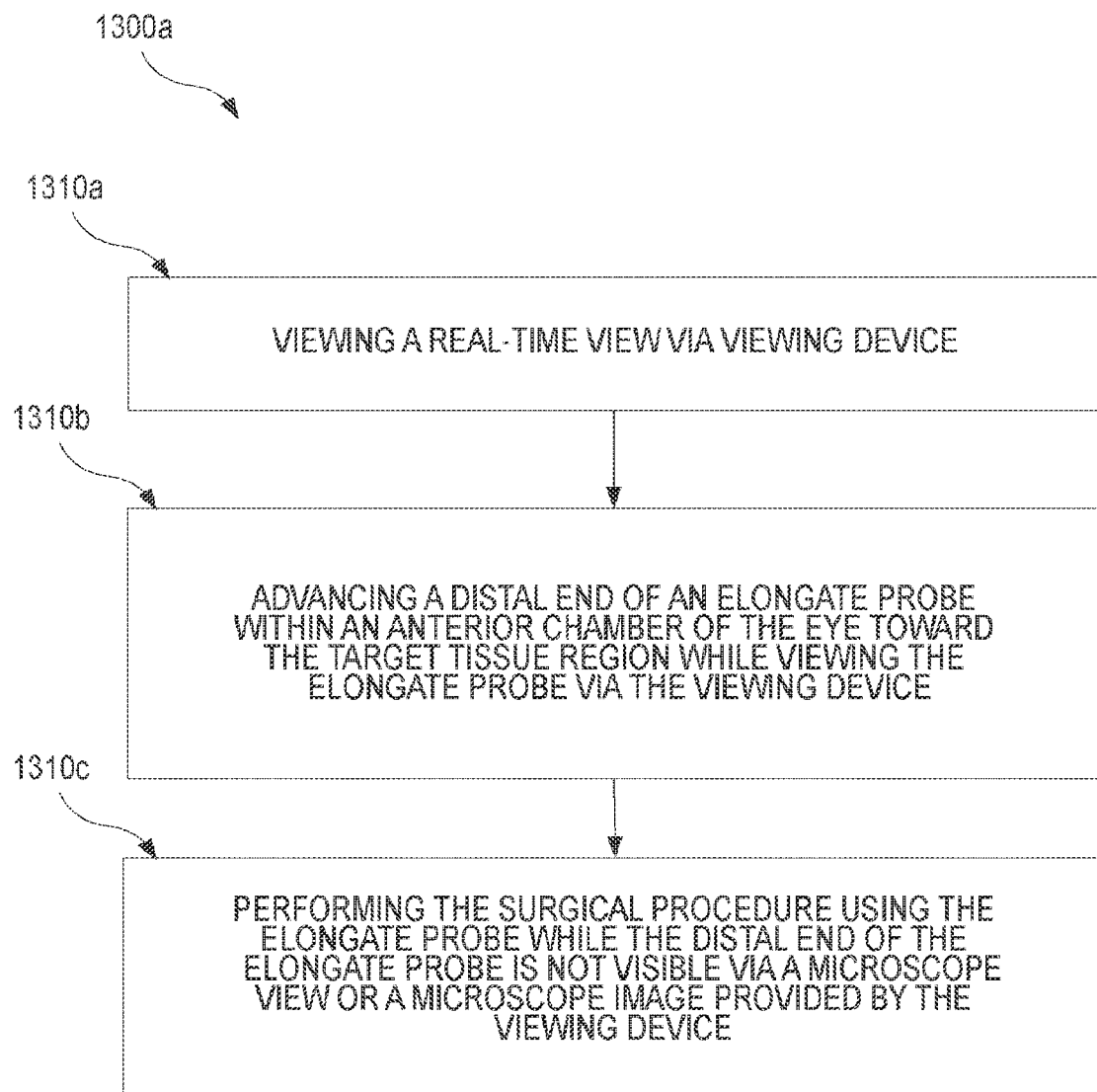
FIGS. 13A and 13B depict aspects of treatment methods and aiding methods, respectively, according to embodiments of the present invention.

As shown in FIG. 13A, embodiments of the present invention encompass methods for performing surgical procedures at a target location of an eye of a patient. An exemplary treatment method 1300*a* includes viewing a real-time view via a viewing device, as illustrated by step 1310*a*, advancing a distal end of an elongate probe within an anterior chamber of the eye toward the target tissue region while viewing the elongate probe via the viewing device, as illustrated by step 1320*a*, and performing the surgical procedure using the elongate probe while the distal end of the elongate probe is not visible via a microscope view or a microscope image provided by the viewing device, and while perceiving information from a microscope view or a microscope image regarding a relative position of the distal end of the elongate probe with respect to the target location, as illustrated by step 1330*a*. According to some embodiments, the target location is positioned in a target tissue region of an eye of a patient. In some cases, the real-time view includes a microscope view of the eye or an augmented image. The augmented image can include the microscope view of the eye or a microscope image of the eye. The augmented image can further include an optical coherence tomography (OCT) image of the target tissue region. The OCT image can be registered with the microscope view or the microscope image. A graphical visual element corresponding to the target location can be overlaid the microscope view or the microscope image. The target location may not be visible in the microscope view or the microscope image. According to some embodiments, methods include advancing the distal end of the elongate probe within the anterior chamber of the eye toward the target tissue region while viewing the microscope view or the augmented image on the viewing device. In some cases, the distal end of the elongate probe is initially visible in the microscope view or the microscope image and thereafter becomes not visible in the microscope view or the microscope image due to total internal reflection in a region of the eye. In some cases, this region of the eye includes the target tissue region. In some cases, this region is beyond the "critical angle" visibility, as discussed elsewhere herein.

Figure 13B:
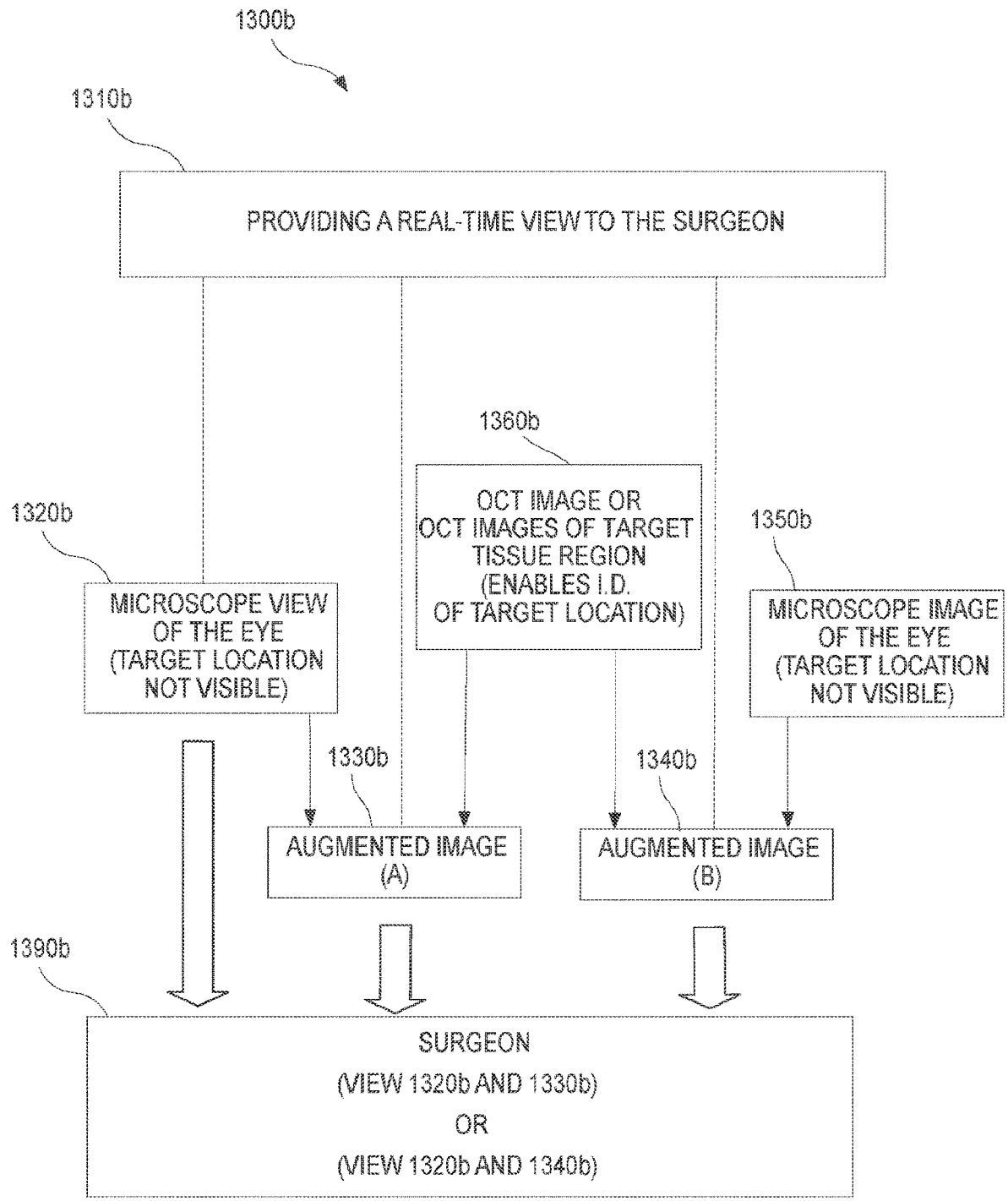

As shown in FIG. 13B, embodiments of the present invention encompass methods of assisting a surgeon to perform a surgical procedure on an eye of a patient. As shown here, method 1300b includes providing a real-time view to the surgeon, as illustrated by step 1310b. In some cases, the real-time view includes a microscope view of the eye 1320b. In some cases, the real-time view includes an augmented image, such as augmented image 1330b or augmented image 1340b. In some cases, an augmented image 1330b (version (A)) can include the microscope view of the eye 1320b. In some cases, an augmented image 1340b (version (B)) can include a microscope image of the eye 1350b. Either version of the augmented image (i.e. augmented image 1330b or augmented image 1340b) can include an OCT image of a target tissue region of the eye 1360b. The OCT image 1360b can enable identification of a target location. In some embodiments, a surgeon 1390 can view microscope view 1320b, and then view either augmented view 1330b or augmented view 1340b. Hence, the surgeon 1390 can be provided with two different versions of a real-time view, namely microscope view 1320b and augmented image 1330b, or microscope view 1320b and augmented image 1340b. According to some embodiments, the OCT image or OCT images 1360b can be registered with the microscope view 1320b or the microscope image 1350b. According to some embodiments, an actual target location is not visible in the microscope view 1320b or the microscope image 1350b. According to some embodiments, the augmented image (1330b or 1340b) enables the surgeon 1390b to perceive information regarding a relative position of a distal end of an elongate probe with respect to the target location when the distal end of the elongate probe is not visible in the microscope view 1320b or the microscope image 1350b.

In some embodiments, the surgeon 1390b views the microscope image 1320b when initially inserting a treatment probe into the anterior chamber of the patient's eye. Subsequently, an OCT image 1360b (e.g. showing collector channels or networks) can be overlaid to the microscope image 1320b, for example using registration techniques as discussed elsewhere herein. The surgeon may then decide where to deliver the treatments (e.g. laser ablation energy applied to trabecular meshwork, juxtacanalicular trabecular meshwork, and inner wall of Schlemm's canal). In some cases, this may involve the surgeon using a graphical visual element or a treatment reference marker to label or mark the treatment location. In some cases, a computerized system may make the determination of where to place a graphical visual element or treatment reference marker. Subsequent to the above steps, the surgeon can move or position the treatment probe within the anterior chamber of the eye, and a subsequent OCT imaging protocol can be used to facilitate (e.g. via overlays of graphical visual elements) guiding or navigation of the probe to a target or desired treatment location. In some cases, graphical visual elements can be overlaid to a microscope view or image prior to placing the probe in the anterior chamber. In some cases, graphical visual elements can be overlaid to a microscope view or image subsequent to placing the probe in the anterior chamber. In some cases, graphical visual elements can be overlaid to an OCT image prior to placing the probe in the anterior chamber. In some cases, graphical visual elements can be overlaid to an OCT image subsequent to placing the probe in the anterior chamber.

The controlling unit 410 (e.g. as depicted in FIG. 4, 5, 8, 10, or 11) may comprise one or more processors (e.g. such as processor 1405 depicted in FIG. 14) configured with instructions for perform one or more steps illustrated in FIGS. 13,13A, and 13B, and operations as described elsewhere herein. Similarly, the controlling unit 410 may include or be in connectivity with any other component of a computer systems (e.g. such as computer system 1401 depicted in FIG. 14).

Although certain methods and apparatus disclosed herein are described in the context of ablation, the user interface and display can be configured to direct surgical placement of implants as described herein. For example, the target locations can be shown with reference to the collector channels, and the surgical placement of an implant can be directed to a target location near Schlemm's canal, for example. The arrows and other features shown on the heads up display can be used to direct placement of a plurality of locations of a plurality of surgical implants to be placed in the eye, for example implants to create openings to Schlemm's canal. The implant can be placed by creating an opening into Schlemm's canal mechanically (e.g. with a sharp instrument) and placing the implant at the target location, for example.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules may optionally include data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing method steps as describe elsewhere herein. All features of the described systems are applicable to the described methods mutatis mutandis, and vice versa. In some cases, systems and methods may involve identifying the location of Schlemm's canal from across the anterior to guide a treatment fiber to the trabecular meshwork which overlies Schlemm's canal to enable the surgeon to direct the fiber probe to this target from a location where the probe is visible optically via the microscope image to a location where the probe is not visible through the microscope image but within the region of total internal reflection as the probe is advanced into the angle structures to contact the trabecular meshwork over Schlemm's canal. In some cases, systems and methods may involve identifying when the probe which has contacted the trabecular meshwork over Schlemm's canal has compressed the trabecular meshwork to a predetermined thickness. In some cases, systems and methods may involve identifying when the channel which has been created by photoablation of the trabecular meshwork and the inner wall of Schlemm's canal has precisely penetrated the inner wall of Schlemm's canal (to enable the discontinuance of any further laser pulses).

The processor may be a hardware processor such as a central processing unit (CPU), a graphic processing unit (GPU), or a general-purpose processing unit. The processor can be any suitable integrated circuits, such as computing platforms or microprocessors, logic devices and the like. Although the disclosure is described with reference to a processor, other types of integrated circuits and logic devices are also applicable. The processors or machines may not be limited by the data operation capabilities. The processors or machines may perform 512 bit, 256 bit, 128 bit, 64 bit, 32 bit, or 16 bit data operations.

Figure 14:
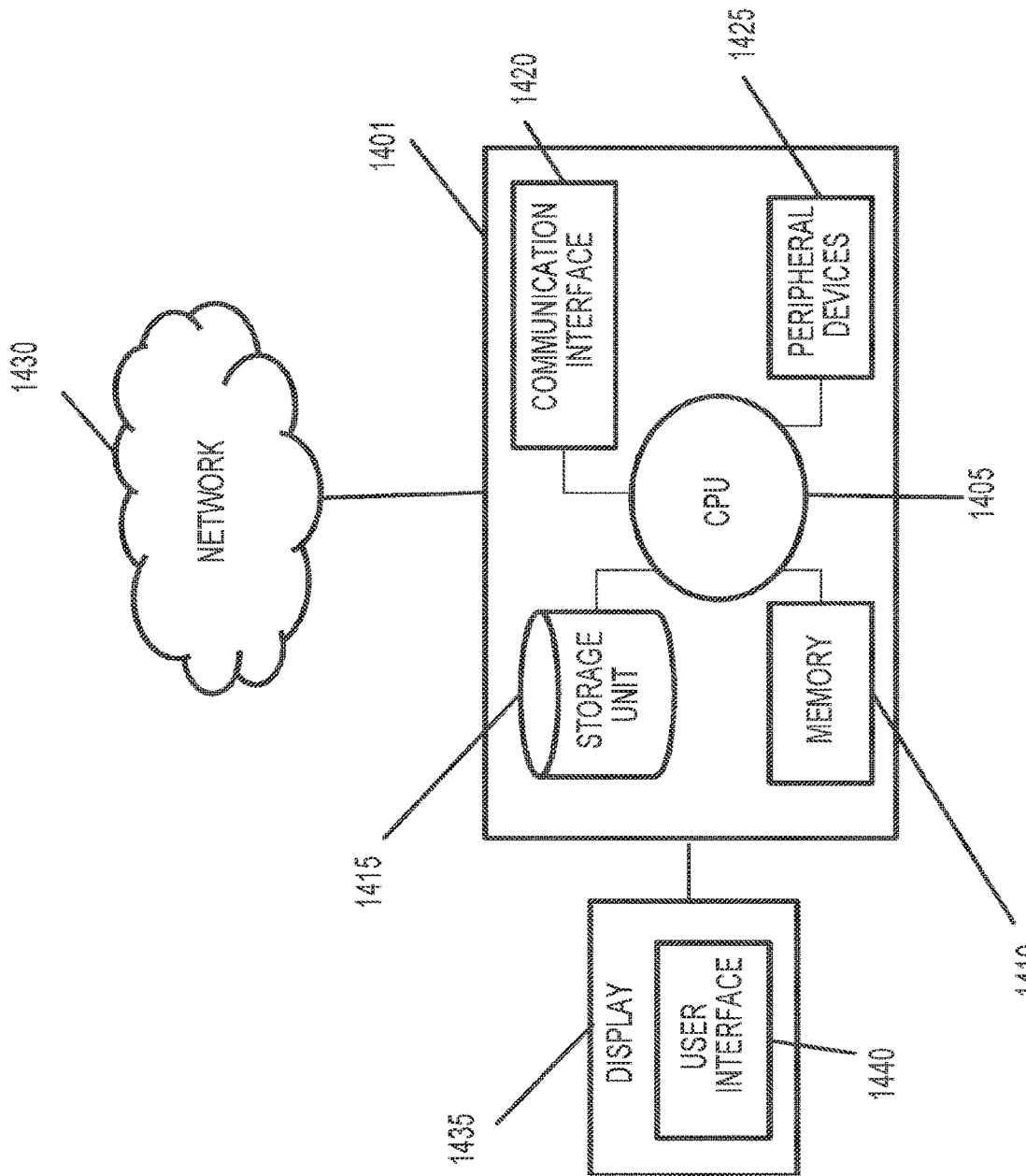
FIG. 14 shows an analyzing and control system that can be configured to implement any analyzing and control systems disclosed in the present application.

In some embodiments, the processor may be a processing unit of a computer system. FIG. 14 shows a computer system 1401 that can be configured to implement any computing system or method disclosed in the present application. The computer system 1401 can comprise a mobile phone, a tablet, a wearable device, a laptop computer, a desktop computer, a central server, or the like.

The computer system 1401 includes a central processing unit (CPU, also "processor" and "computer processor" herein) 1405, which can be a single core or multi core processor, or a plurality of processors for parallel processing. The CPU can be the processor as described above. The computer system 1401 also includes memory or memory location 1410 (e.g., random-access memory, read-only memory, flash memory), electronic storage unit 1415 (e.g., hard disk), communication interface 1420 (e.g., network adapter) for communicating with one or more other systems, and peripheral devices 1425, such as cache, other memory, data storage and/or electronic display adapters. In some cases, the communication interface may allow the computer to be in communication with another device such as the imaging device or audio device. The computer may be able to receive input data from the coupled devices for analysis. The memory 1410, storage unit 1415, interface 1420 and peripheral devices 1425 are in communication with the CPU 1405 through a communication bus (solid lines), such as a motherboard. The storage unit 1415 can be a data storage unit (or data repository) for storing data. The computer system 1401 can be operatively coupled to a computer network ("network") 1430 with the aid of the communication interface 1420. The network 1430 can be the Internet, an internet and/or extranet, or an intranet and/or extranet that is in communication with the Internet. The network 1430 in some cases is a telecommunication and/or data network. The network 1430 can include one or more computer servers, which can enable distributed computing, such as cloud computing. The network 1430, in some cases with the aid of the computer system 1401, can implement a peer-to-peer network, which may enable devices coupled to the computer system 1401 to behave as a client or a server.

The CPU 1405 can execute a sequence of machine-readable instructions, which can be embodied in a program or software. The instructions may be stored in a memory location, such as the memory 1410. The instructions can be directed to the CPU 1405, which can subsequently program or otherwise configure the CPU 1405 to implement methods of the present disclosure. Examples of operations performed by the CPU 1405 can include fetch, decode, execute, and writeback.

The CPU 1405 can be part of a circuit, such as an integrated circuit. One or more other components of the system 1401 can be included in the circuit. In some cases, the circuit is an application specific integrated circuit (ASIC).

The storage unit 1415 can store files, such as drivers, libraries and saved programs. The storage unit 1415 can store user data, e.g., user preferences and user programs. The computer system 1401 in some cases can include one or more additional data storage units that are external to the computer system 1401, such as located on a remote server that is in communication with the computer system 1401 through an intranet or the Internet.

The computer system 1401 can communicate with one or more remote computer systems through the network 1430. For instance, the computer system 1401 can communicate with a remote computer system of a user. Examples of remote computer systems include personal computers, slate or tablet PC's, smart phones, personal digital assistants, and so on. The user can access the computer system 1401 via the network 1430.

Methods as described herein can be implemented by way of machine (e.g., computer processor) executable code stored on an electronic storage location of the computer system 1401, such as, for example, on the memory 1410 or electronic storage unit 1415. The machine executable or machine readable code can be provided in the form of software. During use, the code can be executed by the processor 1405. In some cases, the code can be retrieved from the storage unit 1415 and stored on the memory 1410 for ready access by the processor 1405. In some situations, the electronic storage unit 1415 can be precluded, and machine-executable instructions are stored on memory 1410.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media (e.g. a tangible non-transitory computer readable medium), terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. In exemplary embodiments, computer-executable code, which may also be referred to as processor-executable code, can be embodied in a tangible non-transitory computer readable medium and/or stored on an electronic storage location, which may also be referred to as a storage media. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1401 can include or be in communication with an electronic display 1435 that comprises a user interface 1440 for providing, for example, a management interface. Examples of UI's include, without limitation, a graphical user interface (GUI) and web-based user interface. The user interface 1440 may be the same as the user interface 413 as described in FIG. 4. Alternatively, the user interface may be a separate user interface.

The computer system 1401 may comprise various other computer components to facilitate communication with an external device such as the microscope system, camera. OCT unit, laser unit, external processor or memory. The communication modules may include suitable means for instruction and data transfer such as double data rate. Various means can be employed for communication such as peripheral component interconnect card, computer buses including but not limited to PCI express, PCI-X, Hyper-Transport, and so forth. Suitable communication means may be selected according to the requirements of the bandwidth and compatibility of the external device and the central processing unit 1405. For example, one data bus may be for command transfer (e.g., AXI4lite bus) to the laser unit 31 and a different data bus (e.g., AXI4 bus) may be used for image data transfer. Alternatively or additionally, wireless communication may be employed.

Methods and systems of the present disclosure can be implemented by way of one or more algorithms. An algorithm can be implemented by way of software upon execution by the central processing unit 1405.

As used here, the terms "overlay", "overlaid", "superimpose", "superimposed", and the like, may in some embodiments also encompass other image or information combining techniques, including "underlay", "underlaid", "subjacent", and similar approaches. It will be appreciated that composite or fused images, views, information, or displays, which may combine or blend images, graphical visual elements, and/or information, or the like, which may be present in a single layer or multiple layers, can be generated or provided by any of these techniques.

Any of the system, device, or method embodiments disclosed herein may involve or include the use systems, devices, or methods such as those disclosed in U.S. Patent Publication Nos. 2004/0082939, 2012/0283557, 2016/0095751, and 2017/0202708, and U.S. Pat. Nos. 4,846,172, 6,251,103, 8,540,659, 8,679,089, 9,603,741, 9,642,746, 9,820,883, and 9,833,357, the contents of each of which are incorporated herein by reference.

Although reference is made to determining locations of collector channels with markers shown on a display, the eye can be marked prior to surgery at locations corresponding to the collector channels using the methods and apparatus as disclosed herein. The surgeon can use these markings to create openings to Schlemm's canal in response to the markings placed on the eye. For example, the eye can be marked with ink to identify locations of preferred surgical treatment, and the openings created in the trabecular meshwork at locations corresponding to the preferred surgical treatment. While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system, comprising:
   a probe, wherein the probe is configured to be insertable into and repositionable in an opening in tissue of an eye;
   an optical coherence tomography (OCT) unit, wherein the OCT unit is configured to transmit and receive OCT data regarding the probe and at least a portion of the tissue of the eye, including tissue distal to a distal end of the probe, to generate the OCT data of the probe and at least one of target tissue or adjacent tissue;
   a processor, wherein the processor is configured to determine a location of the probe relative to at least one of the target tissue or the adjacent tissue, wherein the location is updated as the probe is repositioned;
   an imaging device, wherein the imaging device is configured to generate an OCT image of at least the distal end of the probe, and at least one of the target tissue or the adjacent tissue, from the OCT data, and is further configured to generate at least one of a microscopic image or an optical image of at least the portion of the tissue of the eye; and a viewing device, wherein the viewing device is configured to present an augmented image, wherein the augmented image includes the OCT image of at least the distal end of the probe and the at least one of the target tissue or the adjacent tissue, and wherein the augmented image further includes the at least one of the microscopic image or the optical image, wherein the augmented image enables identification of a first location on the at least one of the target tissue or the adjacent tissue, wherein the first location and the distal end of the probe are located in an area of the eye which is not visible in the at least one of the microscopic image or the optical image, wherein the augmented image further includes a first graphical visual element, wherein the first graphical visual element represents and identifies one of the distal end of the probe or an implant disposed at the distal end of the probe, wherein the distal end of the probe is advanceable toward the first location on the at least one of the target tissue or the adjacent tissue, and wherein the augmented image further includes a second graphical visual element, wherein the second graphical visual element represents and identifies the first location on the at least one of the target tissue or the adjacent tissue, wherein the OCT unit is configured to direct an OCT imaging beam to the area of the eye which is not visible in the at least one of the microscopic image or the optical image, and which area includes the distal end of the probe, without using the at least one of the microscopic image or the optical image, and wherein the first graphical visual element which represents and identifies the one of the distal end of the probe or the implant disposed at the distal end of the probe, and the second graphical visual element which represents and identifies the first location on the at least one of the target tissue or the adjacent tissue, are viewable in the augmented image presented on the viewing device as the distal end of the probe approaches the first location on the at least one of the target tissue or the adjacent tissue.

2. The system of claim 1, wherein the OCT unit comprises at least one of a microscope-associated OCT unit or a fiber-based OCT unit.

3. The system of claim 2, wherein the OCT unit comprises the microscope-associated OCT unit, and wherein the microscope-associated OCT unit is incorporated within a microscope device.

4. The system of claim 2, wherein the OCT unit comprises the microscope-associated OCT unit, and wherein the microscope-associated OCT unit is adjacent to a microscope device.

5. The system of claim 2, wherein the OCT unit comprises the fiber-based OCT unit, and wherein the fiber-based OCT unit comprises an optical fiber configured to transmit and receive the OCT data.

6. The system of claim 5, wherein the optical fiber is further configured to transmit a treatment light to the first location on the at least one of the target tissue or the adjacent tissue.

7. The system of claim 2, wherein the OCT unit comprises the fiber-based OCT unit, and wherein the fiber-based OCT unit comprises an array of fibers comprising a first fiber and a second fiber, the first fiber configured to transmit and receive the OCT data and the second fiber is concurrently configured to transmit a treatment light to the first location on the at least one of the target tissue or the adjacent tissue.

8. The system of claim 1, wherein the probe is configured to advance the implant to the first location on the at least one of the target tissue or the adjacent tissue.

9. The system of claim 1 wherein the first location on the at least one of the target tissue or the adjacent tissue is determined based on preoperative OCT data, wherein the processor is configured to process the preoperative OCT data to identify collector channels in the tissue of the eye, and to select the first location based on the collector channels identified by processing the preoperative OCT data.

10. The system of claim 1, wherein the OCT data is intra-operative OCT data, wherein the first location on the at least one of the target tissue or the adjacent tissue is determined based on the intra-operative OCT data, wherein the processor is configured to process the intra-operative OCT data to identify collector channels in the tissue of the eye, and to select the first location based on the collector channels identified by processing the intra-operative OCT data.

11. The system of claim 1, wherein the second graphical visual element is positioned to show a relative distance between the one of the distal end of the probe or the implant at the distal end of the probe, and the first location on the at least one of the target tissue or the adjacent tissue.

12. The system of claim 11, wherein the second graphical visual element is configured to change based on a position and an orientation of the probe.

13. The system of claim 11, wherein the second graphical visual element changes when the target tissue or the adjacent tissue has been penetrated.

14. The system of claim 1, wherein the viewing device is separate from the imaging device.

15. The system of claim 1, wherein the target tissue or the adjacent tissue comprises at least one of a trabecular meshwork of the eye or at least a portion of a Schlemm's canal of the eye.

16. The system of claim 15, wherein the at least one of the microscopic image or the optical image provides a view of an anterior chamber of the eye, the at least one of the microscopic image or the optical image lacking a view of the trabecular meshwork of the eye and a view of the Schlemm's canal due to total internal reflection of visible light when viewing through a cornea of the eye.

17. The system of claim 15, wherein the second graphical visual element corresponds to an inner wall of the Schlemm's canal.

18. A system, comprising:
a probe, wherein the probe is configured to be insertable into and repositionable in an opening in tissue of an eye;
an optical coherence tomography (OCT) unit, wherein the OCT unit is configured to transmit and receive OCT data regarding the probe and at least a portion of the tissue of the eye, including tissue distal to a distal end of the probe, to generate the OCT data of the probe and at least one of target tissue or adjacent tissue;
a processor, wherein the processor is configured to determine a location of the probe relative to at least one of the target tissue or the adjacent tissue, wherein the location is updated as the probe is repositioned;
an imaging device, wherein the imaging device is configured to generate an OCT image of at least the distal end of the probe, and at least one of the target tissue or the adjacent tissue, from the OCT data, and is further configured to generate at least one of a microscopic image or an optical image of at least the portion of the tissue of the eye; and a viewing device, wherein the viewing device is configured to present an augmented image, wherein the augmented image includes the OCT image of at least the distal end of the probe and the at least one of the target tissue or the adjacent tissue, and wherein the augmented image further includes the at least one of the microscopic image or the optical image, wherein the augmented image enables identification of a first location on the at least one of the target tissue or the adjacent tissue, wherein the first location is not visible in the at least one of the microscopic image or the optical image, wherein the augmented image further includes a first graphical visual element, wherein the first graphical visual element represents and identifies one of the distal end of the probe or an implant disposed at the distal end of the probe, wherein the distal end of the probe is advanceable toward the first location on the at least one of the target tissue or the adjacent tissue, and wherein the augmented image further includes a second graphical visual element, wherein the second graphical visual element represents and identifies the first location on the at least one of the target tissue or the adjacent tissue, wherein the first graphical visual element which represents and identifies the one of the distal end of the probe or the implant disposed at the distal end of the probe, and the second graphical visual element which represents and identifies the first location on the at least one of the target tissue or the adjacent tissue, are viewable in the augmented image presented on the viewing device as the distal end of the probe approaches the first location on the at least one of the target tissue or the adjacent tissue, wherein the target tissue or the adjacent tissue comprises at least one of a trabecular meshwork of the eye or at least a portion of a Schlemm's canal of the eye, and wherein the processor is further configured to perform operations including:

determining, from the OCT data, a thickness of the trabecular meshwork of the eye; and displaying, on the viewing device, data corresponding to the determined thickness of the trabecular meshwork of the eye.

19. The system of claim 18, wherein the data corresponding to the determined thickness of the trabecular meshwork of the eye is configured to allow a determination whether the trabecular meshwork of the eye is compressed.

20. The system of claim 1, wherein the target tissue or the adjacent tissue comprises at least one of a supraciliary space in the eye, a subconjunctival space in the eye, an iris, a cornea, or an anterior chamber of the eye, the target tissue or the adjacent tissue being in a region where total internal reflection precludes optical visualization of at least the distal end of the probe without use of a gonio lens.

21. The system of claim 1, wherein the system is configured to be operated in an area where the one of the distal end of the probe or the implant disposed at the distal end of the probe is not visible in the at least one of the microscopic image or optical image due to total internal reflection, the system being operated by using the OCT image of the one of the distal end of the probe of the implant disposed at the distal end of the probe.

22. The system of claim 1, wherein at least one of the processor and the viewing device is configured to generate the graphical visual element from the OCT data.

23. The system of claim, 1, wherein the OCT image shows the one of the distal end of the probe or the implant disposed at the distal end of the probe when the one of the distal end of the probe or the implant disposed at the distal end of the probe is not visible in the at least one of the microscopic image or the optical image.

24. The system of claim 15, wherein the system is configured to indicate when the one of the distal end of the probe or the implant at the distal end of the probe has contacted the trabecular meshwork or when the one of the distal end of the probe or the implant at the distal end of the probe has penetrated the inner wall of Schlemm's canal, based on the OCT data.

* * * * *